(12) United States Patent
Ganz et al.

(10) Patent No.: US 11,141,177 B2
(45) Date of Patent: *Oct. 12, 2021

(54) BLOCKAGE CLEARING DEVICES, SYSTEMS, AND METHODS

(71) Applicant: Piranha Medical, LLC, Salt Lake City, UT (US)

(72) Inventors: Robert A. Ganz, Minnetonka, MN (US); Mark Anders Rydell, Golden Valley, MN (US); Travis Sessions, Cedar Hills, UT (US); Steven Berhow, St. Michael, MN (US); Doug Wahnschaffe, Monticello, MN (US); Michael W. Augustine, St. Michael, MN (US)

(73) Assignee: Piranha Medical LLC, Salt Lake City, UT (US)

( * ) Notice: Subject to any disclaimer, the term of this patent is extended or adjusted under 35 U.S.C. 154(b) by 29 days.

This patent is subject to a terminal disclaimer.

(21) Appl. No.: 15/995,112

(22) Filed: May 31, 2018

(65) Prior Publication Data

US 2018/0280040 A1 Oct. 4, 2018

Related U.S. Application Data

(63) Continuation-in-part of application No. 15/356,975, filed on Nov. 21, 2016, now Pat. No. 10,722,267.

(Continued)

(51) Int. Cl.
*A61B 17/22* (2006.01)
*A61B 17/00* (2006.01)
(Continued)

(52) U.S. Cl.
CPC ........ *A61B 17/22* (2013.01); *A61B 17/00234* (2013.01); *A61B 17/3207* (2013.01);
(Continued)

(58) Field of Classification Search
CPC .............. A61B 17/1632; A61B 17/22; A61B 17/22012; A61B 17/22031;
(Continued)

(56) References Cited

U.S. PATENT DOCUMENTS 4,715,848 A 12/1987 Beroza
4,754,755 A 7/1988 Husted
(Continued)

FOREIGN PATENT DOCUMENTS

CN 201642262 U 11/2010
CN 103142308 A 6/2013
(Continued)

OTHER PUBLICATIONS

American Society for Gastrointestinal Endoscopy, Management of Ingested Foreign Bodies and Food Impactions, Gastrointestinal Endoscopy Journal, 2011, pp. 1085-1091, vol. 73, No. 6.
(Continued)

*Primary Examiner* — Robert A Lynch
(74) *Attorney, Agent, or Firm* — Med Venture Management, LLC; Daniel C. Higgs

(57) ABSTRACT

A system for clearing a blockage in a patient can include a tubular member that defines a channel and is insertable into an esophagus of the patient. The system can include a catheter assembly that includes a catheter tube defining a length greater than a length of the tubular member and being passable through the channel of the tubular member. The catheter tube can include a distal tip that defines a cutting element to core the blockage positioned in the esophagus. The catheter assembly can further include a catheter hub fixedly secured to the catheter tube and couplable with a vacuum line such that, when suction is provided via the vacuum line, advancement of the catheter tube into contact
(Continued)

with the blockage cores a piece from the blockage that is passed through the catheter tube.

9 Claims, 56 Drawing Sheets

Related U.S. Application Data

(60) Provisional application No. 62/513,419, filed on May 31, 2017, provisional application No. 62/636,526, filed on Feb. 28, 2018, provisional application No. 62/260,873, filed on Nov. 30, 2015.

(51) Int. Cl.

| | |
|---|---|
| A61B 17/3207 | (2006.01) |
| A61B 17/32 | (2006.01) |
| A61B 17/50 | (2006.01) |
| A61B 90/00 | (2016.01) |
| A61B 17/3205 | (2006.01) |

(52) U.S. Cl.
CPC ...... *A61B 17/320016* (2013.01); *A61B 17/50* (2013.01); *A61B 17/32053* (2013.01); *A61B 2017/0034* (2013.01); *A61B 2017/00561* (2013.01); *A61B 2017/00778* (2013.01); *A61B 2017/00818* (2013.01); *A61B 2017/00845* (2013.01); *A61B 2017/22062* (2013.01); *A61B 2017/22069* (2013.01); *A61B 2017/22079* (2013.01); *A61B 2090/062* (2016.02); *A61B 2090/0807* (2016.02); *A61B 2217/005* (2013.01)

(58) Field of Classification Search
CPC ........ A61B 17/22035; A61B 17/32053; A61B 17/3207; A61B 17/320758; A61B 17/50; A61B 2017/008; A61B 2017/18; A61B 2017/22079; A61B 2017/320775; A61B 2017/320791; A61M 25/0021; A61M 25/0023; A61M 25/0082
See application file for complete search history.

(56) References Cited

U.S. PATENT DOCUMENTS

| | | | |
|---|---|---|---|
| 4,772,258 A | 9/1988 | Marangoni et al. | |
| 4,898,575 A | 2/1990 | Fischell et al. | |
| 5,033,466 A | 7/1991 | Weymuller, Jr. | |
| 5,114,399 A | 5/1992 | Kovalcheck | |
| 5,197,949 A | 3/1993 | Angsupanich | |
| 5,222,971 A | 6/1993 | Willard et al. | |
| 5,571,168 A | 11/1996 | Toro | |
| 5,695,448 A | 12/1997 | Kimura et al. | |
| 5,741,269 A | 4/1998 | McCredy | |
| 5,782,837 A | 7/1998 | York | |
| 5,904,679 A | 5/1999 | Clayman | |
| 5,921,971 A | 7/1999 | Agro et al. | |
| 5,931,831 A | 8/1999 | Linder | |
| 6,042,593 A * | 3/2000 | Storz ............... | A61B 17/32002 606/159 |
| 6,361,540 B1 | 3/2002 | Gauderer et al. | |
| 6,689,062 B1 | 2/2004 | Mesallum | |
| 6,699,260 B2 | 3/2004 | Dubrul et al. | |
| 6,719,772 B2 | 4/2004 | Trask et al. | |
| 6,840,909 B2 | 1/2005 | Gatto | |
| 6,962,585 B2 * | 11/2005 | Poleo, Jr. ............. | A61B 18/245 606/15 |
| 6,971,988 B2 | 12/2005 | Orban, III | |
| 6,986,773 B1 | 1/2006 | Manougian | |
| 7,204,804 B2 | 4/2007 | Zirps et al. | |
| 7,220,253 B2 | 5/2007 | Kantsevoy et al. | |
| 7,575,548 B2 | 8/2009 | Takemoto et al. | |
| 7,727,186 B2 | 6/2010 | Makower et al. | |
| 8,016,785 B2 | 9/2011 | Kantsevoy et al. | |
| 8,016,838 B2 | 9/2011 | Kaye et al. | |
| 8,057,484 B2 | 11/2011 | Secrest et al. | |
| 8,377,075 B2 | 2/2013 | Lichtenstein et al. | |
| 8,573,218 B2 | 11/2013 | Rutter | |
| 8,591,521 B2 | 11/2013 | Cherry et al. | |
| 8,602,974 B2 | 12/2013 | Goldwasser et al. | |
| 8,852,219 B2 | 10/2014 | Wulfman et al. | |
| 8,870,824 B2 | 10/2014 | Kusakabe | |
| 8,876,838 B2 | 11/2014 | Winiarski | |
| 8,906,169 B2 | 12/2014 | Bagwell et al. | |
| 9,549,761 B2 | 1/2017 | Green et al. | |
| 10,722,267 B2 | 7/2020 | Ganz et al. | |
| 2005/0228224 A1 | 10/2005 | Okada et al. | |
| 2005/0240147 A1 | 10/2005 | Makower et al. | |
| 2006/0074478 A1 * | 4/2006 | Feller, III ......... | A61B 17/12022 623/1.11 |
| 2006/0293612 A1 * | 12/2006 | Jenson ............... | A61B 17/3207 600/585 |
| 2007/0208252 A1 | 9/2007 | Makower | |
| 2007/0250149 A1 | 10/2007 | Van Oepen et al. | |
| 2008/0103410 A1 | 5/2008 | Karpiel et al. | |
| 2008/0103508 A1 | 5/2008 | Karakurum | |
| 2008/0119693 A1 | 5/2008 | Makower et al. | |
| 2008/0188868 A1 | 8/2008 | Weitzner et al. | |
| 2008/0243137 A1 * | 10/2008 | D'Angelo ...... | A61B 17/320758 606/106 |
| 2009/0187098 A1 | 7/2009 | Makower et al. | |
| 2010/0016885 A1 | 1/2010 | Eidenschink et al. | |
| 2011/0275990 A1 * | 11/2011 | Besser ............. | A61B 17/22032 604/99.01 |
| 2011/0282353 A1 | 11/2011 | McHugo | |
| 2012/0004596 A1 * | 1/2012 | Thomas ......... | A61B 17/320758 604/22 |
| 2012/0071856 A1 * | 3/2012 | Goldfarb ................. | A61B 17/24 604/514 |
| 2013/0103063 A1 | 4/2013 | Escudero et al. | |
| 2014/0052114 A1 * | 2/2014 | Ben-Oren ............ | A61B 1/3137 606/15 |
| 2014/0150782 A1 | 6/2014 | Vazales et al. | |
| 2014/0277066 A1 | 9/2014 | Schaeffer et al. | |
| 2014/0309673 A1 | 10/2014 | Dacuycuy et al. | |
| 2015/0025558 A1 | 1/2015 | Wulfman et al. | |
| 2015/0057517 A1 | 2/2015 | Pease et al. | |
| 2016/0081702 A1 | 3/2016 | Kan et al. | |
| 2016/0262722 A1 | 9/2016 | Marmor et al. | |
| 2016/0331645 A1 | 11/2016 | Bagwell et al. | |
| 2016/0374700 A1 | 12/2016 | Olden et al. | |
| 2017/0150993 A1 | 6/2017 | Ganz et al. | |
| 2018/0344993 A1 | 12/2018 | Ganz et al. | |

FOREIGN PATENT DOCUMENTS

| | | |
|---|---|---|
| KR | 100834042 B1 | 5/2008 |
| WO | 2008042987 A2 | 4/2008 |
| WO | 2008121292 A1 | 10/2008 |
| WO | 2017095682 A1 | 6/2017 |
| WO | 2018222948 A1 | 12/2018 |
| WO | 2020092959 A1 | 5/2020 |

OTHER PUBLICATIONS

Benjamin, Esophageal Foreign Bodies and Food Impactions, Gastroenterology & Hepatology, Aug. 2008, pp. 546-548, vol. 4, Issue 8.

Birk et al., Removal of Foreign Bodies in the Upper Gastrointestinal Tract in Adults: European Society of Gastrointestinal Ensdoscopy (ESGE) Clinical Guideline, Endoscopy 2016, 2016, pp. 1-8.

Hobbs Medical, Inc., Aspiration Catheters, May 22, 2013, http://www.hobbsmedical.com/endoscopy-products-catheters-aspiration-catheter (archived at https://web.archive.org/web/20130522065728/http://www.hobbsmedical.com/endoscopy-products-catheters-aspiration-catheter.htm).

Hobbs Medical, Inc., Aspiration Catheters, Jun. 6, 2019, https://www.hobbsmedical.com/products/aspiration-catheters.

(56) References Cited

OTHER PUBLICATIONS

Kragha, Complete Gastroesophageal Obstruction by Food Bolus, Applied Radiology, Sep. 2016, pp. 40-44.
Shafique et al., New and Safe Treatment of Food Impacted in the Esophagus: A Single Center Experience of 100 Consecutive Cases, Gastroenterology Research and Practice, 2013, pp. 1-4, Hindawi Publishing Corporation, Article ID 142703.
International Searching Authority, International Search Report and Written Opinion of the International Searching Authority in International Application No. PCT/US2018/035507, dated Jul. 31, 2018, 8 pages.
Chen et al., Esophageal Food Impaction: A Homemade Suction Tube Attached to Esophagogastroduodenoscopy for ood Bolus Removal, Journal of the Chinese Medical Association, Dec. 2008, pp. 635-638, vol. 71, No. 12.
Ko et al., Review of Food Bolus Management, Can J Gastroenterol, Oct. 2008, pp. 805-808, vol. 22, No. 10.
International Searching Authority, International Search Report and Written Opinion of the International Searching Authority in International Application No. PCT/US2016/063083, dated Feb. 22, 2017, 15 pages.
United States Patent and Trademark Office, Office Action for U.S. Appl. No. 15/995,105, dated Jul. 17, 2020, 16 pages.
Brazilian Instituto Nacional Da Propriedade Industrial, Search Report and Written Opinion for Brazilian Patent Application No. BR112018011092-2, dated Jun. 17, 2020, 7 pages.
China National Intellectual Property Administration, Notification of First Office Action in Chinese Patent Application No. 201680076552. 8, dated Jun. 1, 2020, 23 pages.
International Searching Authority, International Search Report and Written Opinion of the International Searching Authority for International Application No. PCT/US2019/059475, dated Jan. 14, 2020, 10 pages.
European Patent Office, Communication Pursuant to Article 94(3) EPC for European Application No. 16810172.3, dated Mar. 20, 2020, 5 pages.
U.S. Appl. No. 16/900,614, filed Jun. 12, 2020, 39 pages.
United States Patent and Trademark Office, Office Action issued in U.S. Appl. No. 15/995,105, dated Jun. 6, 2020, 6 pages.
IP Australia, Examination Report No. 1 for Standard Patent Application for Australian Patent Application No. 2016362953, dated Sep. 16, 2020, 5 pages.
Japan Patent Office, Notice of Reasons for Refusal in Japanese Patent Application No. 2018-547254, dated Jan. 5, 2021, 7 pages.
United States Patent and Trademark Office, Office Action dated May 3, 2021 for U.S. Appl. No. 15/995,105, 31 pages.

\* cited by examiner

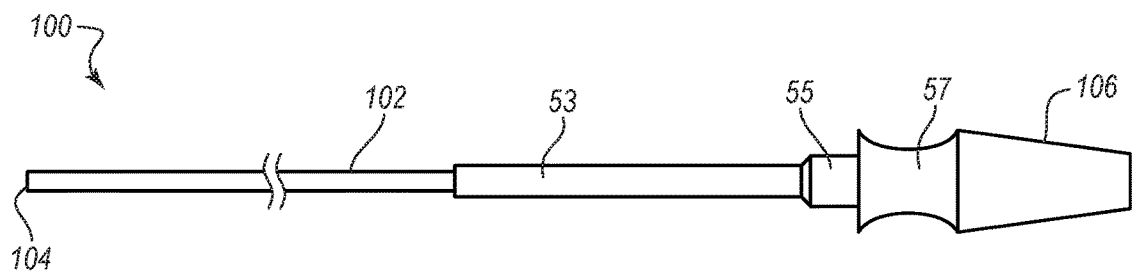
FIG. 1
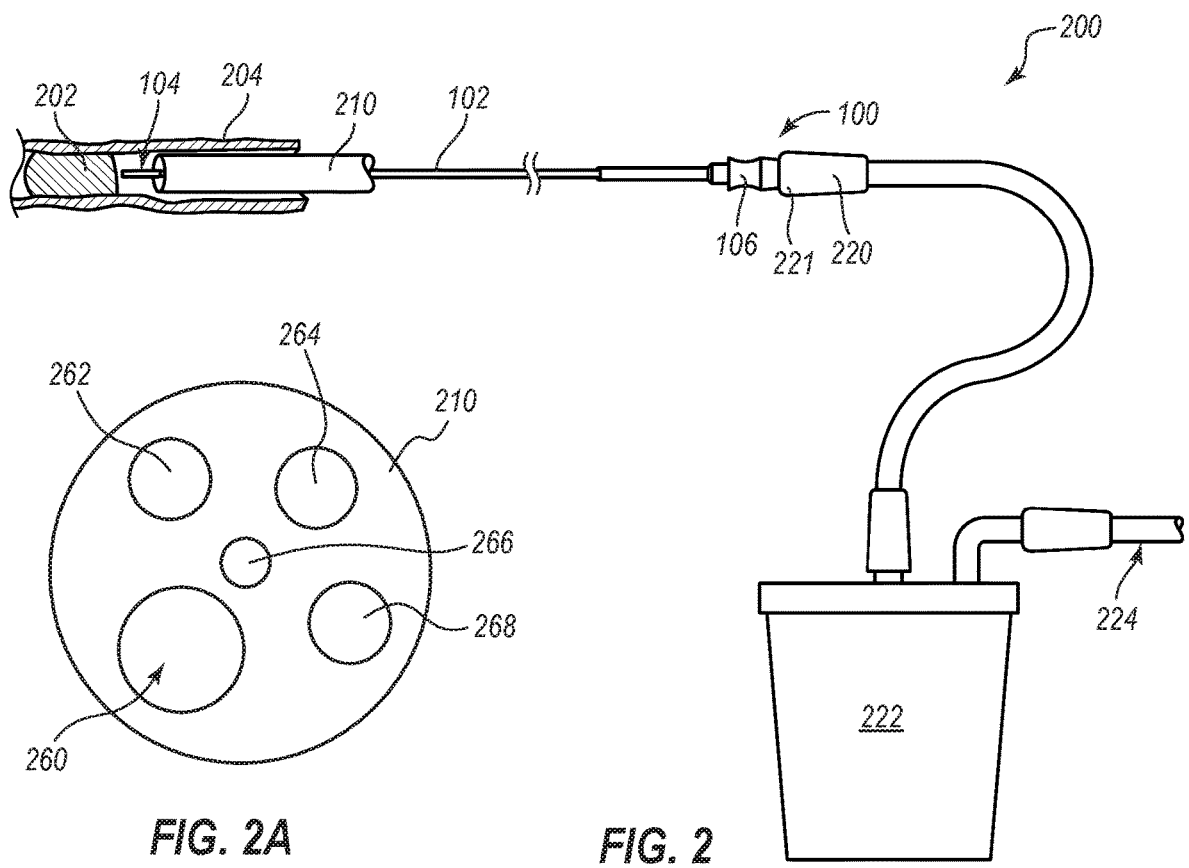
FIG. 2A
FIG. 2
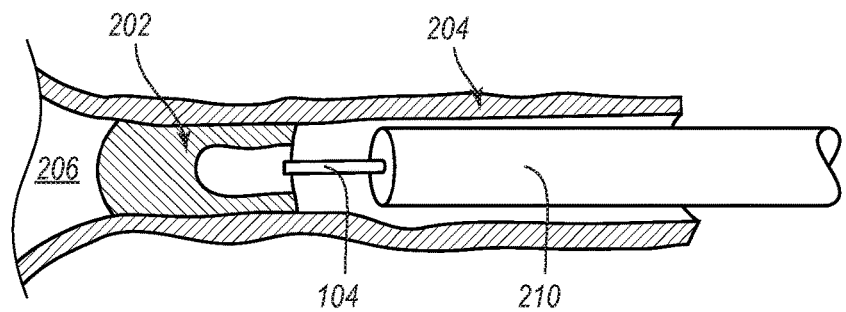
FIG. 3

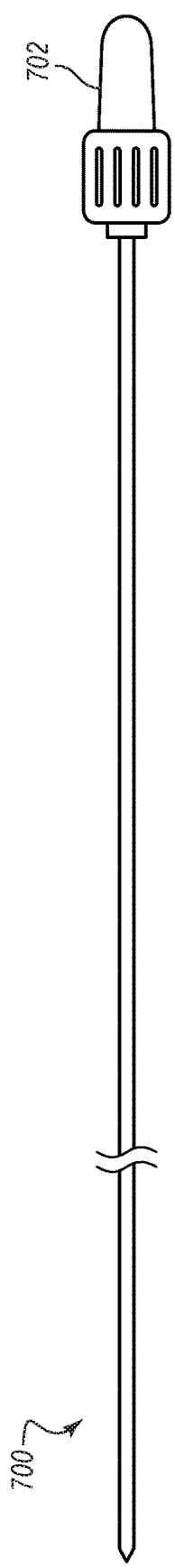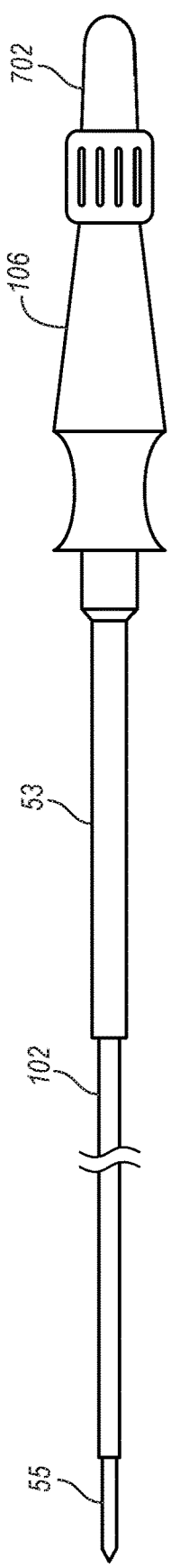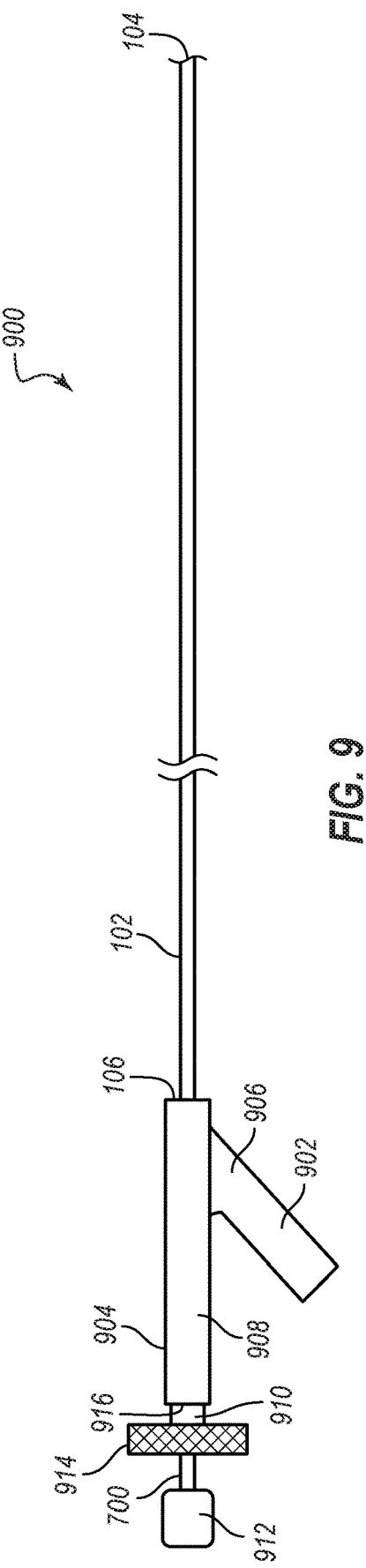

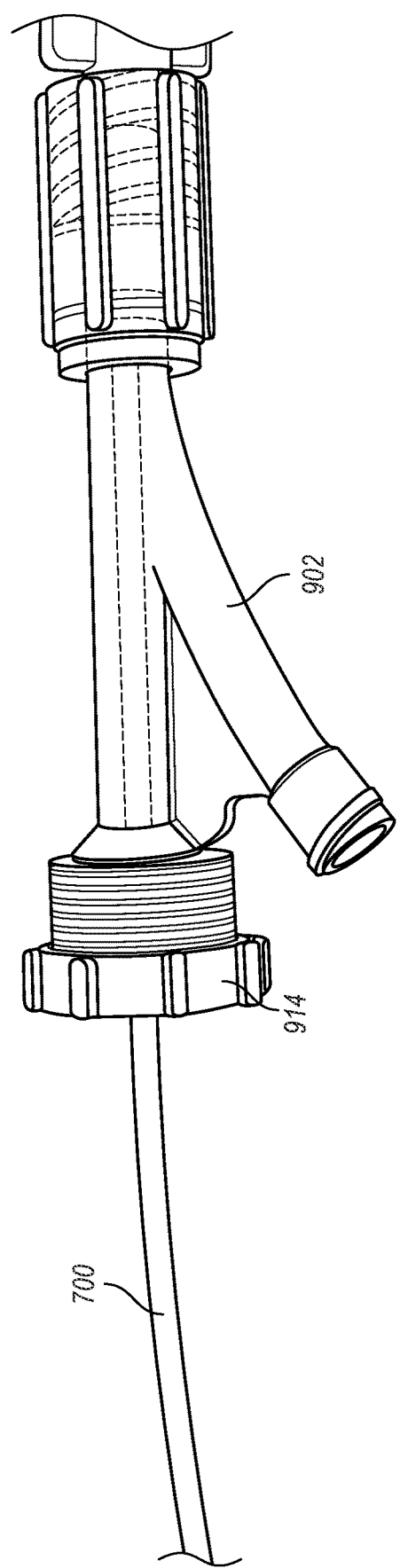

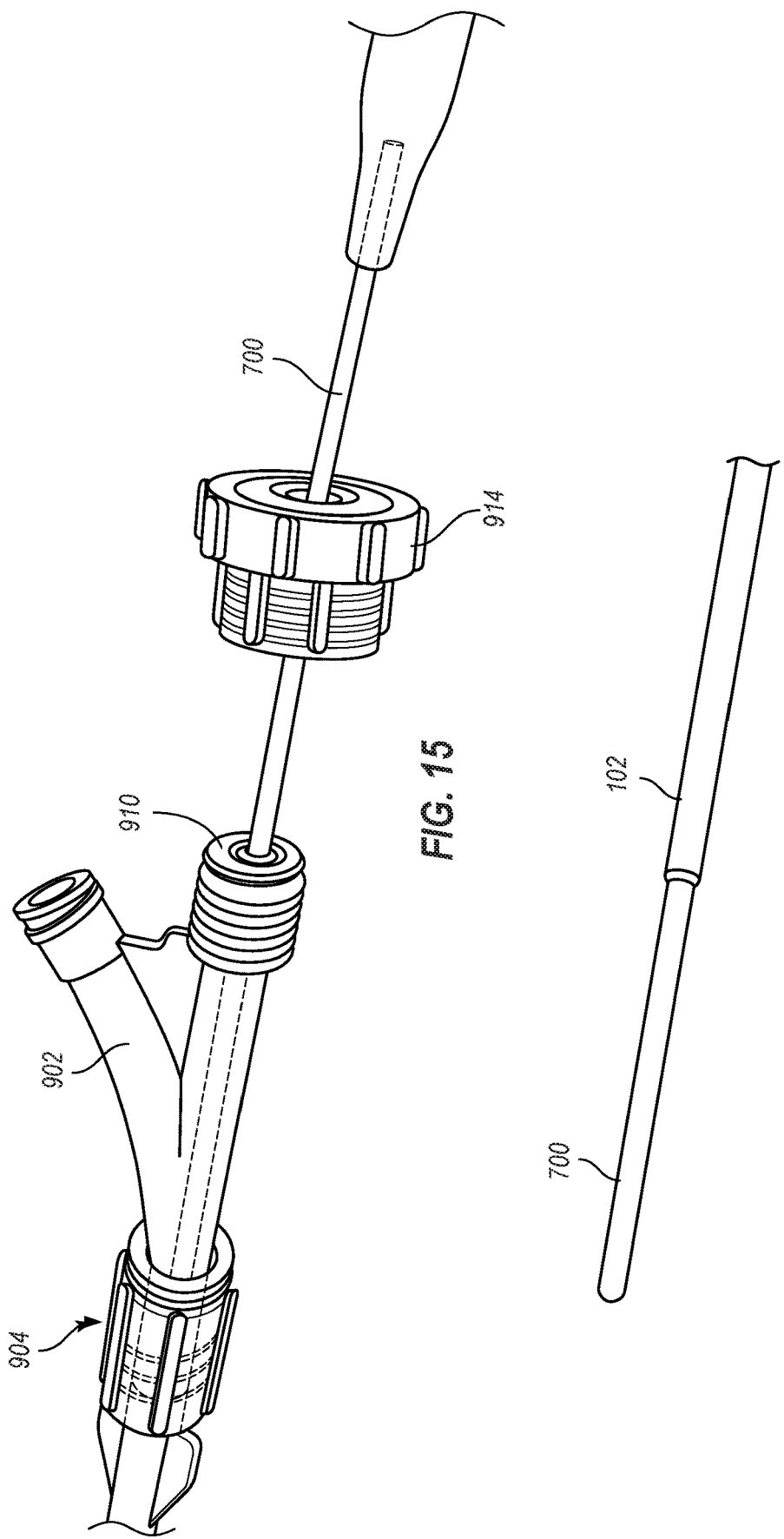

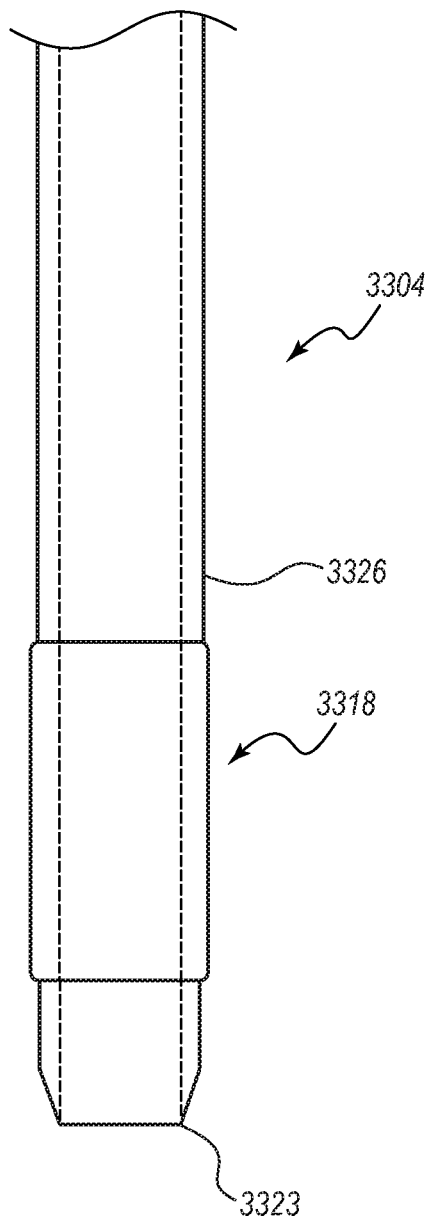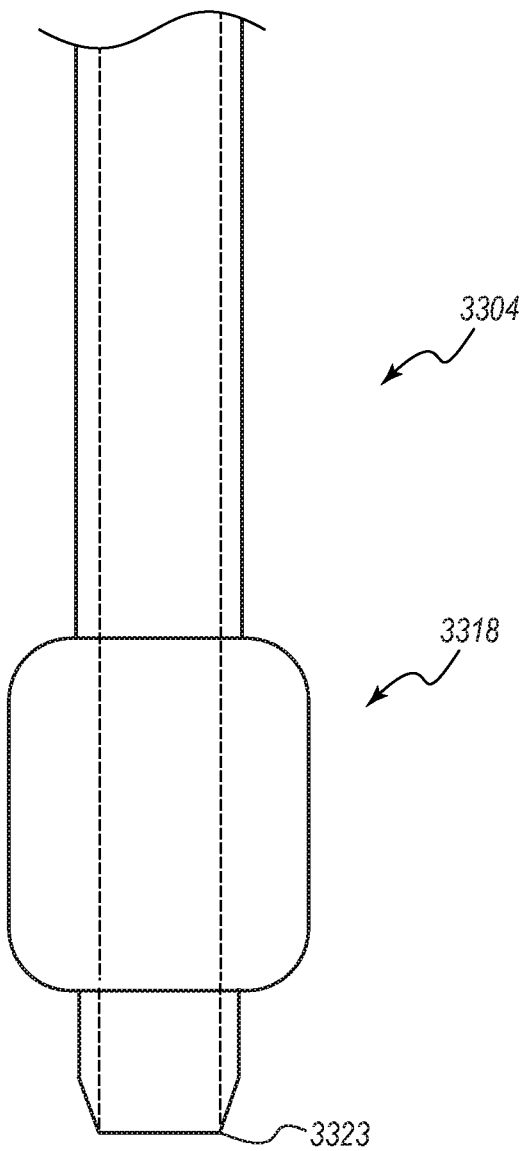
FIG. 38A
FIG. 38B

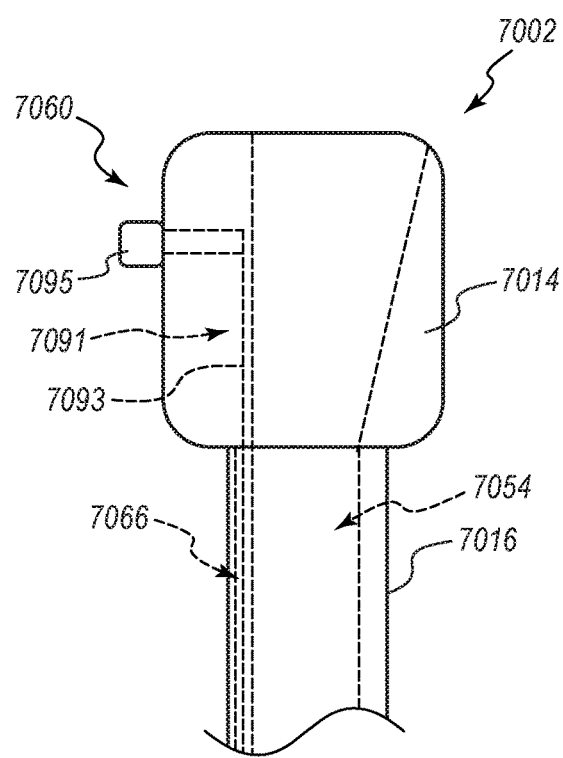
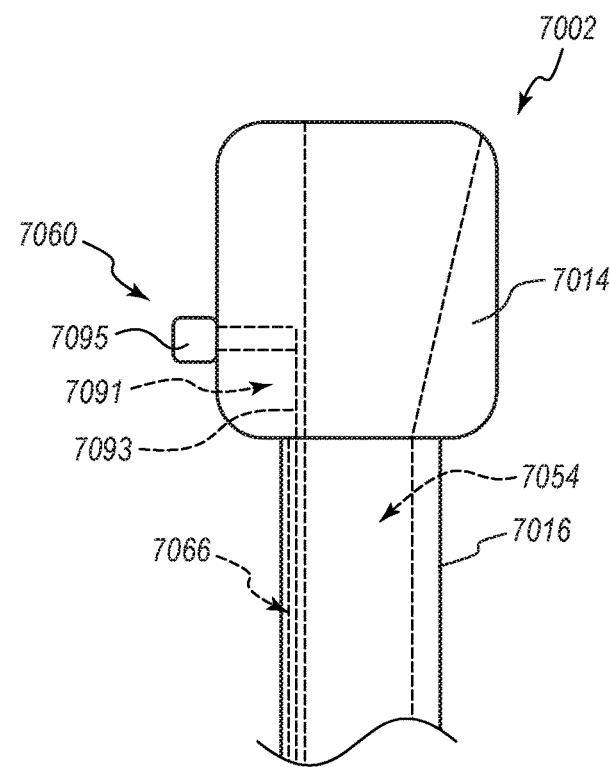
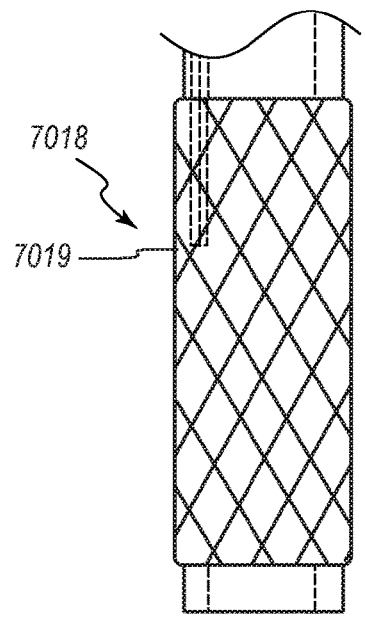
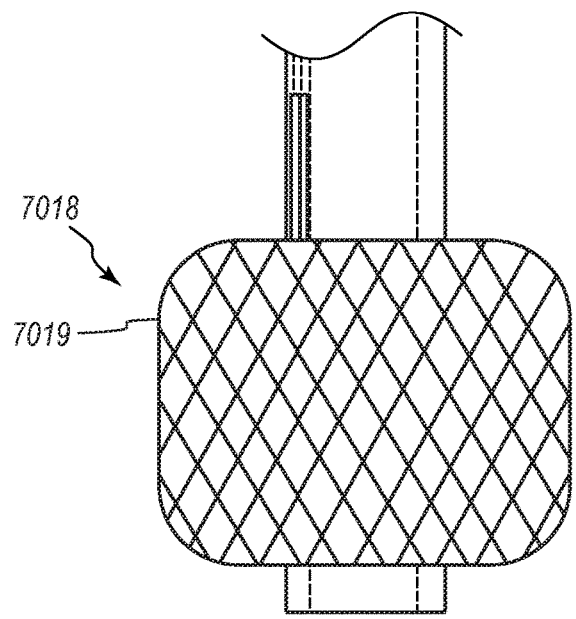
FIG. 57A          FIG. 57B

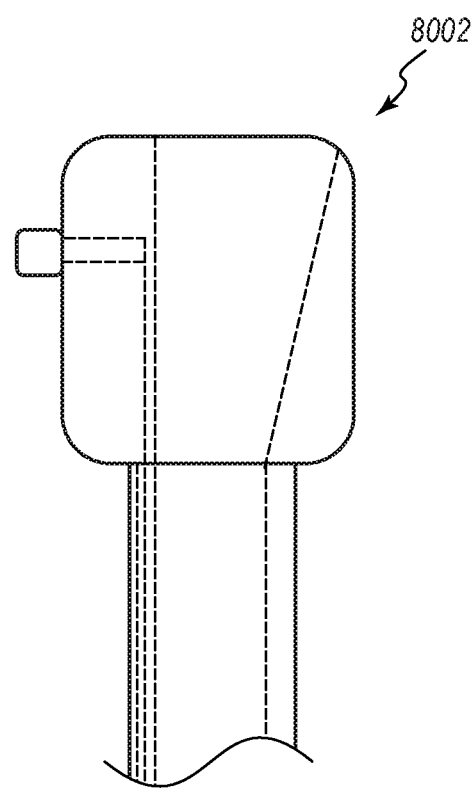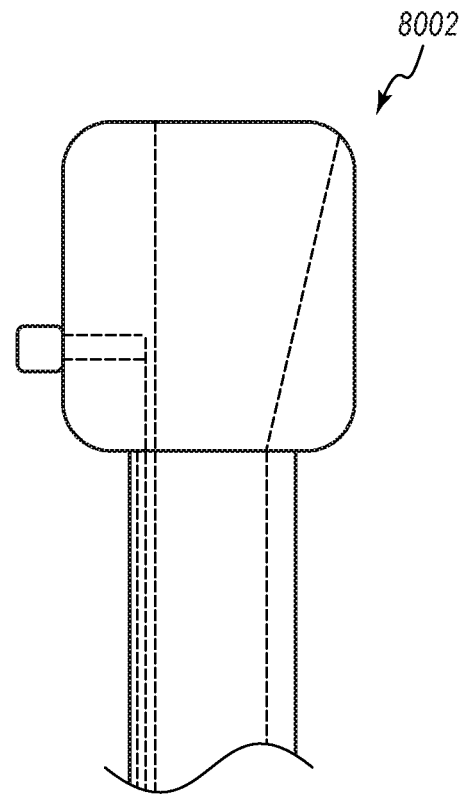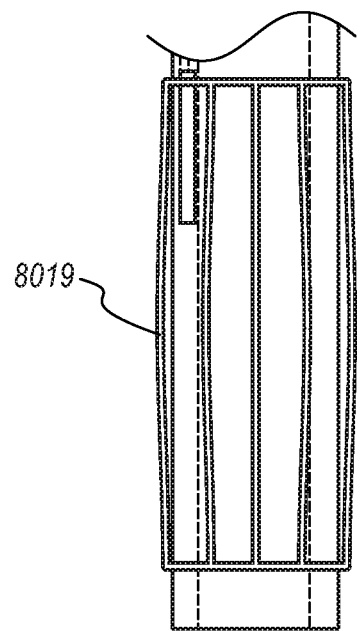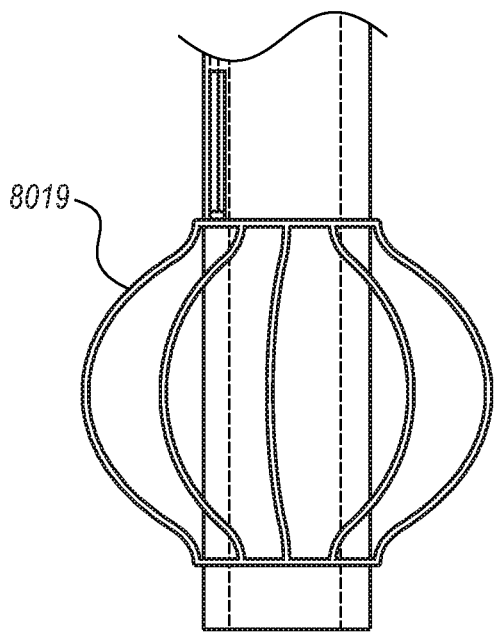
FIG. 58A               FIG. 58B

BLOCKAGE CLEARING DEVICES, SYSTEMS, AND METHODS

CROSS-REFERENCE TO RELATED APPLICATIONS

This application claims the benefit under 35 U.S.C. § 119(e) of U.S. Provisional Patent Application No. 62/513,419, filed on May 31, 2017, titled BLOCKAGE CLEARING DEVICES, SYSTEMS, AND METHODS, and U.S. Provisional Patent Application No. 62/636,526, filed on Feb. 28, 2018, titled BLOCKAGE CLEARING DEVICES, SYSTEMS, AND METHODS; further, pursuant to 35 U.S.C. § 120, this application is a continuation-in-part of prior U.S. patent application Ser. No. 15/356,975, filed on Nov. 21, 2016, titled BLOCKAGE REMOVAL, which claims the benefit of U.S. Provisional Patent Application No. 62/260,873, filed on Nov. 30, 2015, titled TREATING ESOPHAGEAL FOOD IMPACTIONS; the entire contents of each of the foregoing applications are hereby incorporated by reference herein.

TECHNICAL FIELD

Certain embodiments described herein relate generally to devices for treating blockages in patients, and further embodiments relate more particularly to devices, systems, and methods for treating esophageal food impactions in patients.

BACKGROUND

Blockages within the body can take various forms. For example, esophageal food impactions are one of the most common and dangerous emergencies in gastroenterology, with an annual incidence rate of at least $13/100,000$ population (Longstreth, GIE; 2001); moreover, the incidence has been increasing in recent years due to a rise in eosinophilic esophagitis (Desai, GIE; 2005). Food impactions can occur when a bolus of swallowed food becomes lodged in the esophagus and is unable to pass spontaneously into the stomach. This occurs either when the swallowed bolus is too large or when there are diseases of the esophagus that narrow the esophageal lumen, such as GE reflux with a stricture or ring, an esophageal food allergy such as eosinophilic esophagitis with stricture or stenosis of the esophagus, a Schatzki's ring, esophageal webs, or esophageal cancer. Motility disorders of the esophagus typically do not cause impactions.

Food impactions present acutely and dramatically, with patients noting chest pain or pressure, inability to swallow, painful swallowing, a sensation of choking, and neck or throat pain. Retching and vomiting are also common, and patients can also experience breathing problems due to tracheal or airway compression, with stridor, coughing or wheezing being noted. Known devices, systems, and methods for treating food impactions suffer from one or more drawbacks that can be resolved, remedied, ameliorated, or avoided by certain embodiments described herein.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1 depicts a side elevation view of an illustrative embodiment of a catheter for clearing a blockage from within a body of a patient;

FIG. 2 depicts a side elevation view of an illustrative embodiment of a system for clearing a bolus of food or other debris or foreign body lodged within an esophagus of a patient, the system including the catheter of FIG. 1;

FIG. 2A is an end-on plan view of a distal tip of an embodiment of an endoscope that is compatible with the system of FIG. 2;

FIG. 3 depicts a portion of the system of FIG. 2 with the bolus of food or other debris being partially cored;

FIG. 7 depicts a side elevation view of an illustrative embodiment of a stylet that is compatible with the system of FIG. 2;

FIG. 8 depicts a side elevation view of the stylet of FIG. 7 positioned within the catheter of FIG. 1;

FIG. 9 depicts a side elevation view of another embodiment of a catheter having a Y-fitting for removing a bolus of food or other debris lodged within an esophagus;

FIG. 14 shows an enlarged view of the proximal portion of the catheter of FIG. 9;

FIG. 15 shows another view of the proximal portion of the catheter of FIG. 9 with a cap of the suction port removed;

FIG. 16 shows a distal end of the catheter of FIG. 9;

FIG. 38A is an elevation view of a distal end of the catheter assembly of FIG. 36 in which a positioning element is depicted in an undeployed state;

FIG. 38B is another elevation view of the distal end of the catheter assembly in which the positioning element is depicted in a deployed state;

FIG. 57A is an elevation view of another embodiment of a sheath assembly, which can be used with embodiments of systems previously disclosed, the sheath assembly being shown in an undeployed state;

FIG. 57B is another elevation view of the sheath assembly of FIG. 57A shown in a deployed state;

FIG. 58A is an elevation view of another embodiment of a sheath assembly, which can be used with embodiments of systems previously disclosed, the sheath assembly being shown in an undeployed state;

FIG. 58B is another elevation view of the sheath assembly of FIG. 58A shown in a deployed state;

DETAILED DESCRIPTION

Figure 4:
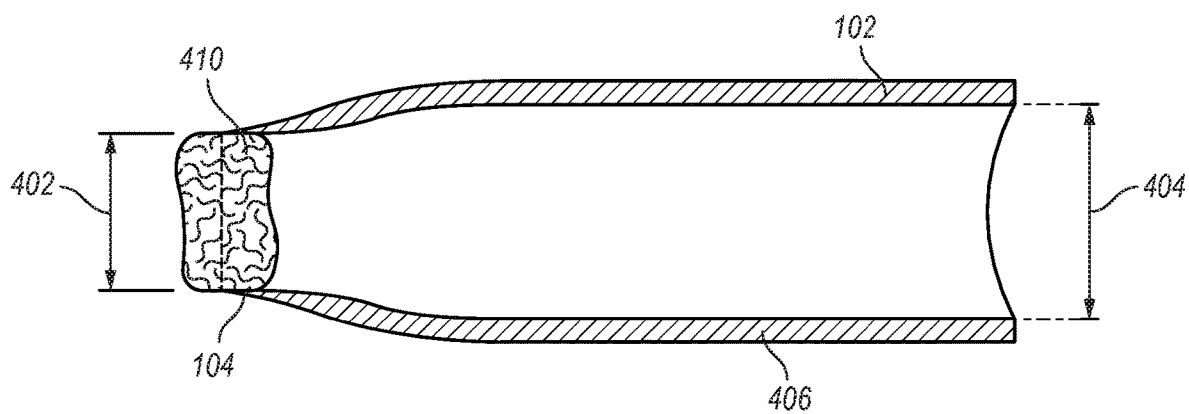
FIG. 4 depicts an illustrative embodiment of a distal end of the catheter for coring the bolus of food or other debris shown in FIG. 1.

The present disclosure relates generally to devices, systems, and methods for addressing a blockage within a lumen of a patient. While specific examples of such devices, systems, and methods are discussed with respect to esophageal food impactions, the disclosure is not limited to this specific application. For example, other foreign bodies positioned within the esophagus and/or blockages within other body lumens may be cleared in manners such as disclosed herein. As a further example, certain embodiments described herein can be used to clear, remove, break up, or otherwise treat other blockages within the body, such as those in the lungs.

Most food impactions clear spontaneously, but a significant fraction (20%) will not and have traditionally required emergent endoscopic intervention to clear the blocked food. This can be dangerous, since typical emergency endoscopy with removal of food can result in serious complications including aspiration pneumonia, laceration of the esophagus with bleeding, or esophageal perforation, which can result in sepsis and death. The complication rate of endoscopic clearance of a food impaction is approximately 3-5% and the mortality rate is unknown but several deaths have been reported (Simic, Am J Forensic Med Path; 1988).

Various endoscopic tools may be used to clear impactions, but all have flaws and there is no prior technique that is demonstrably better than any other. Food can sometimes be pushed blindly through the esophagus and into the stomach using the tip of the endoscope, but this technique is performed without vision of the more distal esophagus, so the endoscopist cannot observe, via the endoscope, what the esophagus looks like distal to the obstruction or what abnormalities exist. This technique can work well in some patients (Vicari, GIE; 2001), but because the technique is blind, can often result in esophageal laceration or perforation. Indeed, there is a significant risk the distal tip of the endoscope and/or a sharp surface within the bolus will be deflected toward the esophagus wall during blind pushing of this sort, resulting in laceration or perforation. Many endoscopists avoid blind pushing for this reason.

Some endoscopic techniques employ forceps that include "rat-tooth" type designs, snares, or variable wire basket designs to break up food into smaller 1s for extraction. Such techniques are laborious, time-consuming, and often fail.

Other extraction techniques can also be tried, particularly when the food bolus is not tightly wedged and is firm, or if the food contains bone or sharp surfaces. In this regard, baskets, snares, graspers, "pelican" forceps with longer arms, nets, etc., can be used to remove food in whole or in pieces, but these techniques also frequently fail, and the patient is at risk for aspiration pneumonia if the pieces fall into the hypopharynx or mouth during the extraction attempts. If the food bolus is lodged proximally, then most of the above techniques will fail or are too dangerous to try. Endoscopic suction cannot be used for impactions, since a food bolus cannot be effectively suctioned through an endoscope. Moreover, if suction is used in an attempt to hold the food bolus against a distal tip of the endoscope, and the suction fails at some point to hold a bolus against the tip of the scope, the patient is at high risk for aspiration as the scope is withdrawn through the hypopharynx or mouth. Overtubes for endoscopes can be used if repeated endoscopic intubation is needed, but overtubes are uncomfortable, require deeper sedation, and can be dangerous in and of themselves with risk of esophageal laceration and perforation.

Certain embodiments disclosed herein can resolve, remedy, ameliorate, and/or avoid one or more of the limitations of known techniques for treating a patient who suffers from an esophageal food impaction, such as those just described, and/or can be advantageous over such techniques for other reasons, as will be apparent from the present disclosure.

In certain embodiments, a device is configured to clear a bolus of food impacted within an esophagus. The device can include a catheter tube having a hollow interior and a distal end configured to core the bolus of food and can include a proximal end configured to be coupled to a source of suction to clear the core. Certain systems described herein assist in resolving the buildup of pieces of food in the esophagus while minimizing the risk of aspiration. The systems are further designed in an atraumatic manner, helping to avoid esophageal laceration and perforation. In some embodiments, an inner region of a food impaction that is spaced from the esophageal wall (e.g., the mid-region or center of the food impaction) is cored out.

For example, in one embodiment, the system includes a catheter (e.g., hollow tube) with a distal end that is delivered to the site of the blockage. The distal end of the catheter is used to core out portions of the blockage until the blockage is reduced in volume in a piecemeal manner. The smaller volume blockage can then pass through the esophagus spontaneously and/or be more easily removed. In some embodiments, the catheter can be delivered to the blockage site through an endoscope (e.g., through the instrument channel of the endoscope) or other similar device.

In other or further embodiments, the catheter can be delivered to the blockage site through a dedicated or specialized sheath, which may include a positioning element to prevent the catheter tip from contacting the esophageal wall. In some instances, the dedicated sheath may permit the catheter to define a larger internal lumen, as compared with catheters that are deployed through the instrument or working channel of a standard endoscope, which can facilitate and/or increase a rate of blockage clearance. The dedicated sheath may permit the catheter to be used in a blind procedure, such as in an emergency room setting, without endoscopic or other visualization of the impaction during the procedure. In some embodiments, the sheath includes a positioning element that spaces the distal tip of the catheter away from the esophageal wall to prevent laceration or perforation of the esophagus.

In still other or further embodiments, the catheter itself may include a positioning element to prevent the catheter tip from contacting the esophageal wall. In some instances, the catheter may be used without an endoscope or other sheathing element.

In certain examples, suction can be provided to remove the cored portions of the blockage. The suction can be provided at the proximal end of the catheter to assist with the coring and/or to cause the cored portions to be suctioned from the site of the blockage and passed through the catheter and discarded, thus minimizing a risk of food aspiration. In some instances, suctioning arrangements can preserve endoscopic visualization. Stated otherwise, a coring aspiration catheter may be deployed through the working channel of an endoscope to remove portions of a food bolus without blocking a viewing lens at a distal end of the endoscope and/or without obscuring, or without significantly or fully obscuring, a field of view of the lens. For example, the impacted food bolus and the coring aspiration catheter may be viewed via the viewing lens at the distal end of the endoscope throughout at least a portion of the clearing procedure.

Certain embodiments can include features that allow cored portions of the food to be cleared, should the portions become caught in the catheter while being suctioned away from the blockage site. In one example, a source of compressed air, such as a syringe, can be placed at the proximal end of the catheter, and air can be passed through the catheter to clear any portions caught in the catheter, via the distal end. In other or further embodiments, a stylet can be passed through the interior of the catheter to clear any portions of food caught therein. The stylet can also perform other or further functions, such as providing stiffness for the catheter during delivery of the catheter to the blockage site. Further, the stylet can be configured to assist in the manipulation of the blockage, such as by advancing the stylet into the blockage one or multiple times to create a nidus for coring and suctioning.

One or more of the foregoing advantages and/or one or more other or further advantages will be apparent from the discussion that follows.

Referring now to FIG. 1, an example catheter 100, which may also be referred to as a catheter assembly 100, is shown. The catheter 100 includes a hollow catheter tube 102 that generally can be used to core out a portion of a blockage. Specifically, the catheter tube 102 includes a distal end 104 that is configured to contact and core the blockage one or more times. As the blockage is cored by the distal end 104 of the catheter tube 102, the volume of the blockage is reduced until the blockage is able to be passed through the esophagus spontaneously and/or removed.

The catheter assembly 100 includes a proximal end 106 configured to be coupled to various devices. For example, as described further below, the proximal end 106 of the catheter assembly 100 is configured to be coupled to a source of suction to allow the cored food portions to be suctioned and/or removed through the catheter tube 102. In another example, the proximal end 106 of the catheter tube 102 is configured to be coupled to a source of pressurized air, such as a syringe, to allow any cored food stuck within the catheter tube 102 to be cleared. Other configurations are possible. In the illustrated embodiment, the proximal end 106 is formed as a tapered connector that can be directly connected to a standard vacuum tubing arrangement, such as in a hospital setting, as discussed further below with respect to FIG. 2.

The catheter or catheter assembly 100 can include a strain relief sleeve 53 of any suitable variety. The strain relief sleeve 53 can inhibit kinking or other undesirable deformation of the catheter tube 102 during use of the catheter tube 102. In some embodiments, the catheter 100 includes a shoulder 55 at a proximal end of the strain relief sleeve 53. The shoulder can define a larger diameter than the strain relief sleeve 53. The catheter 100 can further include a handle 57 via which a user may manipulate the proximal end of the catheter 100.

Referring now to FIGS. 2 and 3, the catheter 100 is shown within an example system 200 configured to remove a blockage 202 positioned within an esophagus 204 of a patient. In this example, the blockage 202 (generally food or other debris, but could also be other blockages like blood or blood clots, mucus, etc.) has become caught within the esophagus 204.

In the embodiment shown, the catheter 100 is delivered to the blockage 202 using an endoscope 210. The endoscope 210 can be of any suitable variety, including those presently in use and/or those yet to be devised. For example, the endoscope can be any of a variety of standard endoscopes typically used for upper GI tract endoscopy. As shown in FIG. 2A, the endoscope 210 contains a working channel 260 that is generally hollow and allows the catheter 100 to be delivered through the endoscope 210 to the blockage 202. The endoscope 210 may generally be referred to as a tubular member that defines a channel—specifically, the working channel 260.

In various embodiments, the endoscope 210 can include one or more additional ports having a variety of additional functions. For example, in the illustrated embodiment, the endoscope 210 includes a viewing port 262, which may include a lens, via which a region beyond the distal tip of the endoscope 210 can be viewed. The endoscope 210 can further include a light guide that terminates at a light port 264 for illuminating the region beyond the distal tip of the endoscope 210. The endoscope 210 can include a water jet 266 and/or can include an air and/or water nozzle 268. Various embodiments of endoscopes can include more or fewer features.

With continued reference to FIGS. 2 and 3, once the distal end 104 of the catheter tube 102 is in position, the endoscope 210 can be withdrawn or can remain in place as the blockage 202 is manipulated. In many methods, the endoscope 210 remains in close proximity to the blockage 202 during coring via the catheter tube 102 to permit visualization of the coring. In particular, the endoscope 210 can be positioned such that the region that is illuminated by the light port 264 and that is within the field of view of the lens of the viewing port 262 includes both the proximal end of the blockage 202 and the distal end of the catheter tube 102 as the catheter tube 102 is used to core pieces out of the blockage 202.

The catheter tube 102 of the catheter 100 is configured to be advanced so that the distal end 104 impacts the blockage 202 so as to reduce the volume of the blockage 202, such as by repetitively coring the food. As the volume is reduced (such as is shown in FIG. 3), the blockage 202 can be naturally passed through the esophagus 204 and into a stomach 206 of the person.

In example embodiments, the catheter tube 102 is at least semi-rigid but flexible, which allows the catheter tube to flex and/or bend during delivery through the endoscope, as the endoscope flexes and bends. This allows the catheter tube 102 to be directed more precisely as it is inserted to a desired location. For example, in some instances, the endoscope is introduced into the patient through the nose of the patient—or stated otherwise, is introduced into the patient via transnasal endoscopy—such that the endoscope defines a curved route through the upper respiratory tract of the patient. In other instances, the endoscope is introduced into the patient through the mouth, such that the endoscope defines a curved route from the mouth to the esophagus, in manners such as described elsewhere herein. The catheter tube 102 may be sufficiently flexible to pass through the curved portion of the endoscope, or more specifically, pass through the curved portion of the working channel 260.

In some examples, the distal end 104 of the catheter tube 102 is configured to assist in the coring of the blockage 202. For example, as shown in FIG. 4, the distal end 104 of the catheter tube 102 is tapered. Specifically, the distal end 104 includes an inner diameter 402 that is smaller than an inner diameter 404 of a more proximal portion 406 of the catheter tube 102. In one example, the difference in diameters can be less than one-hundredth of a millimeter. Other sizes are possible. In addition, the walls of the catheter tube 102 can be thinned as the walls extend to the distal end 104, as depicted.

This tapering of the distal end 104 can allow a core 410 of the blockage 202 that is formed by the distal end 104 to be more easily suctioned through the catheter tube 102. Since the cores formed by the distal end 104 will typically have a diameter smaller than that of the portion 406, the cores can be more easily suctioned through the catheter tube 102 for evacuation, as is illustrated by Poiseuille's law.

Figure 5:
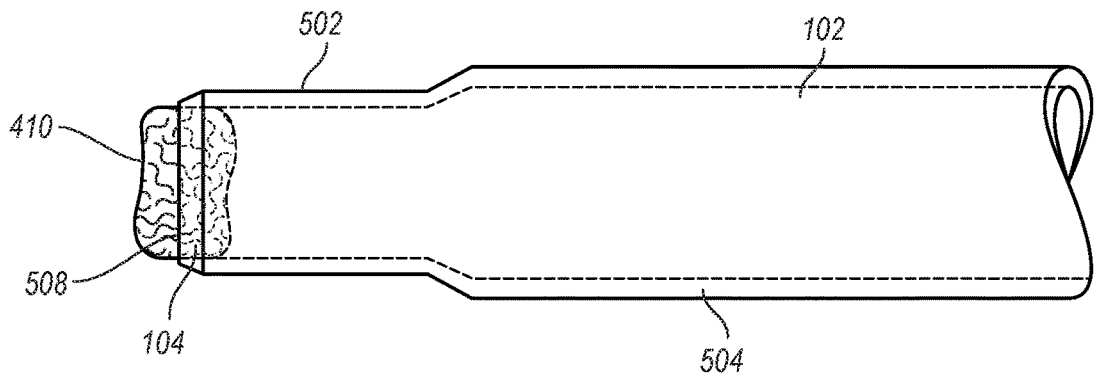
FIG. 5 depicts another illustrative embodiment of a distal end of a catheter for coring the bolus of food or other debris, such as that shown in FIG. 1.

In another depiction shown in FIG. 5, the catheter tube 102 is formed of a first portion 502 at the distal end 104 having a smaller diameter, and a second portion 504 extending along a remainder of the catheter tube 102 having a larger diameter. This again allows the cores of the blockage 202 that are created by the first portion 502 to be smaller in diameter so that the cores can more easily pass through the remainder of the catheter tube 102 (i.e., the second portion 504).

In some examples, a tip 508 of the distal end 104 of the catheter tube 102 can be beveled and/or serrated. The tip 508 can take multiple forms, including a serrated edge, to cut (e.g., saw) or shave bits of the blockage 202 off of the bolus to better aid suctioning. The tip 508 can help core the blockage. For example, in some instances, the catheter tube 102 may be rotated relative to the working channel of the endoscope, whether in a single direction or back and forth, as the tip 508 contact the blockage 202. In some instances, this rotation, coupled with a serrated or otherwise configured tip can assist in coring the blockage 202. This technique may be used with other embodiments as well, including those in which a catheter is inserted through a sheath assembly, rather than an endoscope.

For example, referring again to the system 200 depicted in FIG. 2, a source of suction can be applied to the proximal end 106 of the catheter 100 to allow the cores of the blockage 202 to be removed through the catheter tube 102. Specifically, in the example provided, a vacuum line 220 can be coupled to the proximal end 106 of the catheter tube 102. In particular, the vacuum line 220 can include a suction line fitting 221 that is connected to the proximal end 106 of the catheter 100. The vacuum line 220 can be coupled to a collection canister 222 of any suitable variety, including those presently known or those yet to be devised, and the collection canister 222 is coupled to a suction line 224. The suction line 224 is coupled to a source of suction, such as a hospital vacuum source. In this configuration, pieces of the blockage 202 that are cored or otherwise dislodged by the catheter tube 102 can thereupon be sucked up the catheter tube 102, through the vacuum line 220, and collected in the collection canister 222.

As described previously, it is possible for one or more cores of the blockage 202 to become stuck within the catheter tube 102. In such a scenario, various devices can be used to clear the stuck cores.

Figure 6:
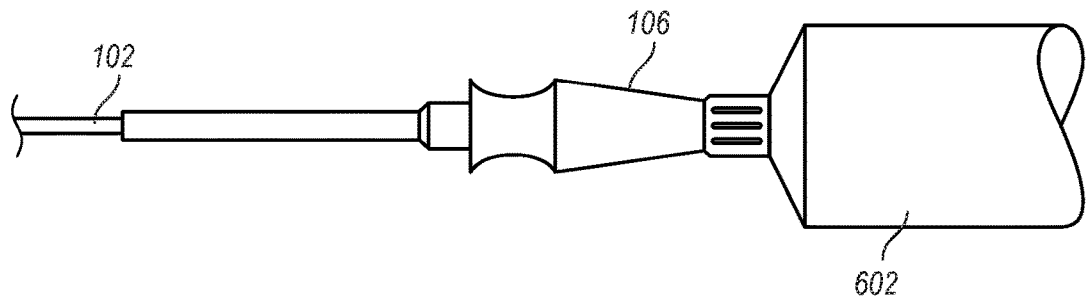
FIG. 6 depicts an illustrative embodiment of a proximal end of a catheter tube of FIG. 1 coupled to an embodiment of a syringe.
Figure 10:
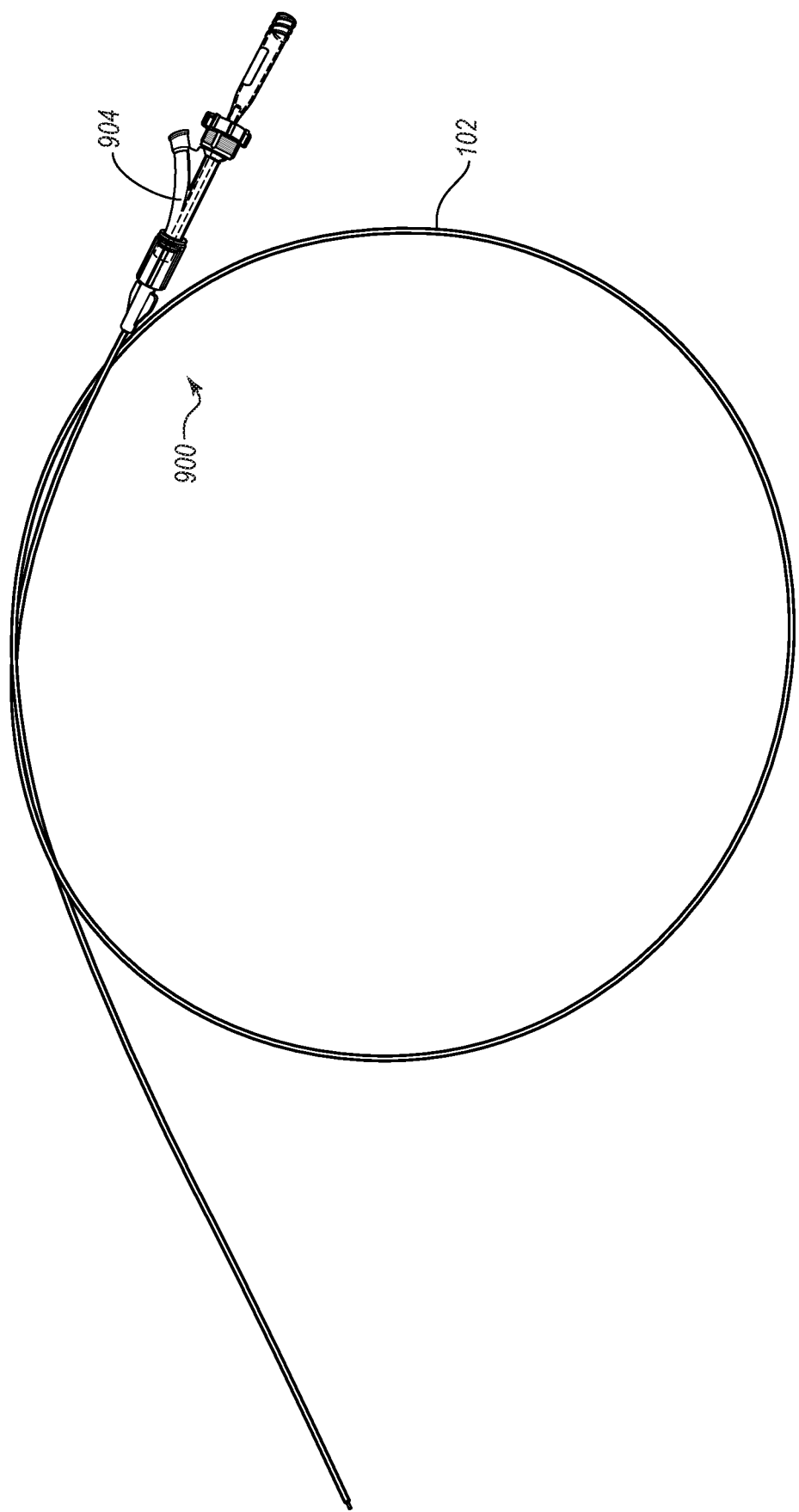
FIG. 10 is a perspective view of the catheter of FIG. 9.
Figure 11:
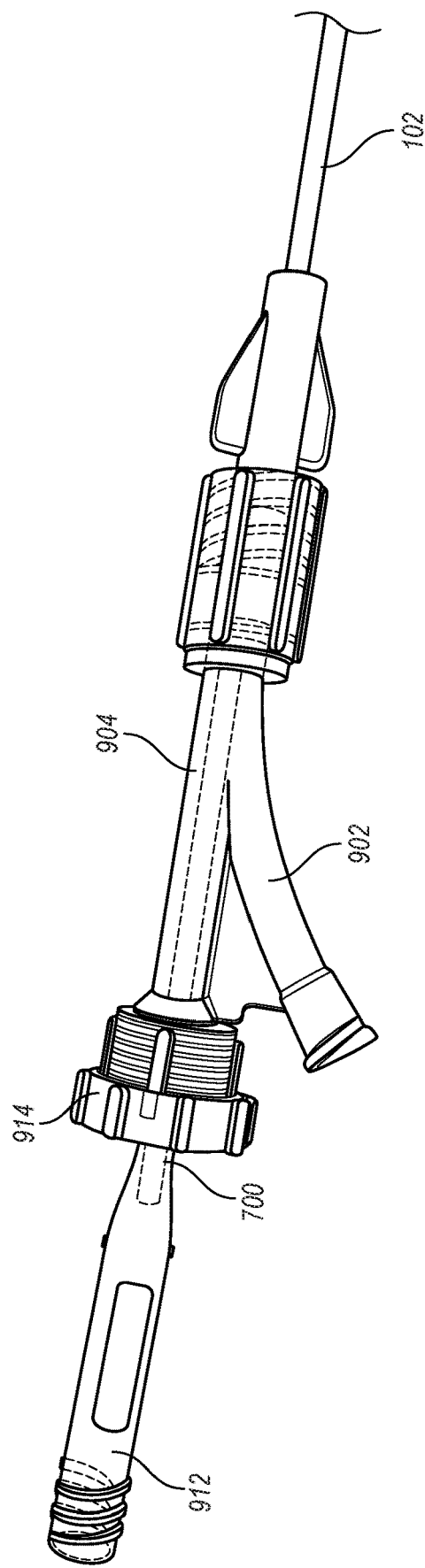
FIG. 11 is a perspective view of a proximal portion of the catheter of FIG. 9 with a stylet advanced fully therethrough.
Figure 12:
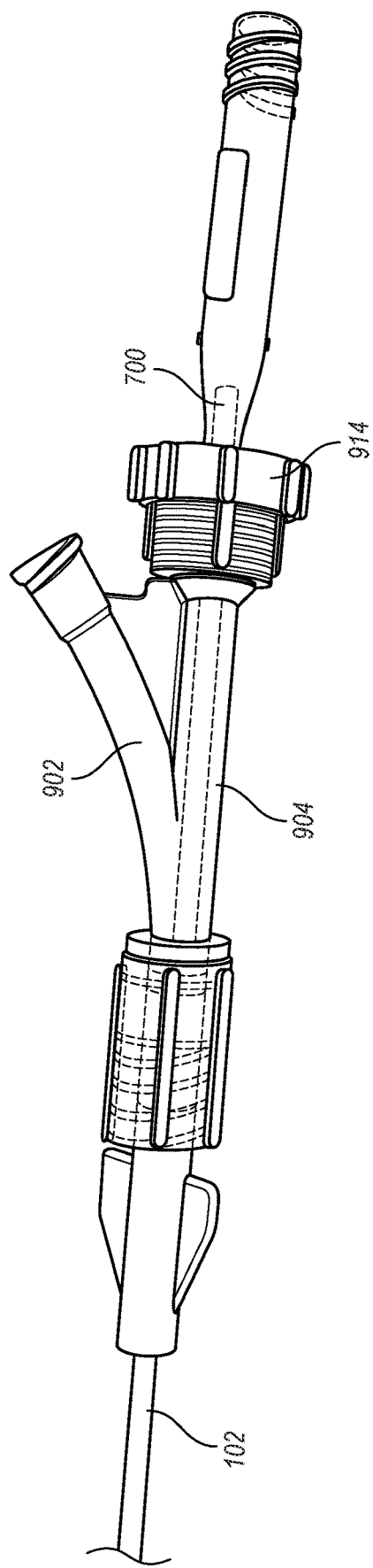
FIG. 12 shows another perspective view of the proximal portion of the catheter of FIG. 9.
Figure 13:
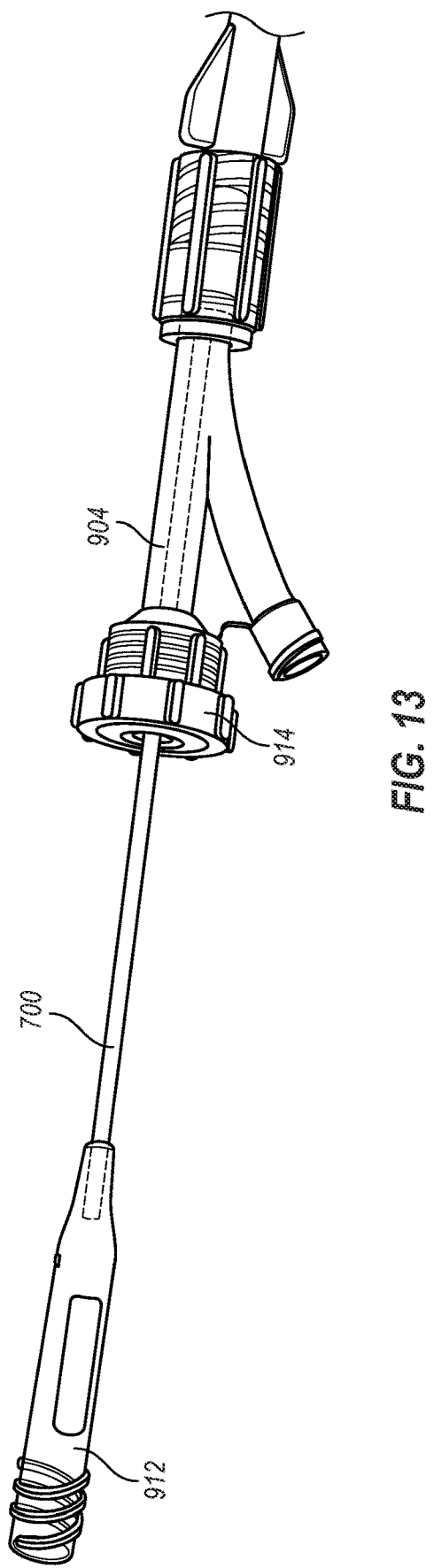
FIG. 13 shows another view of the proximal portion of the catheter of FIG. 9 with the stylet partially removed therefrom.
Figure 17:
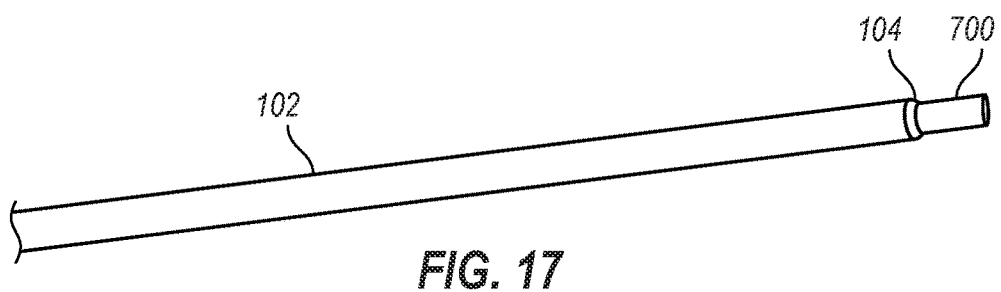
FIG. 17 shows the distal end of the catheter of FIG. 9.

For example, referring now to FIG. 6, an example syringe 602 is coupled to the proximal end 106 of the catheter 100 using, for example, a suction line fitting or Luer-lock style connection. In this embodiment, the syringe 602 can be a typical 60 cc syringe that is used to deliver air into the catheter tube 102 during coring of the blockage 202 to dislodge and/or remove portions of the blockage 202 that are in the catheter tube 102.

In this instance, a plunger of the syringe 602 is actuated to displace air within the syringe 602 into and through the catheter tube 102. This air can be used to dislodge obstructions within the tube. Other configurations are possible. For example, other types of fluids, such as a jet spray of water, could be used to help clear the tube or break up food.

In other instances, different devices can be used to clear the catheter 100. For example, referring now to FIG. 7-8, a stylet 700 is shown that is sized to fit through the hollow interior of the catheter tube 102. Generally, the stylet 700 can be used to perform various functions.

For example, the stylet 700 can be used to stiffen the catheter 100 during delivery to the blockage 202. Further, the stylet 700 can be introduced through the catheter tube 102 to clear the catheter tube 102 when one or more cores get stuck, performing a function of a pusher rod. In other or further instances, the stylet 700 can be used to pierce the blockage 202 to start a nidus for coring and suctioning. In various examples, the stylet 700 can be solid or hollow.

In the illustrated example, the stylet 700 further includes a stylet knob 702 that is configured to be engaged with the proximal end 106 of the catheter 100. The proximal end 106 can be configured to include a Luer taper that allows the proximal end 106 to engage the stylet knob 702 of the stylet 700. Other coupling arrangements, such as a threaded engagement, for example, can be used.

As shown in FIG. 8, the stylet knob 702 is coupled to the proximal end 106 of the catheter tube 102. In this configuration, the catheter 100 can be delivered to the desired location within the esophagus 204. At that time, the stylet knob 702 can be disengaged from the proximal end 106 to free the stylet 700 for movement. This movement can include the caregiver pushing the stylet 700 into and out of the catheter tube 102 to generally disrupt the blockage 202 and/or removal of the stylet 700 completely from the catheter tube 102.

When the stylet 700 is removed from the catheter tube 102, the vacuum line 220 can be connected to the proximal end 106 of the catheter tube 102 for suctioning, as described previously.

In this example shown in FIG. 8, the catheter tube 102 is approximately 80.5 inches in length and the stylet 700 is approximately 84 inches in length, although many different lengths can be provided such as, for example, shorter lengths for children and longer lengths for adults or to accommodate different length endoscopes, bronchoscopes or colonoscopes. The example catheter tube 102 has an outer diameter of 0.135 inches and an inner diameter of 0.115 inches. The stylet 700 has an outer diameter of 0.105 inches. Other sizes can be used.

In other embodiments, the catheter tube 102 can be variable in length and diameter, or stated otherwise, a variety of lengths and diameters are contemplated. For example, another embodiment of the catheter tube 102 measures 0.093 inches in outer diameter and 0.082 for the inner diameter, allowing for easy introduction and sliding within the working channel of any of a variety of endoscopes. The catheter tube 102 is long enough to extend through an endoscope. In some embodiments, the catheter tube 102 is at least 120 cm in length, but it can be longer in other embodiments.

The stylet 700 can vary in diameter, but in the preferred embodiment measures 0.070 inches in outer diameter to allow easy introduction and sliding within the catheter tube 102, and is slightly longer than the catheter tube 102 to allow the stylet 700 to extend beyond the distal end 104 of the catheter tube 102 to clear the catheter tube 102 and extend further into the blockage 202, if desired.

The catheter tube 102 can be made from a thin-walled extruded tube sized to fit the working channel (e.g., biopsy channel) of any commercially available endoscope. One example material is PEBAX® 7233 SA, available from Arkema, or any other suitable thermoplastic elastomer. Another possible material is an extrusion grade of PETG (glycol-modified polyethylene terephthalate). Other suitable materials include polyamide or extrusion grade Nylon or DELRIN® (acetal homopolymer resin, an engineering thermoplastic, available from DuPont), such as Nylon 10 or Nylon 12.

The stylet 700 could be made of the same or similar material. For example, the catheter tube 102 and the stylet 700 can be made of the same material to allow the stylet 700 to fit within the catheter tube 102 while minimizing friction. However, other materials and different materials for each can be used.

The above materials would clear food, but would not seriously damage the walls of the esophagus should they inadvertently contact the walls of the esophagus.

Referring now to FIGS. 9-17, another example device 900 is shown. The device 900 includes the catheter tube 102 with a suction port 902 at the proximal end 106 and with the distal end 104 that is designed (e.g., beveled) to be advanced through the biopsy channel of any commercial endoscope and that can accommodate the stylet 700 to clear any food that may stick in the catheter tube 102 after removal from the esophagus.

As shown in FIG. 9, the catheter tube 102 is designed to fit through the biopsy channel of an endoscope positioned within the esophagus to reach a food blockage, but can also be advanced adjacent to an endoscope and can also be advanced orally without the aid of an endoscope. The catheter tube 102 is also bendable and maneuverable as the endoscope bends and maneuvers, yet is rigid enough to withstand kinking. The catheter tube 102 is also sufficiently rigid to withstand suction forces that are sufficient to remove cored portions of a food or other blockage through the lumen of the catheter tube 102.

In this example (see FIGS. 9 and 15), there is a Y-fitting 904 wherein one arm 906 of the Y is attached to and forms the suction port 902, and another arm 908 of the Y accommodates the stylet 700.

There is also a compression seal 910, or rubber stopper, at the proximal end of the arm 908 that accommodates the stylet 700, so that any air escaping the proximal end—or entering through the proximal end—is minimized when the stylet 700 is in the catheter tube 102, so that suction and stylet clearance of the vacuum tube can occur simultaneously. When the compression seal 910 is loosened, the stylet 700 can be easily advanced into and out of the catheter tube 102 using a handle 912 of the stylet 700. The compression seal 910 can also secure the stylet 700 in any location along the shaft of the catheter tube 102.

In this example, a cap 914 is threaded onto the proximal end 916 of the arm 908 to retain the compression seal 910 in place. Upon removal of the stylet 700 from the catheter tube 102, the compression seal 910 is configured, in some embodiments, to close the proximal end 916 so that suction can be performed through the catheter tube 102 and the suction port 902.

In the example shown, the catheter tube 102 can work with the stylet 700 completely removed; the stylet 700 can also be introduced as needed, and advanced any distance in the catheter tube 102.

As with previous embodiments, the distal end 104 of the catheter tube 102 can disrupt food, core food, shave food and suction food. The catheter tube 102 wall could be thin and rigid to better accommodate a larger lumen of the tube. The stylet 700 can help support the catheter tube 102 to help prevent kinking, in some embodiments. Thus, in some instances, the stylet 700 can both help clear the suction tube and act as a stylet to stiffen the catheter tube 102.

Figure 18:
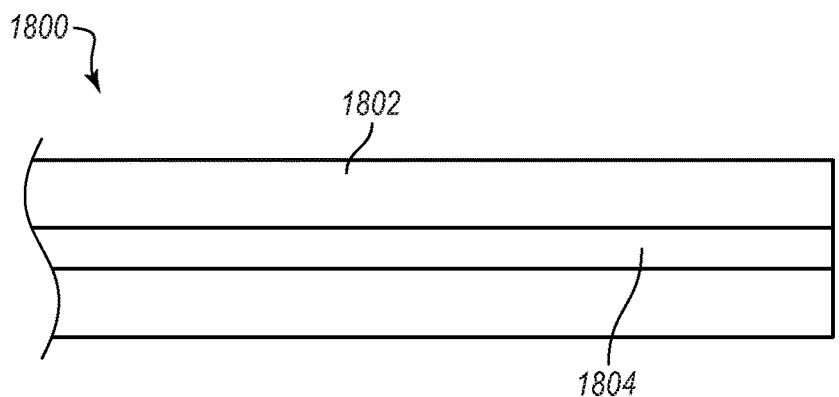
FIG. 18 shows another example embodiment of a stylet for removing a bolus of food or other debris lodged within an esophagus.
Figure 19:
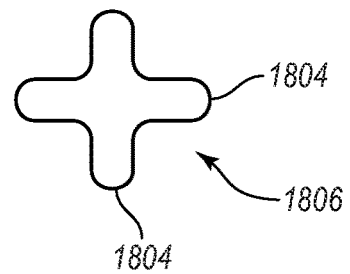
FIG. 19 shows an end portion of the stylet of FIG. 18.

Many alternative designs are possible. For example, in another design shown in FIGS. 18-19, a stylet 1800 could have a spline shape 1802 with splines 1804 formed along the stylet to better accommodate suction when the stylet in is the catheter tube. In other words, spaces 1806 are formed between the splines 1804 to allow suction to be provided through the catheter tube 102 even with the stylet 1800 in place within the catheter tube 102. Other configurations are possible.

Figure 20:
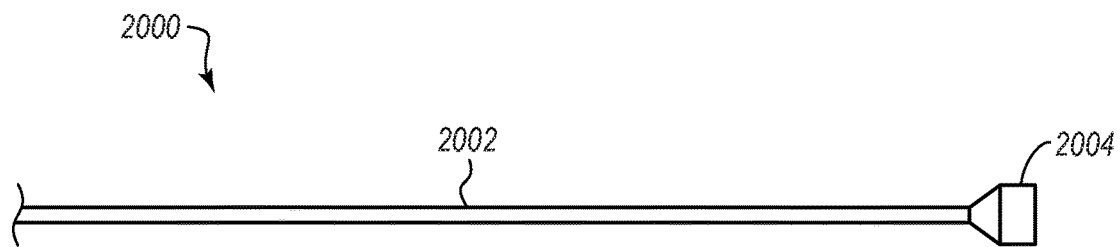
FIG. 20 shows another example embodiment of a system for removing a bolus of food or other debris lodged within an esophagus.
Figure 21:
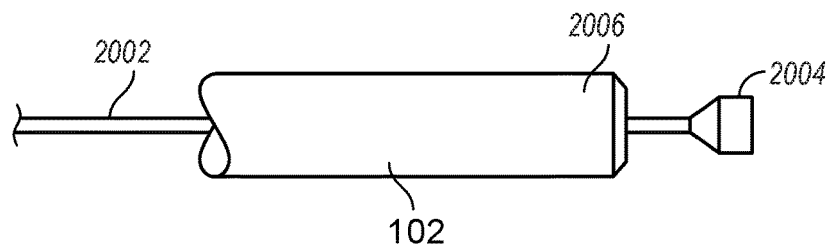
FIG. 21 shows a portion of the device of FIG. 20.

Referring now to FIGS. 20-21, another example of a stylet 2000 is shown. In this example, the stylet 2000 is a wire 2002 with a piston 2004 positioned at an end 2006 thereof. The piston 2004 can be automatically (and/or manually) actuated intermittently or at regularly intervals (such as by a motor) to drive the stylet 2000 through the catheter tube 102 to engage the blockage in the esophagus. Other configurations are possible.

Figure 22:
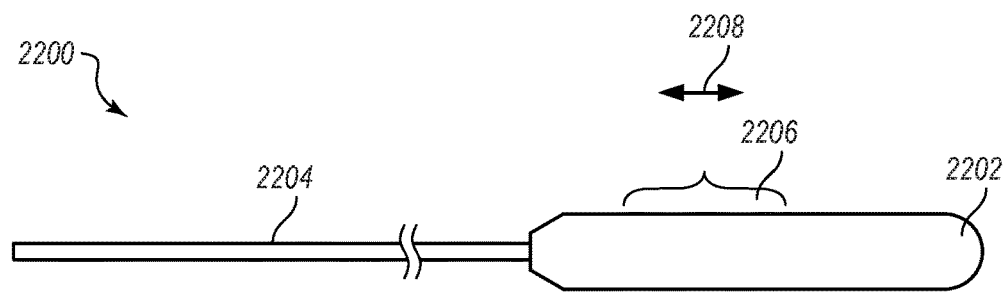
FIG. 22 shows another example embodiment of a system for removing a bolus of food or other debris lodged within an esophagus.
Figure 23:
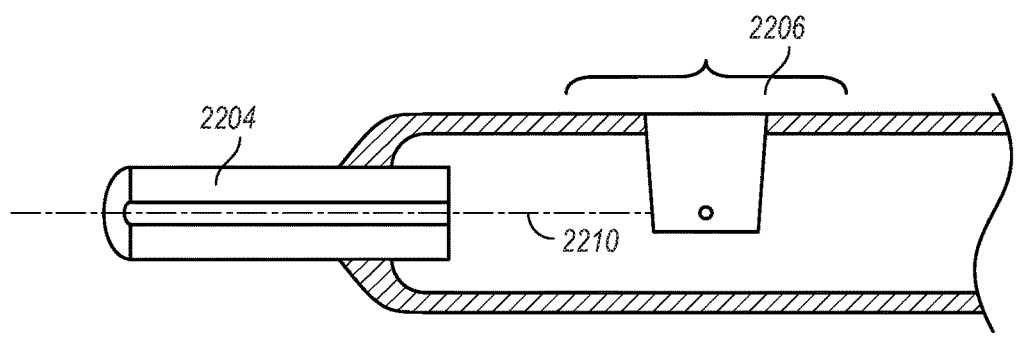
FIG. 23 shows a cross-sectional view of a portion of the device of FIG. 22.
Figure 24:
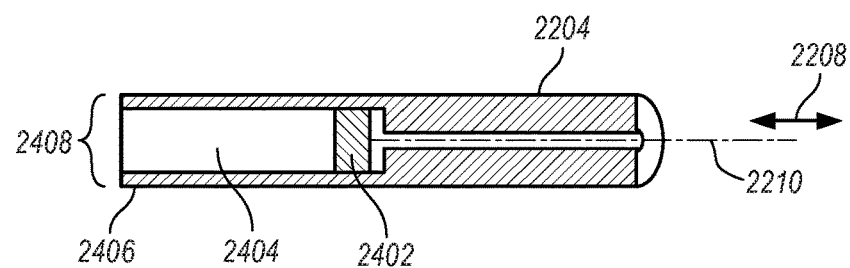
FIG. 24 shows another cross-sectional view of a portion of the device of FIG. 22.

Referring now to FIGS. 22-24, another example device 2200 is shown. The device 2200 is similar to the embodiment of FIGS. 20-21, except that the device 2200 does not necessarily need suction. Instead, the device 2200 includes a handle 2202 and a tube 2204. The handle 2202 includes an actuator member 2206 that can be moved (e.g., by the caregiver's finger or thumb) in a direction 2208 in or out.

The actuator member 2206 is coupled to a wire 2210 that runs through the tube 2204 to an ejector piston 2402. The ejector piston 2402 is positioned within a cavity 2404 formed in a distal end 2406 of the tube 2204. The distal end 2406 of the tube 2204 forms an opening 2408 sized to core or otherwise carve the obstruction as the caregiver moves the handle 2202 and the tube 2204 attached thereto. This is accomplished, for example, by the pieces of the obstruction being carved by the distal end 2406 of the tube 2204 and received in the cavity 2404.

As the cavity 2404 is filled, the caregiver can move the actuator member 2206 to cause the ejector piston 2402 to be moved by the wire 2210 through the cavity 2404 towards the distal end 2406 of the tube 2204 to eject food out of the opening 2408. This process can be done multiple times until the obstruction is cleared. The actuator member 2206 can be biased to return to the retracted position and/or simply be moved in the opposite direction 2208 by the caregiver's finger to return the ejector piston 2402 to the retracted position.

In some examples, the distal end 2406 of the tube 2204 can be configured to more easily core the obstruction. For example, the distal end can be thinned or serrated so as to be sharper. In other examples, additional features, such as a stainless steel tip, can be added to the distal end 2406 of this (or any other embodiment disclosed herein) to enhance the coring impact of the device 2200.

In some examples, the inner surface of the tubes can be configured to more easily allow cores of the obstruction to pass therethrough. For example, the inner surface of a tube can be coated with a low friction or lubricious material to encourage passage and discourage clumping of the cores. Examples of such low friction materials include, without limitation, polyvinyl pyrrolidone and hyaluronic acid. Such materials can be typically bonded using heat or ultraviolet light. The external surface of the catheter 102 can optionally also be coated with low friction materials to enable passage through the endoscope. Other mechanisms, such as differing tapers and/or channeling of the inner surface, can also be used.

Further embodiments of blockage clearing systems are disclosed hereafter. The systems can resemble systems described above in certain respects. Specific features of these further systems may not be shown or identified by a reference numeral in the drawings or specifically discussed in the written description that follows. However, such features may clearly be the same, or substantially the same, as features depicted in other embodiments herein (whether discussed above or below) and/or described with respect to such embodiments. Accordingly, the relevant descriptions of such features apply equally to the features of the following systems. Any suitable combination of the features and variations of the same described with respect to any of the systems and their components can be employed with any of the remaining systems and their components, and vice versa. Moreover, with respect to certain embodiments described hereafter, similar components among various embodiments may be identified with similar numbering, wherein the initial numerals may be incremented in subsequently disclosed embodiments.

Figure 25:
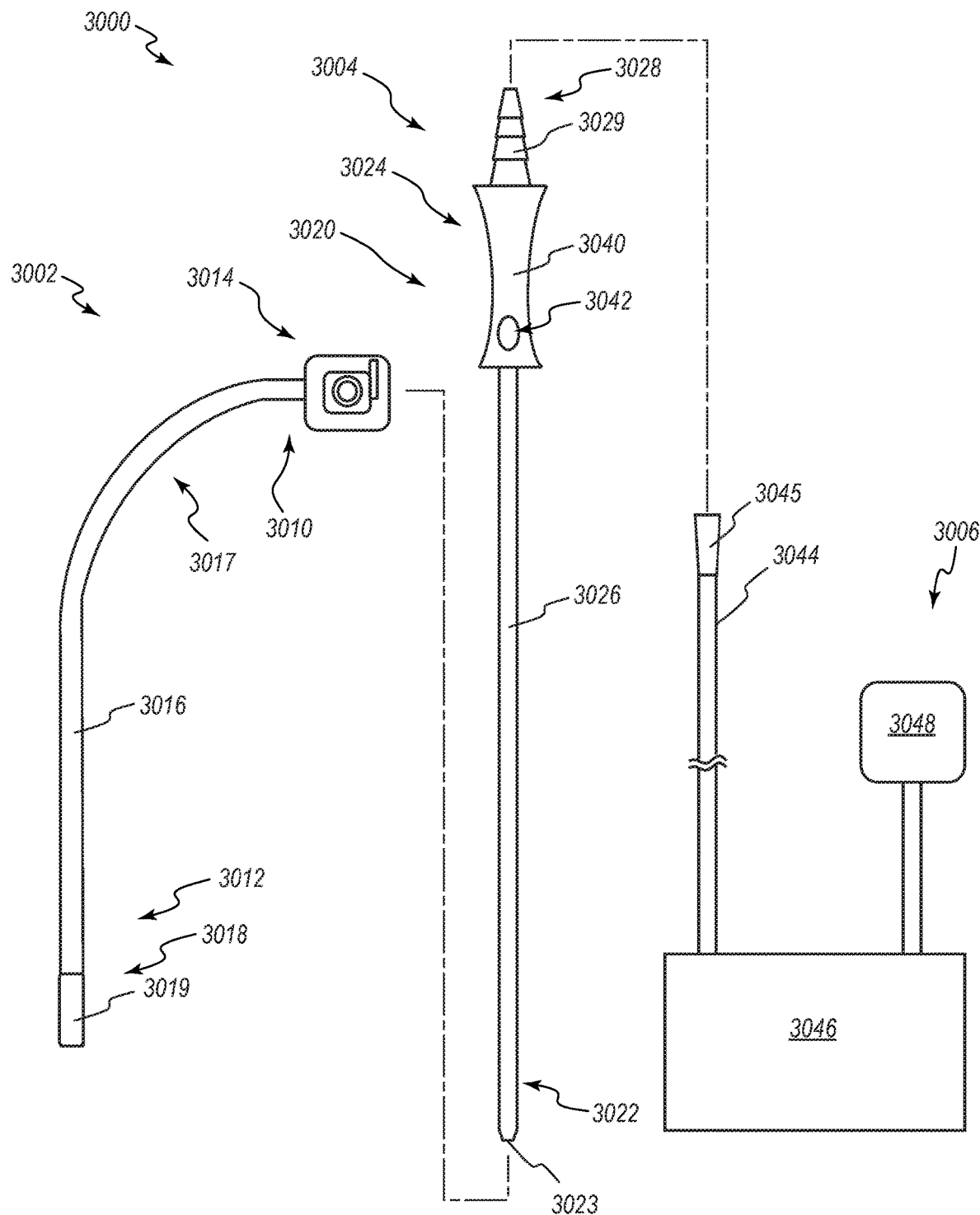
FIG. 25 is an exploded elevation view of another embodiment of a blockage clearing system.

FIG. 25 depicts an exploded view of an embodiment of a blockage clearing system 3000 that includes a sheath assembly 3002 and a catheter assembly 3004. The sheath assembly 3002 is configured to be coupled with the catheter assembly 3004 during use, as further discussed below. Moreover, the catheter assembly 3004 is configured to be coupled with a suction system 3006 during use.

The sheath assembly 3002 extends between a proximal end 3010 that is configured to remain outside of the patient during use and a distal end 3012 that is configured for insertion into the esophagus of a patient. The illustrated sheath assembly 3002 includes a hub 3014, a sheath 3016, and a positioning element 3018. As further discussed below, the hub 3014 of the sheath assembly 3002 can be configured to direct a catheter 3026 of the catheter assembly 3004 into a lumen of the sheath 3016. The catheter 3026 may also be referred to as a catheter tube, or more generally, as a tube, cannula, cutting member, cutting-and-suction member, or coring member. In further instances, the catheter 3026 may be referred to as an aspiration catheter, aspiration cannula, or aspiration tube.

At least a proximal portion of the sheath 3016 may define a preformed curve region 3017. In some embodiments, the curved region 3017 is sized and oriented to facilitate introduction of the sheath 3016 into the esophagus of a patient. The curved region 3017 may additionally or alternatively enhance the patient's comfort during use of the sheath 3016, such as when the curved portion 3017 extends through the mouth, against or adjacent to the soft palate, and through the hypopharynx. The curved portion 3017 may be pre-formed to correspond to a natural curvature of a patient's anatomy. In some embodiments, different sized sheath assemblies 3002 may be used for different sized patients to adjust to their differently sized anatomies, which may enhance comfort of the patients. In other embodiments, the curved region 3017 may be sufficiently flexible to adjust to different patient anatomies. A variety of configurations and alterations are contemplated. For example, in other embodiments, the sheath 3016 may be devoid of a curved region 3017. As can be appreciated from the foregoing, in such embodiments that lack a pre-formed curved region 3016, the sheath 3016 may be substantially linear prior to insertion into the patient, and can be sufficiently flexible to follow, deflect, adjust, and/or conform to a curvature of the patient's anatomy as the sheath 3016 is advanced through the mouth, against or adjacent to the soft palate, and through the hypopharynx of the patient. In other or further embodiments, the sheath 3016 may be advanced through the nose and through at least a portion of the upper respiratory tract and into the esophagus of the patient.

As further discussed below, the positioning element 3018 can assist in centering or otherwise positioning a distal tip 3023 of the catheter 3026 relative to the esophagus to prevent the distal tip 3023 from contacting or damaging the esophagus. In the illustrated embodiment, the positioning element 3018 is formed as an inflatable balloon 3019. Other or further varieties of positioning elements 3018 are also contemplated, illustrative examples of which are discussed further below. In various embodiments, the positioning element 3018 may also or instead be referred to as a centering element, anchoring element, contact element, expansion element, spacing element, and/or as a centering, anchoring, contact, expansion, and/or spacing member.

With continued reference to FIG. 25, the catheter assembly 3004 extends between a proximal end 3020 that is configured to remain outside of the patient during use and a distal end 3022 that is configured for insertion into the esophagus of a patient. As further discussed below, the distal end 3022 of the catheter 3026 can include a distal tip 3023 that is capable of coring an impacted food bolus. The distal tip 3023 may be sharp, and may be referred to as one or more of a cutting tip or a coring tip. In some embodiments, the distal tip 3023 can cut into the food bolus on its own and/or in combination with suction provided by the suction system 3006. In further embodiments, the distal tip 3023 can cooperate with the suction provided by the suction system 3006 to core the food bolus, e.g., as the suction tears from the food bolus a morsel that has been cut by the distal tip 3023.

Figure 29:
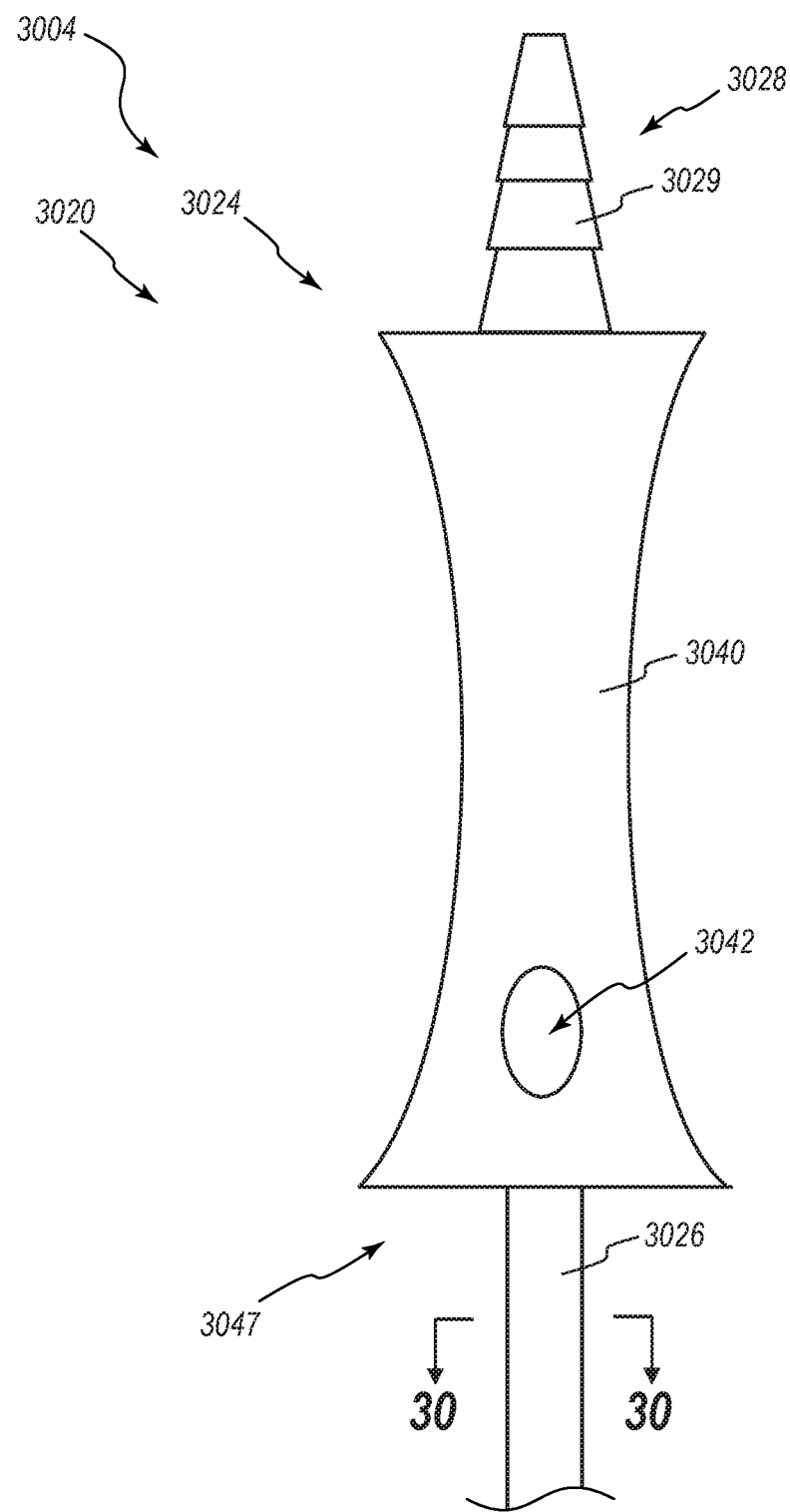
FIG. 29 is an elevation view of a proximal end of an embodiment of a catheter assembly that may be used with the system of FIG. 25.

The illustrated catheter assembly 3004 includes a hub 3024 attached to a proximal end of the catheter 3026. As further discussed below, the catheter hub 3024 can be configured to selectively couple with the suction system 3006. In the illustrated embodiment, the catheter hub 3024 includes a connector 3028 for establishing a fluid connection to the suction system 3006. In the illustrated embodiment, the connector 3028 is formed as a Christmas tree fitting or connector 3029. Any other suitable connection interface is contemplated. For example, the connector 3028 may instead define a substantially smooth outer surface, such as a smooth conical surface similar to that of the connector at the proximal end 106 of the catheter assembly 100 depicted in FIG. 1, rather than a ribbed outer surface of multiple stacked conical surfaces, such as depicted in FIGS. 25 and 29.

In the illustrated embodiment, the catheter hub 3024 includes a handle 3040 and a suction port 3042 positioned thereon. The handle 3040 can be of any suitable configuration. In many embodiments, the handle 3040 is sized and shaped to rest or be gripped comfortably within a single hand of a practitioner. For example, in some embodiments, the handle 3040 can be gripped with four fingers of a hand of a practitioner, and the port 3042 can be operated with the thumb of the same hand of the practitioner. In some embodiments, the port 3042 can be left open to prevent suction from being applied, or to significantly reduce an amount of suction being applied, through the catheter 3026. Conversely, the port 3042 can be closed, such as by placing a thumb or other finger thereon, to permit or increase an amount of suction to be applied through the catheter 3026. In other embodiments, such as in the catheter assembly 100 discussed above, the handle 3040 can be devoid of a suction port 3042. In such embodiments, suction through the catheter assembly 3004 can be continuous when the connector 3028 is coupled with the suction system 3006.

In the illustrated embodiment, the suction system 3006 includes a suction tube 3044, a container or suction trap 3046, and a suction, aspiration, or vacuum source 3048. The suction tube 3044 may be of any suitable variety, and may be configured to couple with the connector 3028 of the catheter assembly 3004. For example, in some embodiments, the suction tube 3044 may include a suction fitting 3045, such as the suction fitting 221 discussed above. The suction trap 3046 can be configured to permit air to pass through, but may be configured to retain therein pieces of a food bolus that are removed from a patient via the system 3000. The suction trap 3046 may include any suitable filters or other arrangements, including those known in the art or those yet to be devised. For example, the suction trap 3046 can comprise a collection canister, such as the collection canister 222 disclosed above. The vacuum source 3048 may be of any suitable variety. For example, in some embodiments, the vacuum source 3048 can be a dedicated vacuum line or vacuum system of a hospital.

Figure 26:
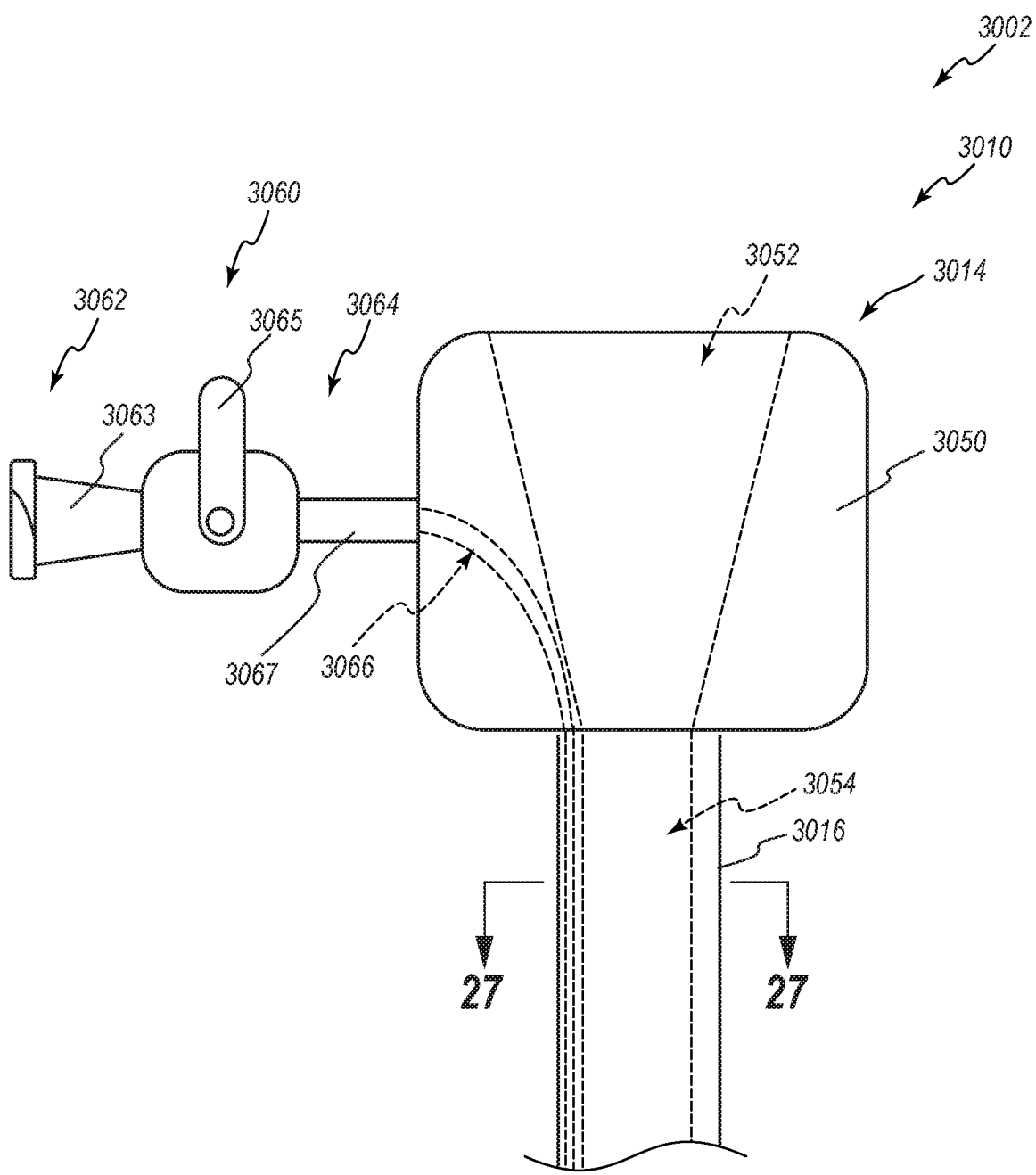
FIG. 26 is a side elevation view of a proximal end of an embodiment of a sheath assembly that may be used with the system of FIG. 25.

With reference to FIG. 26, the proximal end 3010 of the sheath assembly 3002 is shown in greater detail and from a viewpoint that is rotated 90 degrees about a vertical axis relative to the view of FIG. 25. In the illustrated embodiment, the sheath hub 3014 includes a housing element 3050 that defines an entry passage or guide 3052. In the illustrated embodiment, the guide 3052 is substantially funnel shaped, which can facilitate insertion of the distal end 3022 of the catheter 3026 into a lumen 3054 of the sheath 3016.

The sheath hub 3014 further includes an actuator 3060 via which the positioning element 3018 can be deployed. In particular, in the illustrated embodiment, the actuator 3060 is configured as an inflation port 3060 via which the balloon 3019 can be selectively inflated or deflated. Stated otherwise the actuator 3060 is communicatively coupled with the balloon 3019, and, in this instances, the communication comprises fluid communication. The illustrated inflation port 3060 includes a connector 3062, such as a Luer fitting 3063, via which any suitable inflation device can be connected thereto. In various embodiments, the inflation device can be an air-, gas- liquid-, or other fluid-filled syringe or other medical fluid delivery device. In various embodiments, saline, air, nitrogen, or any other suitable fluid may be used to inflate the balloon 3019. In some embodiments, the inflation device may have its own pressure controls, such as to ensure that the fluid is delivered to the balloon 3019 within an acceptable range, or stated otherwise, does not exceed a predetermined limit. Any suitable inflation device, including any known in the art or any yet to be devised, is contemplated.

The sheath hub 3014 can further include a stopcock 3064 that can be selectively opened and closed via a handle or lever 3065. The stopcock 3064 can be opened to permit inflation or deployment of the balloon 3019, and can be closed maintain the balloon 3019 in an inflated or deployed state. In particular, the stopcock 3064 can be in an open configuration to permit passage of inflation fluid therethrough for inflation of the balloon 3019, and once the balloon 3019 has been filled to a desired amount and/or the fluid pressurized to a desired or predetermined level, the stopcock 3064 can be closed to prevent passage of the fluid back through the stopcock and thus maintain the balloon 3019 in a filled, inflated, and/or pressurized state.

The inflation port 3060 can be in fluid communication with an inflation lumen 3066, which may also be referred to as an inflation passageway, channel, etc. Stated otherwise, and is apparent from at least the foregoing, the connector 3062 is in fluid communication with the stopcock 3064, and the stopcock 3064 is in fluid communication with the inflation lumen 3066. When the stopcock 3064 is in the open state, the connector 3062 is in fluid communication with the inflation lumen 3066, and when the stopcock 3064 is in the closed state, the connector 3062 no longer fluidly communicates with the inflation lumen 3066. The stopcock 3064 may be said to be in line with, between, or fluidly coupled with the connector 3062 and the inflation lumen 3066. In the illustrated embodiment, the housing 3050 defines a proximal end of the inflation lumen 3066, and the inflation lumen 3066 extends through a sidewall of the sheath 3016. As shown in FIG. 26, an extender 3067 of any suitable variety may extend between the housing 3050 and the stopcock 3064 to establish fluid communication between the inflation port 3060 and the inflation lumen 3066. For example, the extender 3067 can comprise tubing (e.g., flexible tubing) of any suitable variety.

Figure 27:
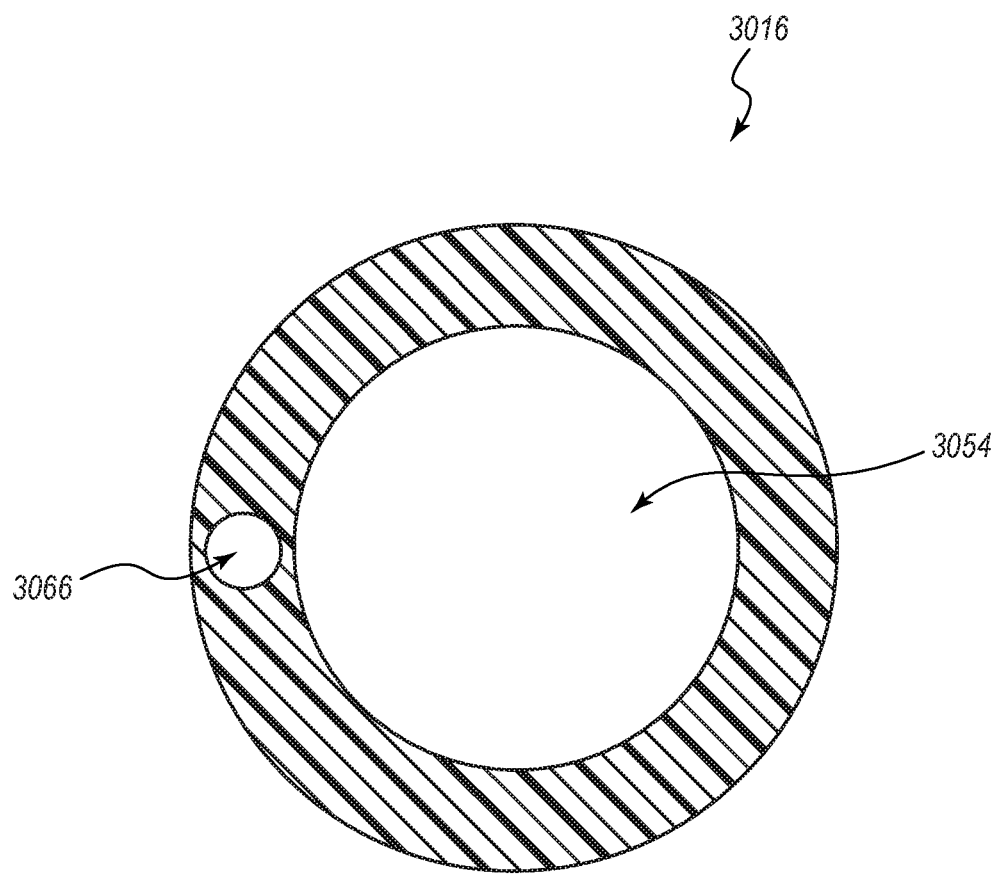
FIG. 27 is a cross-sectional view of a sheath portion of the sheath assembly of FIG. 26 taken along the view line 27-27 in FIG. 26.

With reference to FIG. 27, the inflation lumen 3066 and the instrument delivery lumen 3054 of the sheath 3016 are shown in greater detail. Any suitable arrangement of the lumens 3054, 3066 is contemplated. In various embodiments, more than one inflation lumen 3066 may be present. For example, in some embodiments, one or more additional inflation lumens may be present in the sheath 3016 for redundancy in the event that one of the lumens is inadvertently blocked, such as due to kinking of the sheath 3016. The sheath 3016 may generally be referred to as a tubular member that defines a channel through which the catheter 3026 can be advanced. In particular, the sheath 3016 defines the working channel or lumen 3054.

In various embodiments, the sheath 3016 may be formed of a material and/or a thickness of the sidewall may be sufficient to provide the sheath 3016 with desirable amounts of columnar or other strength. For example, in various embodiments, the sheath 3016 can resist compression, crushing, kinking, and/or other deformation that could undesirably alter the shape of the lumen 3054 in a manner that could interfere with insertion therein and/or removal therefrom of the catheter 3026. As previously noted, the material may also be flexible so as to permit the sheath 3016 to conform to the anatomy of a patient. For example, the material may be sufficiently flexible to permit the sheath 3016 to be bent from a substantially linear arrangement to a curved arrangement as the sheath 3016 is inserted through the mouth of the patient into the esophagus, all while maintaining the lumen 3054 sufficiently patent to permit ready passage therethrough of the catheter 3026. Various suitable materials for a catheter are disclosed above, and in many instances, these and/or other suitable materials for the sheath are contemplated. For example, in various embodiments, the sheath 3016 comprises any suitable thermoplastic elastomer, such as any suitable variety of PEBAX®, available from Arkema. Moreover, in some embodiments, a lubricious layer or coating may be provided at the inner surface of the sheath 3016, which could facilitate insertion of the catheter 3026 into the lumen 3054 and/or removal of the catheter 3026 from the lumen 3054.

Any suitable size of the sheath 3016 for insertion into the esophagus is contemplated. For example, in various embodiments, the sheath 3016 (i.e., the outer diameter thereof) can be no larger than 7, 10, 15, 20, 25, or 30 French. In some embodiments, the sheath 3016 is between 7 and 30 French, between 7 and 25 French, between 7 and 20 French, or between 7 and 15 French. In some embodiments, the lumen 3054 is sized to receive a catheter 3026 that is only slightly smaller, which can allow a lumen of the catheter 3026 to be relatively large and permit ready passage therethrough of cored pieces of blockage material (e.g., food). For example, in some embodiments, the sheath 3016 is 12 French, which can be fairly easy for many patients to swallow, and the catheter 3026 can be as large as 10 or 11 French. In various embodiments, the catheter 3026 can be no less than 4, 6, 8, 10, or 12 French, or may be between 4 and 12 French.

Figure 28A:
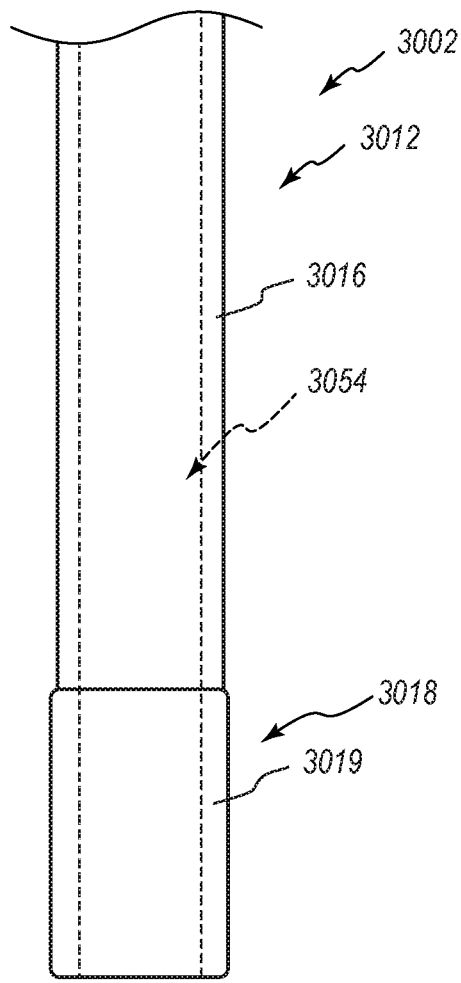
FIG. 28A is an elevation view of a distal end of the sheath assembly that includes a positioning element in an undeployed state.

FIG. 28A depicts the distal end 3012 of the sheath assembly 3002 when the positioning element 3018 is in the undeployed state. As can be seen, the balloon 3019 can define an outer diameter that may be only slightly greater than an outer diameter of more proximal portions of the sheath 3016 when in the undeployed state. In other embodiments, the outer diameter of the undeployed balloon 3019 may be the same as or slightly smaller than that of an adjacent portion of the sheath 3016. In the illustrated embodiment, the instrument delivery lumen 3054 extends through an axial center of the balloon 3019. Stated otherwise, the balloon 3019 encompasses a longitudinal axis of the sheath 3016.

Figure 28B:
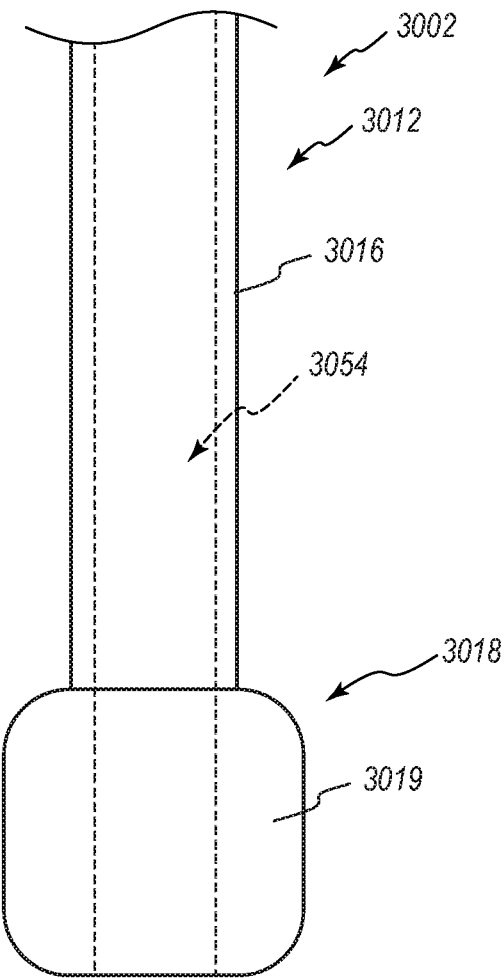
FIG. 28B is an elevation view of the distal end of the sheath assembly that depicts the positioning element in a deployed state.

FIG. 28B depicts the distal end 3012 of the sheath assembly 3002 when the positioning element 3018 has been transitioned to the deployed state, such as by introduction of an inflation fluid into the balloon 3019 via the inflation channel or inflation lumen 3066 (see FIG. 27). For example, as is clear from the foregoing disclosure, the inflation fluid can be introduced into the balloon 3019 by coupling a fluid-filled syringe or other medical fluid delivery device with the connector 3062, ensuring that the stopcock 3064 is in the opened state, and delivering fluid from the medical fluid delivery device through the connector 3062, through the stopcock 3064, through the inflation lumen 3066, and into the balloon 3019. Moreover, the balloon 3019 can be maintained in the deployed state by closing the stopcock 3064. As can be seen in FIG. 28B, the balloon 3019 can define an outer diameter that is significantly greater than an outer diameter of more proximal portions of the sheath 3016 when in the deployed state.

In certain embodiments, the balloon 3019 can be rotationally symmetrical when inflated. In further instances, the balloon 3019 can be configured to be rotationally symmetrical throughout inflation. Certain of such arrangements can substantially center the lumen 3054 relative to the esophagus. The inflated balloon 3019 also can anchor the lumen 3054 relative to the esophagus, or stated otherwise, the inflated balloon 3019 can stabilize the lumen 3054 relative to the esophagus to ensure the catheter tip 3023 does not come into contact with the esophageal wall. In certain embodiments, such an arrangement can ensure that the distal tip 3023 of the catheter 3026 does not come into contact with, or otherwise remains distanced from, the esophageal wall when the distal tip 3023 is advanced past the distal tip of the sheath 3016. Other arrangements are also contemplated. For example, in some embodiments, the lumen 3054 may not be centered relative to the esophagus. For example, in some embodiments, the positioning element 3018 may anchor the sheath 3016 such that a longitudinal axis thereof runs parallel to a central longitudinal axis of the esophagus. However, it may be desirable for the lumen 3054 to be centered relative to the esophagus to minimize the chances of contacting the esophagus wall with the distal tip 3023 of the catheter 3026 in any or all radial directions.

In some embodiments, the balloon 3019 is semi-compliant or non-compliant. For example, the balloon 3019 may expand to a predetermined size via application of a first amount of pressure therein, and thereafter may either expand only minimally or not at all upon further addition of pressure therein. In other or further embodiments, a portion of the balloon 3019 may be semi-compliant or non-compliant and another portion thereof can be compliant. For example, in some embodiments, a central portion of the balloon 3019 can be semi-compliant or non-compliant and one or more of a proximal or distal end of the balloon may be compliant. When the balloon 3019 is inflated to a predetermined pressure, the semi- or non-compliant portion defines a predetermined diameter, and if further pressure is applied, the proximal and/or distal ends may expand (e.g., longitudinally) to preserve the predetermined diameter of the balloon. Any suitable configuration of the balloon 3019 is contemplated. In some instances, it can be desirable for the balloon 3019 to not expand to a circumference or diameter that would damage the esophagus of the patient. On the other hand, it can be desirable for the balloon to expand by a sufficient amount to securely position the cutting distal tip 3023 of the catheter 3026 away from the esophageal wall. In some instances, the balloon can press against the esophageal wall around a full periphery of the balloon and/or around a full periphery of the inner surface of the esophageal wall.

FIG. 29 depicts the proximal end 3020 of the catheter assembly 3004 in greater detail than is shown in FIG. 25. As previously discussed, the catheter hub 3024 includes a handle 3040 and a suction port 3042. In the illustrated embodiment, the suction connector 3028 is positioned at a proximal end of the handle 3040. Other positions for the suction connector 3028 are contemplated.

Figure 30:
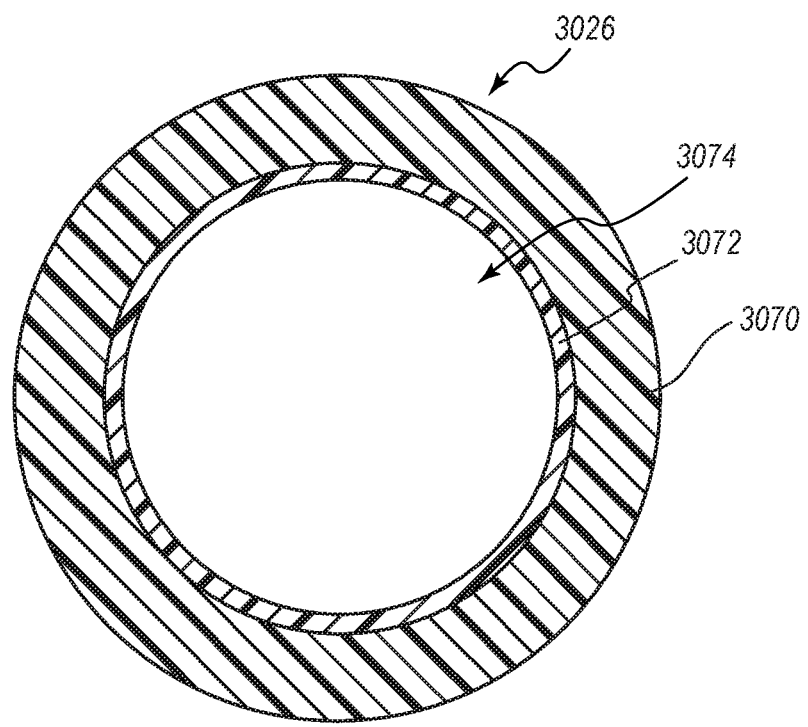
FIG. 30 is a cross-sectional view of a catheter portion of the catheter assembly of FIG. 29 taken along the view line 30-30 in FIG. 29.

FIG. 30 is a cross-sectional view of the catheter 3026. In the illustrated embodiment, the catheter 3026 includes a body 3070 and a lubricious layer 3072 at an internal surface thereof. The lubricious layer 3072 can define a lumen 3074 through which morsels of food that are removed from an impacted food bolus can pass.

The body 3070 can be formed of a material and/or can have a sidewall thickness that is sufficient to provide the catheter 3026 with desirable amounts of columnar or other strength. For example, in various embodiments, the catheter 3026 can resist compression, crushing, kinking, and/or other deformation that could undesirably alter the shape of the lumen 3074 in a manner that could interfere with passage therethrough of food morsels. Various suitable materials for the catheter 3026 are disclosed above. These and or other suitable materials are contemplated. For example, in some embodiments, the material comprises a relatively hard durometer. In other or further embodiments, the material may comprise a braided configuration. In some embodiments, the catheter 3026 may be more compliant than the sheath 3016. For example, in some embodiments, the sheath 3016 can protect the catheter 3026 from kinking or other undesired deformation. In some embodiments, the body 3070 can maintain its shape when significant suction forces are present within the lumen 3074.

The lubricious layer 3072 can be formed of any suitable material, and may have a low coefficient of friction or exhibit other physical properties that permit food morsels to pass readily by without sticking, adhering, or otherwise being stopped. In various embodiments, the lubricious layer 3072 can include one or more of PTFE or HDPE. In other embodiments, the lubricious layer 3072 may be omitted. For example, in some embodiments, the lumen 3074 is sufficiently large to reduce the chances of food morsels being stuck thereto during use. Stated otherwise, the lumen 3074 is sufficiently large to inhibit the food morsels from being stuck thereto during use.

In certain embodiments, an outer diameter of the body 3070 is sufficiently smaller than an inner diameter of the sheath 3016 to permit the body 3070 to readily pass through the sheath 3016. In some embodiments, the outer and inner diameters are sufficiently similar, however, such that the sheath 3016 can significantly limit lateral movement of the catheter 3026.

Figure 31:
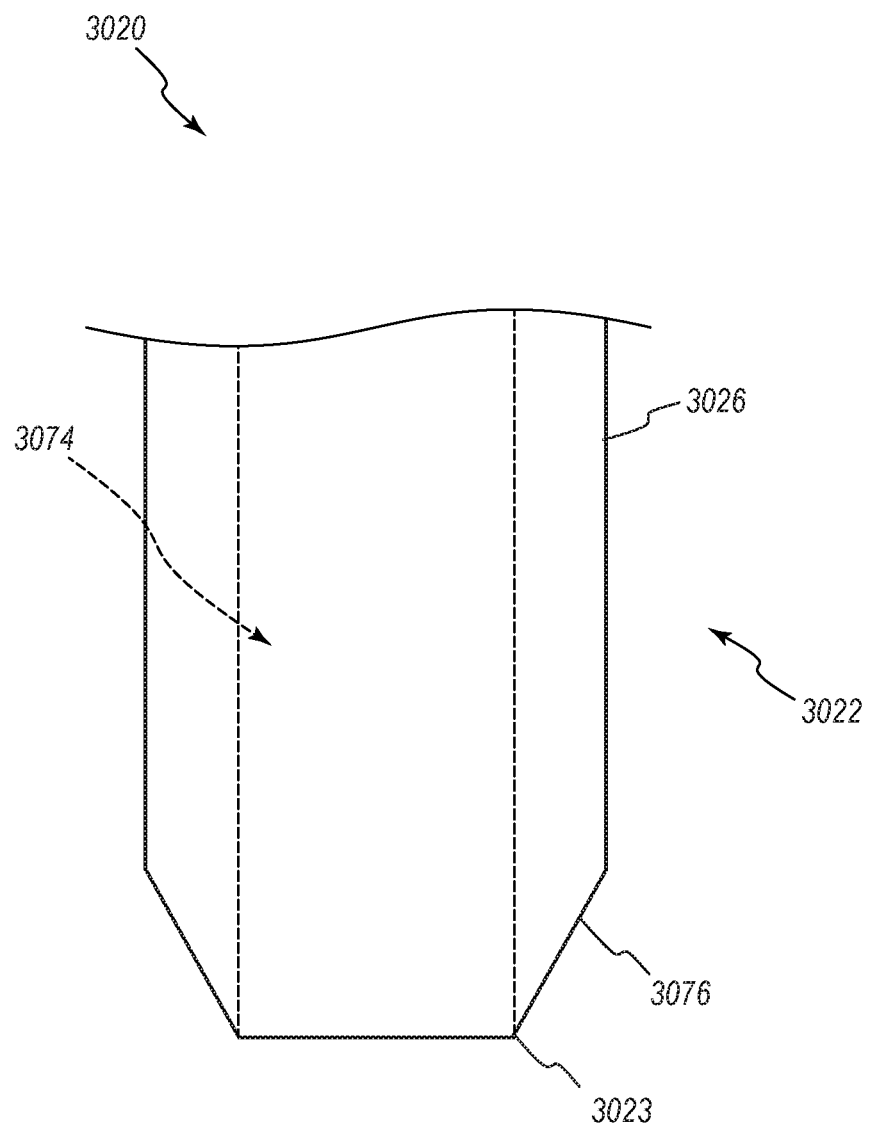
FIG. 31 is an elevation view of a distal end of the catheter of FIG. 29.

FIG. 31 depicts the distal end 3022 of the catheter assembly 3020 in greater detail than is shown in FIG. 25. In the illustrated embodiment, an inner diameter of the lumen 3074 is substantially constant along a full length of the catheter 3026. In other embodiments, such as those described in detail above, a diameter of the catheter 3026 may be narrower near the distal tip 3023 than it is along a proximal length thereof. An enlarged diameter along the proximal length may facilitate suctioning of food morsels through the catheter 3026 after those morsels are cored from the food bolus via the tip 3023.

In the illustrated embodiment, the distal tip 3023 defines a sharp edge. The edge is formed in part by a back bevel 3076 at an outer surface of the catheter 3026. Other cutting arrangements are contemplated, including those discussed further below.

Figure 32A:
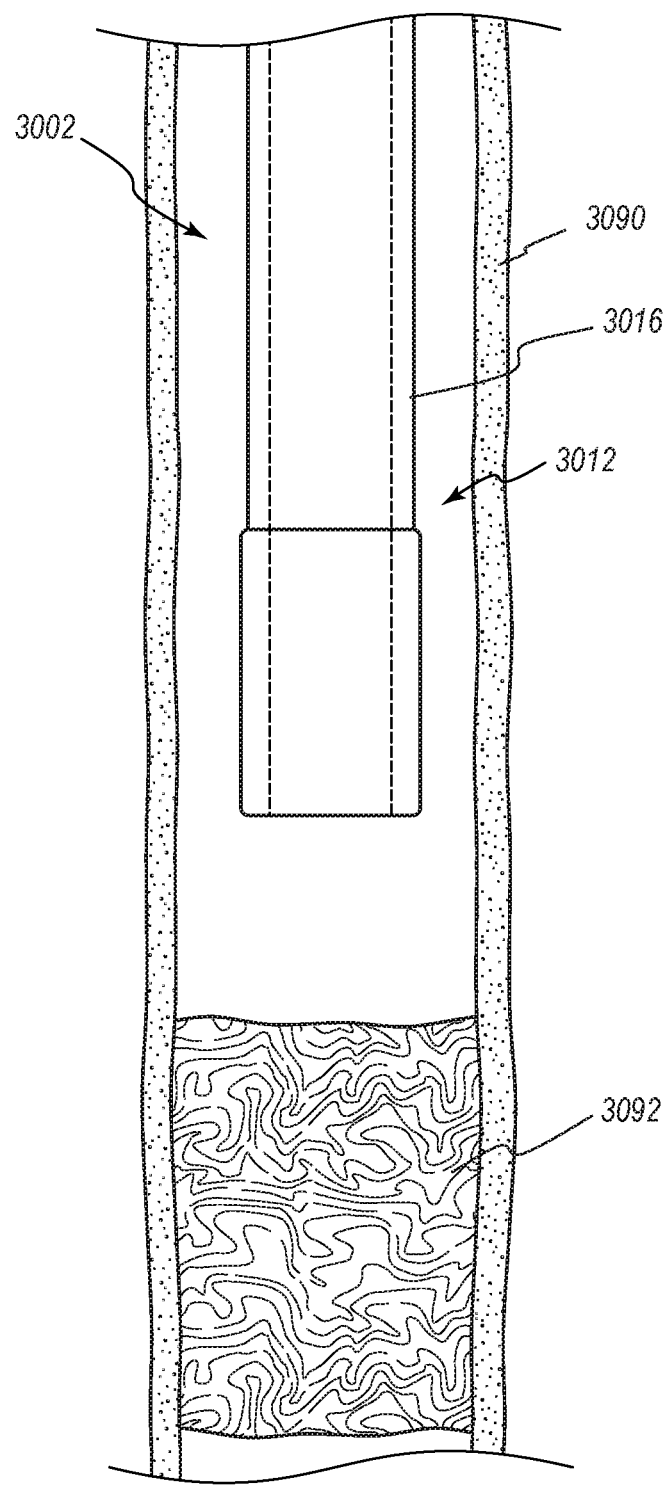
FIG. 32A is an early stage in an illustrative method of using the system of FIG. 25 in which the sheath is inserted into the esophagus of a patient.

FIG. 32A is an early stage in an illustrative method of using the system 3000. In the illustrated stage, the distal end 3012 of the sheath assembly 3002 is inserted into the esophagus 3090 of a patient. For example, the distal end 3012 of the sheath assembly 3002 can be inserted through the mouth of the patient and into the esophagus, as disclosed elsewhere herein. The distal tip of the sheath 3016 is advanced toward a foreign body 3092 that is lodged in the esophagus 3090. In the illustrated method, the foreign body 3092 is an impacted bolus of food, and will be referred to as such hereafter.

Figure 32B:
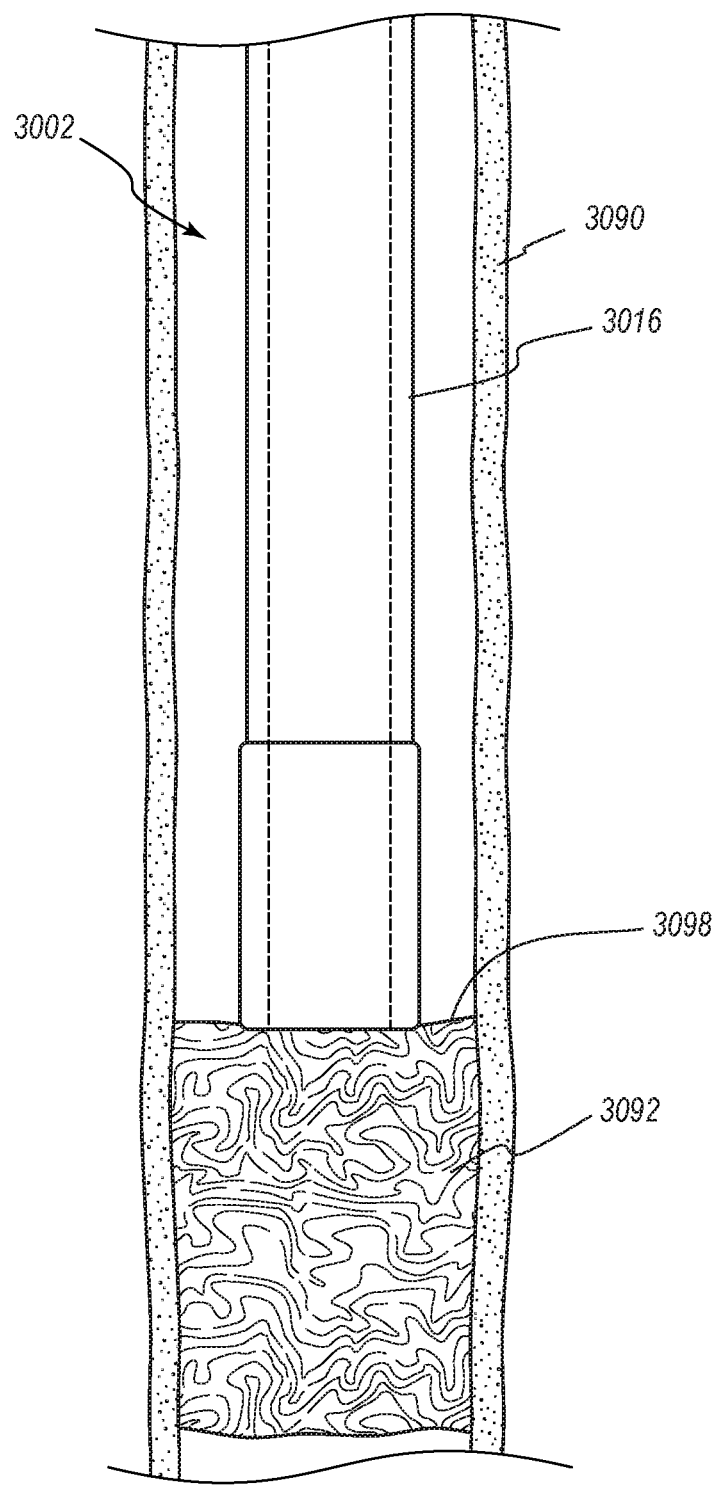
FIG. 32B is a subsequent stage in the illustrative method in which the distal end of the sheath contacts an impacted bolus of food.

FIG. 32B is a subsequent stage in the illustrative method. In the illustrated stage, the sheath 3016 has been advanced distally a sufficient distance to bring the distal tip of the sheath assembly 3002 into contact with a proximal end 3098 of the food bolus 3092. In some instances, the procedure is performed blind. As apparent from the present disclosure, performing a procedure "blind" means that the procedure is not visualized, such as via a camera of an endoscope, under fluoroscopy, etc. The practitioner may be able to discern this contact with the food bolus 3092 via tactile feedback. For example, the practitioner can sense that the food bolus 3092 has been reached by a sudden increase in resistance to distal advancement of the sheath 3016.

Figure 32C:
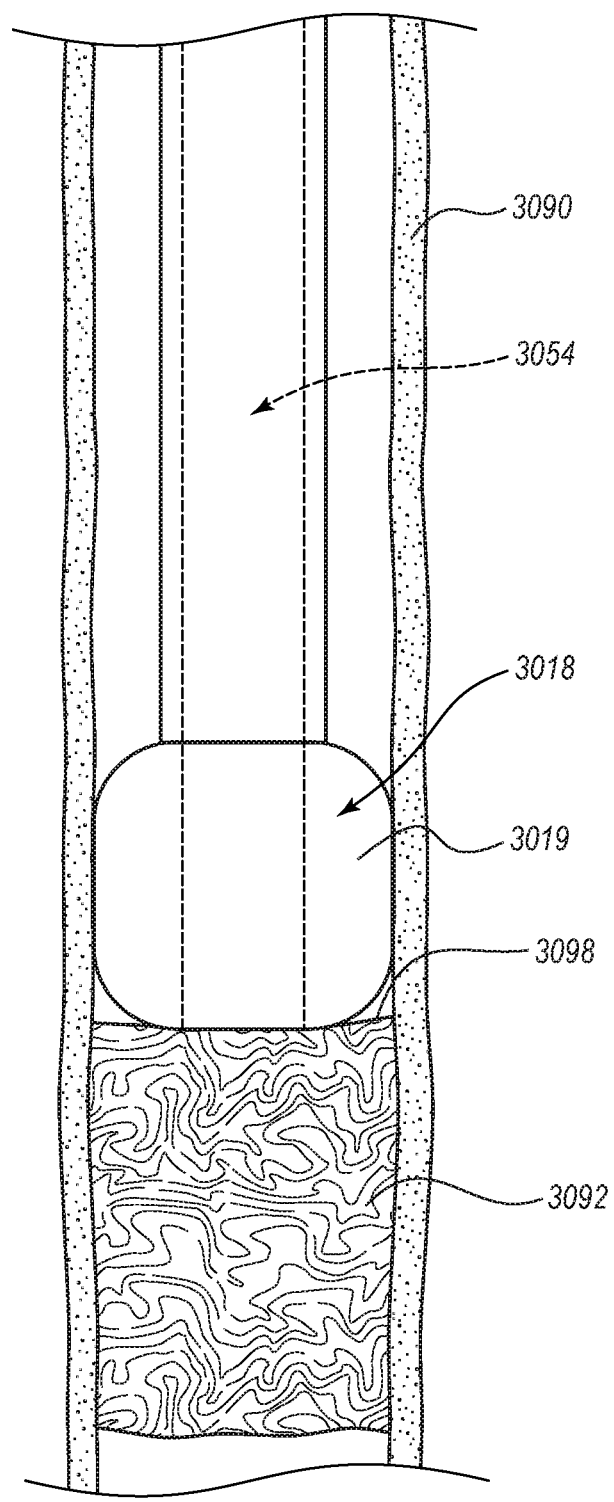
FIG. 32C is a subsequent stage in the illustrative method in which the positioning element is deployed into contact with the esophagus.

FIG. 32C is a subsequent stage in the illustrative method. In the illustrated stage, the positioning element 3018 is deployed into contact with the esophagus 3090. For example, as apparent from other disclosures herein, an inflation device (e.g., a syringe) can be coupled with the inflation port 3060 and, with the stopcock 3064 in the open state, an inflation fluid (e.g., air) can be delivered from the inflation device into the balloon 3019 to deploy the balloon 3019. Once the balloon 3019 has been deployed, the stopcock 3064 can be closed to maintain the balloon 3019 in the deployed state. In the illustrated embodiment, the positioning element 3018, or balloon 3019, substantially centers the lumen 3054 relative to the esophagus 3090.

Figure 32D:
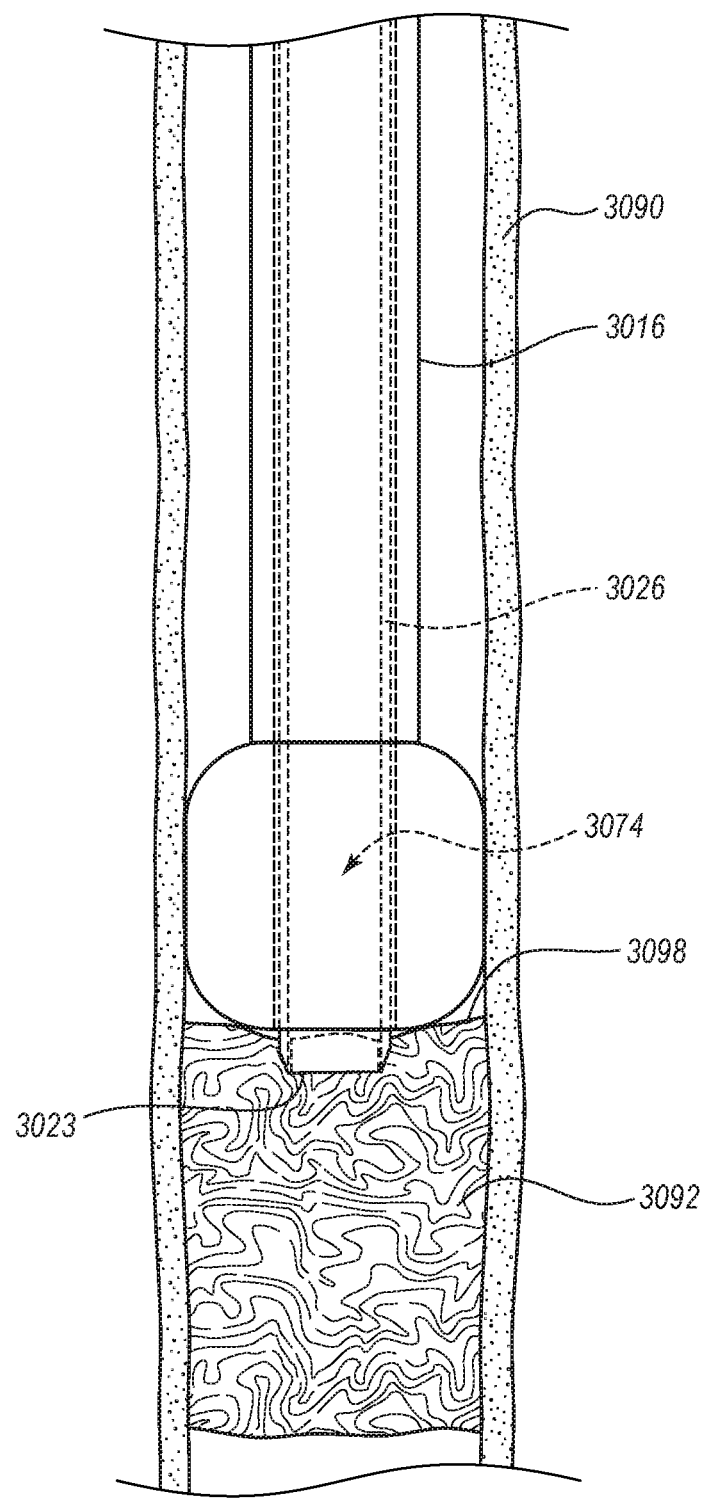
FIG. 32D is a subsequent stage in the illustrative method in which the distal tip of the catheter is advanced through the sheath and brought into contact with a proximal end of the food bolus.

FIG. 32D is a subsequent stage in the illustrative method in which the distal tip 3023 of the catheter 3026 is advanced through the sheath 3016 and brought into contact with the proximal end 3098 of the food bolus 3092. In some instances, suction may be applied via the catheter 3026 throughout advancement of the catheter 3026 toward the food bolus 3092. In other instances, the practitioner may utilize tactile feedback to determine that contact has been made with the food bolus 3092, and may then instigate suction. The suction can draw a portion of the food bolus 3092 into the lumen 3074

Figure 32E:
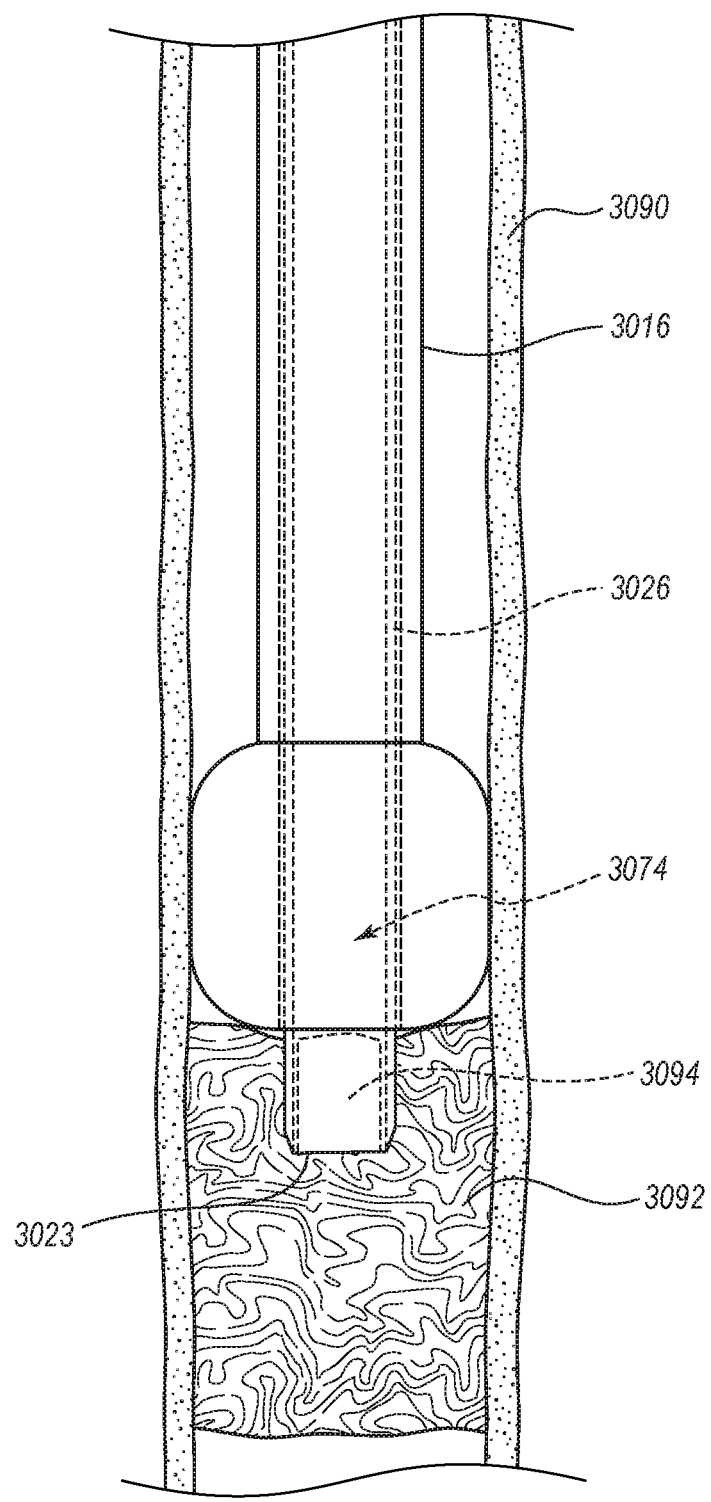
FIG. 32E is a subsequent stage in the illustrative method in which a morsel of food from the food bolus is cut or, more specifically, cored by the distal tip of the catheter and is drawn into a lumen of the catheter.

FIG. 32E is a subsequent stage in the illustrative method in which a morsel of food 3094 from the food bolus 3092 is cut, or cored, by the distal tip 3023 of the catheter 3026 and is drawn into the lumen 3074 of the catheter 3026. In some embodiments, the catheter 3026 defines a length that is only slightly longer than a length of the sheath 3016. This maximum advanced length of the catheter 3026 may be delimited to reduce the chances of the distal tip 3023 coming into contact with the esophageal wall. In various embodiments, the distal tip 3023 is limited from moving past the distal tip of the sheath 3016 by a distance of no greater than 0.25, 0.5, 0.75, 1.0, 1.25, 1.5, 1.75, or 2.0 inches. Stated otherwise, movement of the catheter 3026 relative to the sheath 3016 is delimited to inhibit the distal tip of the catheter 3026 from coming into contact with the esophageal wall when the distal end of the catheter 3026 is extended to its distalmost orientation relative to the sheath 3016.

In view of at least the foregoing disclosure and the drawings, it is apparent that delimitation of the maximum advanced length can be due to interaction of the proximal end 3020 of the catheter assembly 3004 and the proximal end 3010 of the sheath assembly 3002. For example, in the illustrated embodiment, the distal end of the catheter 3026 is attached to the catheter hub 3024, which defines an enlarged diameter, as compared with a diameter of the catheter 3026, at the distal end of the catheter hub 3024. The catheter hub 3024 can interact with the sheath hub 3014 to delimit the maximum advanced length to which the catheter 3026 can extend past the distal end of the sheath 3016. In particular, the catheter 3026 of the catheter assembly 3004 can be advanced distally through the guide 3052 of the sheath hub 3014 of the sheath assembly 3002, whereas the distal face of the catheter hub 3024 can interfere with a proximal face of the sheath hub 3014 or with the tapered surface of the guide 3052 to delimit the distal movement of the catheter 3026.

More generally, the catheter assembly 3004 can define a stopping region 3047 (see FIG. 29) having an enlarged diameter, relative to a diameter of a working length of the catheter 3026. This stopping region 3047 can, for example, be defined at least in part by the catheter hub 3024. In the illustrated embodiment, the stopping region 3047 is defined entirely by a distal end of the catheter hub 3024. The stopping region 3047 can interfere with a portion of the sheath hub 3014 to delimit distal movement of the catheter 3026. In the illustrated embodiment, the portion of the sheath hub 3014 with which the stopping region 3047 (e.g., the distal end of the catheter hub 3014) can interfere is the proximal face of the sheath hub 3014 or a proximal end of the guide 3052.

Figure 32F:
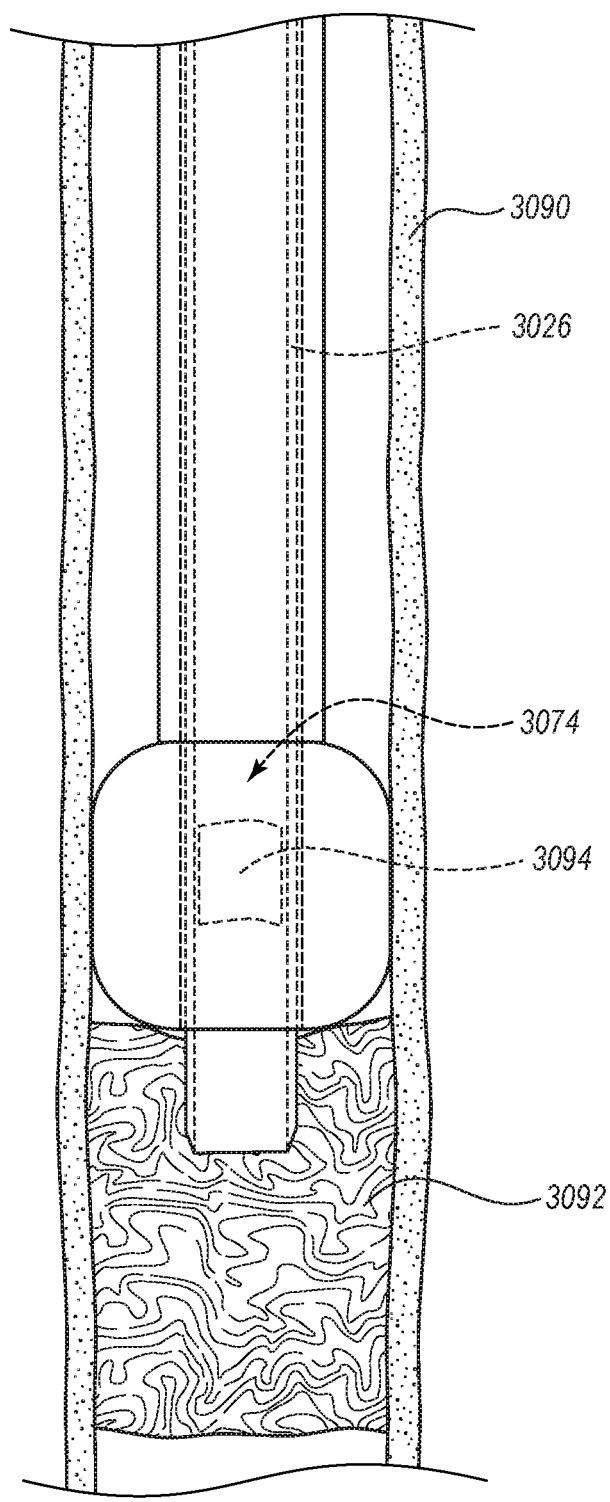
FIG. 32F is a subsequent stage in the illustrative method in which the morsel of food has detached from the food bolus and is suctioned through the lumen of the catheter.

FIG. 32F is a subsequent stage in the illustrative method in which the morsel of food 3094 has detached from the food bolus 3092 and is suctioned through the lumen 3074 of the catheter 3026.

Figure 32G:
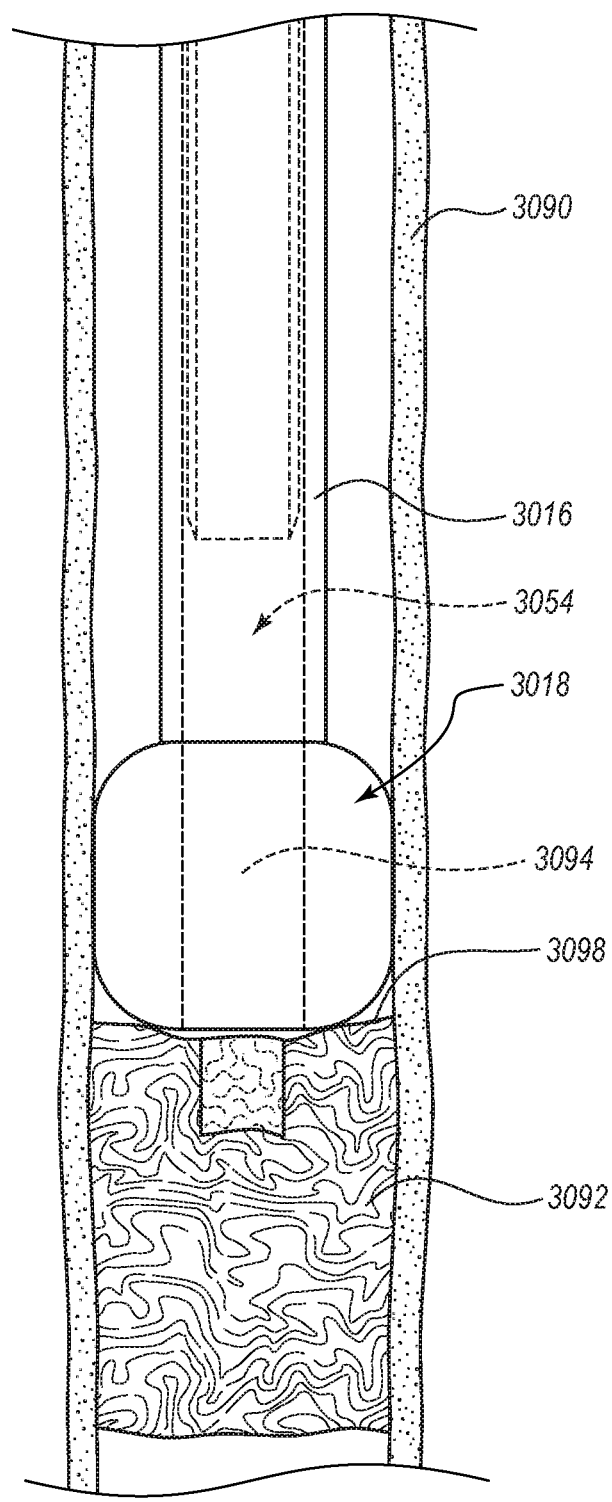
FIG. 32G is a subsequent stage in the illustrative method in which the catheter is withdrawn into or from the sheath.

FIG. 32G is a subsequent stage in the illustrative method in which the catheter 3026 is withdrawn from the sheath 3016. In some instances, the catheter 3026 is only partially withdrawn into the lumen 3054 so as not to inadvertently contact the esophagus. In other instances, the catheter 3026 may be fully withdrawn.

In some instances, a sufficient amount of material from the food bolus may have been withdrawn at this point for at least a portion of the food bolus to collapse by an amount sufficient to allow the food bolus to pass naturally into the stomach of the patient. Such passage may result in sudden relief to the patient, which can indicate that no further coring or clearing is needed. In some instances, the sheath 3016 and the catheter 3026 may be withdrawn together, or one after the other.

In other instances, it may be desirable to continue coring the food bolus 3092. Accordingly, in some instances, the procedure may continue, such as by positioning the system 3000 more distally within the esophagus 3090.

In some instances, the system 3000 can clear the food bolus 3092 without passing any portion of the system 3000 beyond a distal end of the food bolus 3092. In other or further instances, the system 3000 can clear the food bolus 3092 without passing any portion of the system 3000 completely through the food bolus 3092.

Figure 32H:
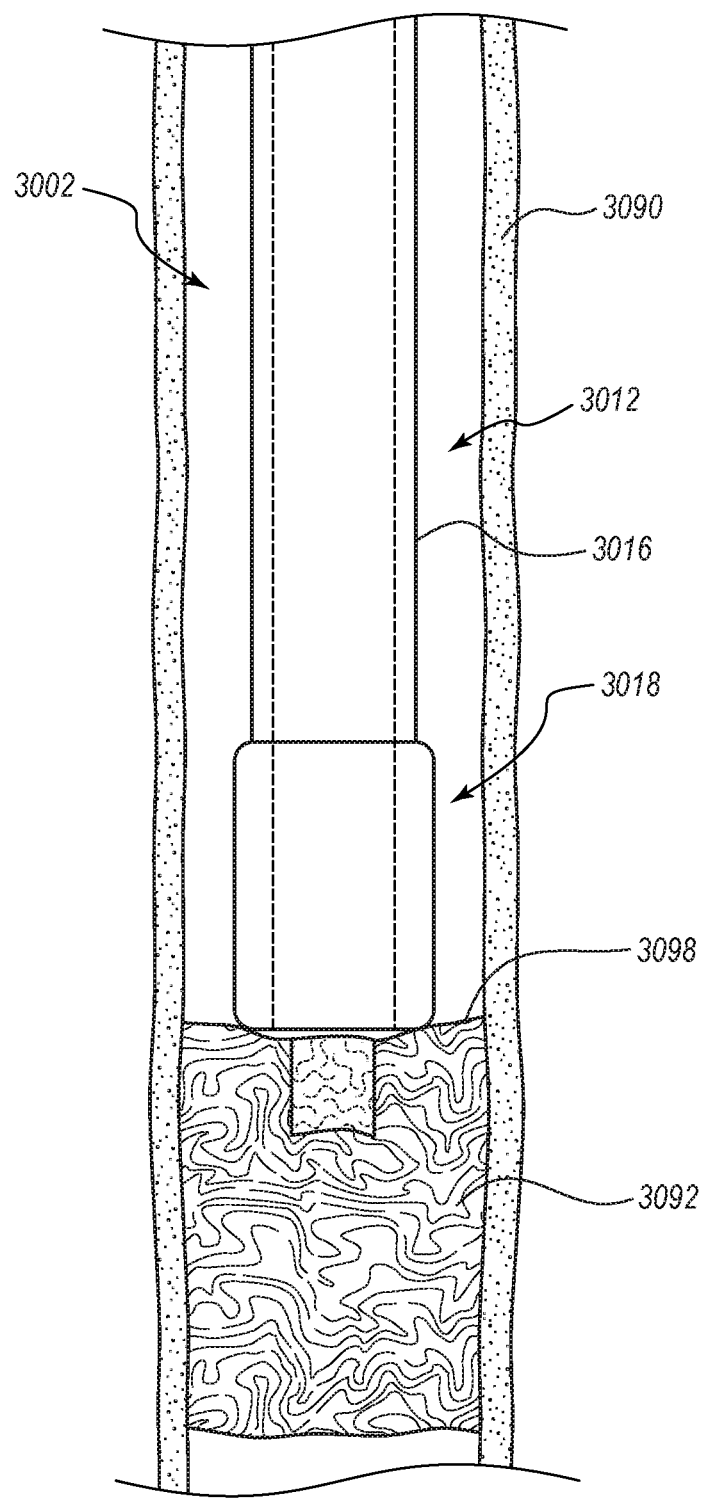
FIG. 32H is a subsequent stage in a further illustrative method in which further coring of the food bolus is desired, wherein in the depicted stage, the positioning element is returned to the undeployed configuration to permit ready movement of the sheath relative to the esophageal wall.

FIG. 32H is a subsequent stage in one such further illustrative method in which further coring of the food bolus is desired. In the depicted stage, the positioning element 3018 is returned to the undeployed configuration to permit ready movement of the sheath 3016 relative to the esophageal wall.

Figure 32I:
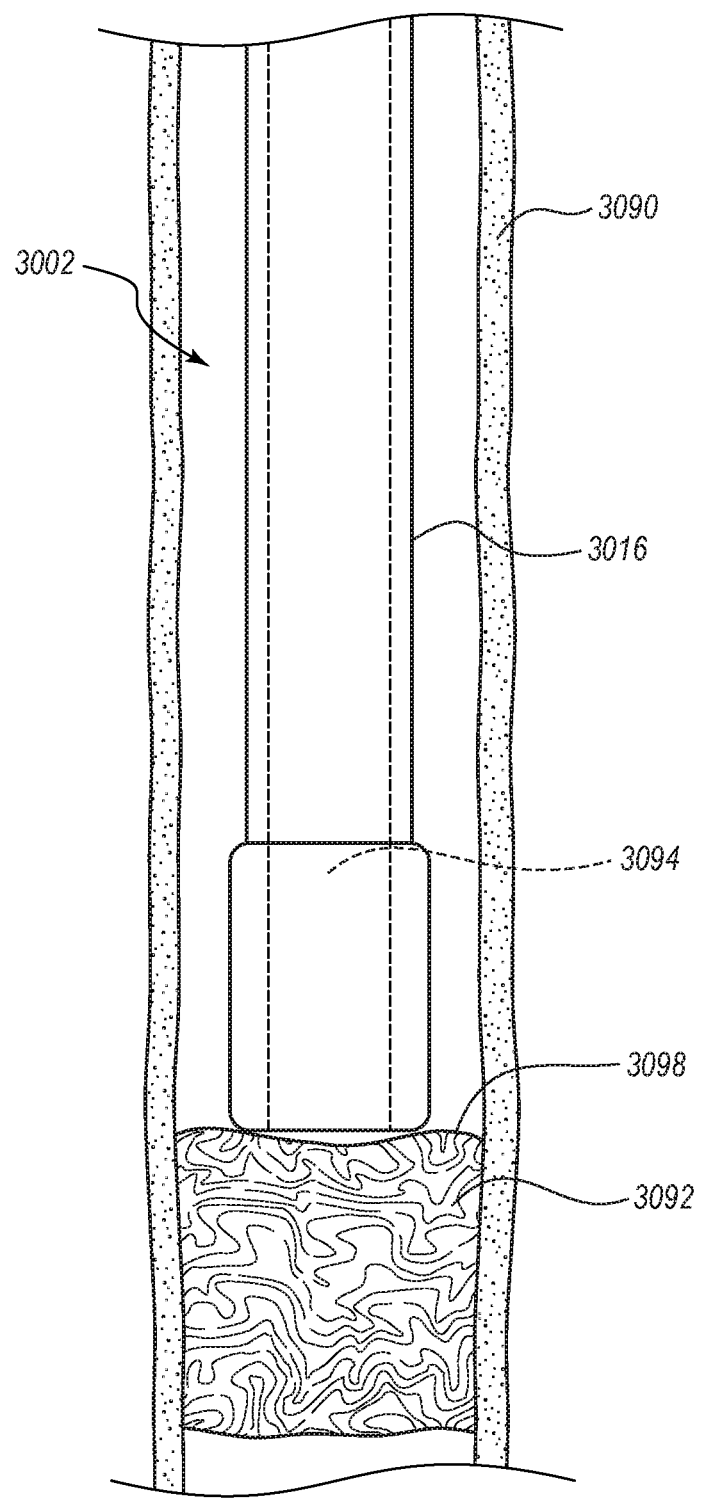
FIG. 32I is a subsequent stage in the further illustrative method in which the distal end of the sheath has been advanced to a more distal position, wherein the proximal end of the cored food bolus has been reshaped in the absence of the suctioned-off food morsel.

FIG. 32I is a subsequent stage in the further illustrative method in which the distal end of the sheath 3016 has been advanced to a more distal position within the esophagus 3090. The proximal end 3098 of the cored food bolus has been reshaped in the absence of the suctioned-off food morsel 3094.

Figure 32J:
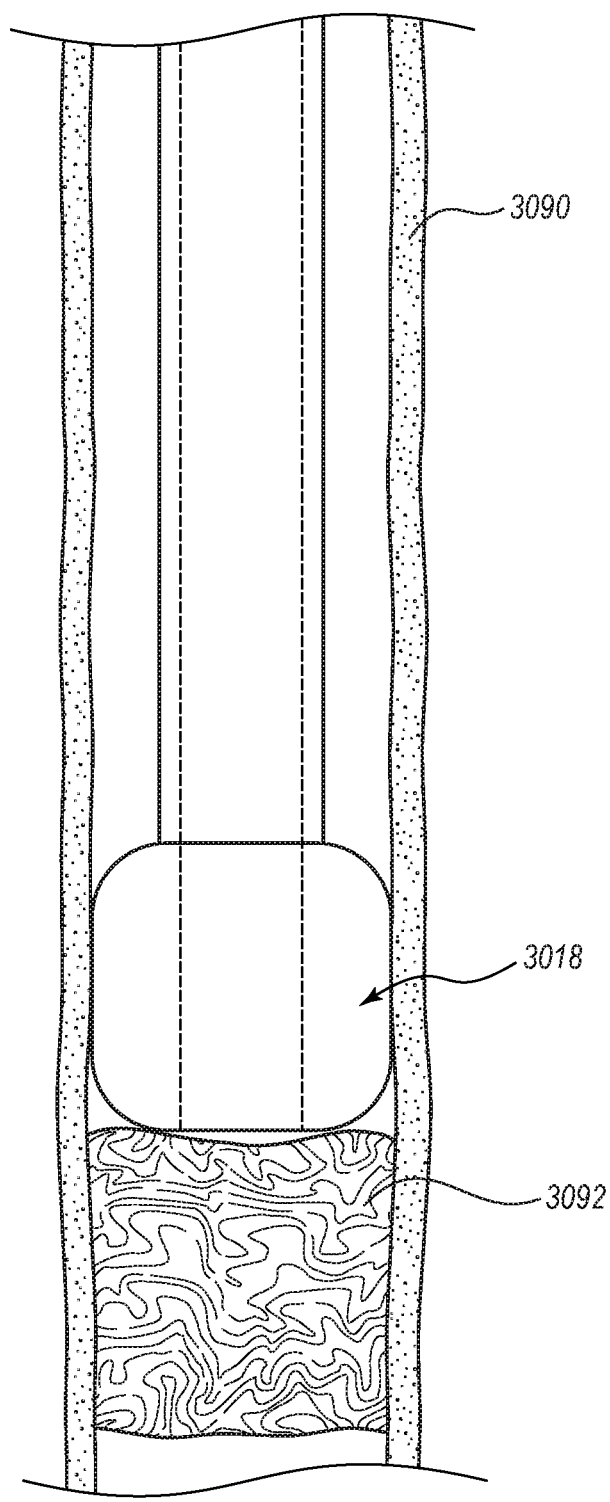
FIG. 32J is a subsequent stage in the further illustrative method in which the positioning element is deployed again into contact with the esophagus.

FIG. 32J is a subsequent stage in the further illustrative method in which the positioning element 3018 is deployed again into contact with the esophagus 3090. Such repositioning can, in certain instances, permit further coring of the food bolus 3092 with little or no risk of the distal end of catheter coming into contact with the esophagus.

Figure 32K:
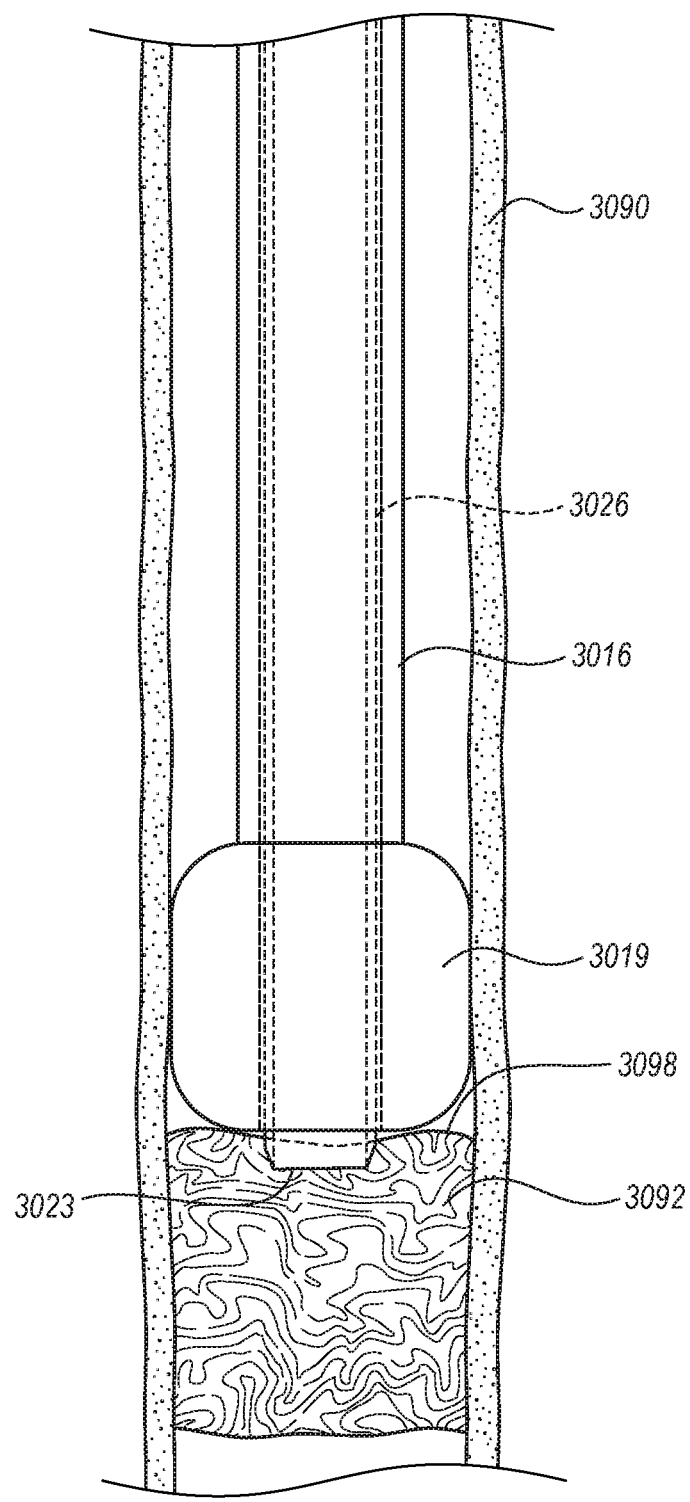
FIG. 32 K is a subsequent stage in the further illustrative method in which the distal tip of the catheter is again brought into contact with the proximal end of the food bolus for further coring of the food bolus.

FIG. 32K is a subsequent stage in the further illustrative method in which the distal tip 3023 of the catheter 3026 is again brought into contact with the proximal end 3098 of the food bolus 3092 for further coring thereof.

When coring is completed, the catheter 3026 can be drawn into the sheath 3016 to shield the sharpened distal end of the catheter 3026, or may be fully withdrawn from the sheath assembly 3002. The balloon 3019 can be deflated out of contact with the esophagus and fully or partially returned to the undeployed state. For example, the stopcock 3064 can be opened to release inflation fluid (e.g., air) from the balloon 3019. The sheath 3016 may then be withdrawn from the patient.

Figure 33A:
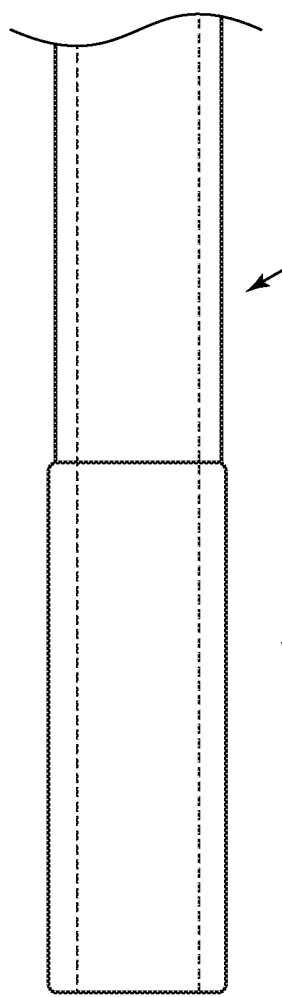
FIG. 33A is an elevation view of a distal end of another embodiment of a sheath assembly that includes a differently shaped positioning element in an undeployed state.

FIG. 33A is an elevation view of a distal end of another embodiment of a sheath assembly 3102 that includes a differently shaped positioning element 3118 in an undeployed state. In some embodiments, the positioning element 3118 comprises a balloon that is compressed, folded, or otherwise formed into a low-profile arrangement such as that depicted in FIG. 33A so as to have a substantially cylindrically shaped outer surface that may be only slightly larger than a cylindrical outer surface of the sheath to which it is attached.

Figure 33B:
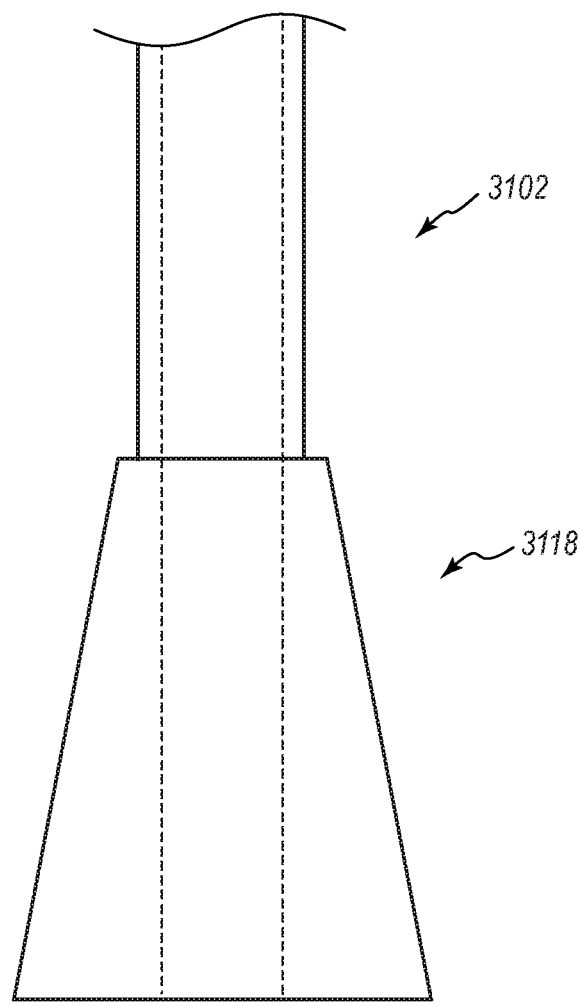
FIG. 33B is another elevation view of the distal end of the sheath assembly of FIG. 33A that depicts the positioning element in a deployed state in which the positioning element is substantially shaped as a frustocone.

FIG. 33B is another elevation view of the distal end of the sheath assembly 3102 that depicts the positioning element 3118 in a deployed state in which the positioning element 3118 is substantially shaped as a frustocone. Other configurations of the deployed positioning element 3118 are contemplated. As with the positioning element 3018 described above, in certain embodiments, the positioning element 3118 can be radially symmetrical.

Figure 34:
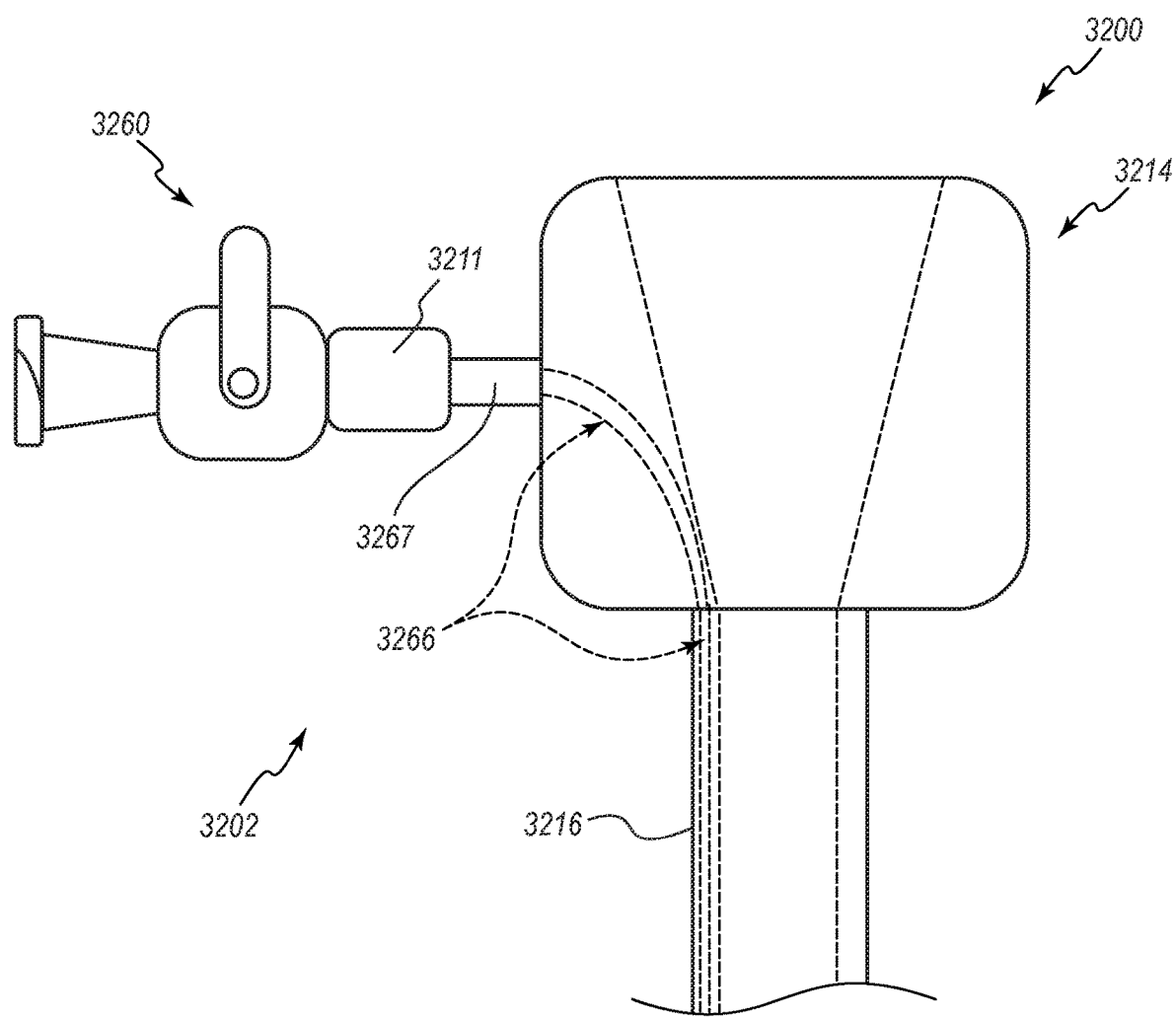
FIG. 34 is an elevation view of a proximal end of another embodiment of a sheath assembly that includes a pressure regulation valve.
Figure 35A:
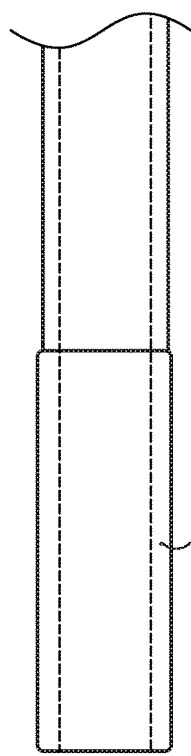
FIG. 35A is an elevation view of a distal end of the sheath assembly of FIG. 34 that depicts a positioning element in an undeployed state.
Figure 35B:
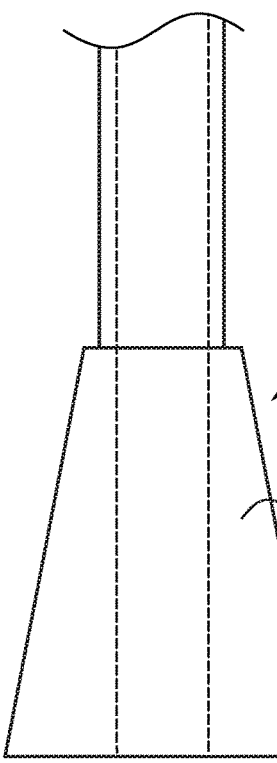
FIG. 35B is a further elevation view of the distal end of the sheath assembly of FIG. 34 that depicts the positioning element in a deployed state.

FIGS. 34, 35A, and 35B depict various views of another embodiment of a sheath assembly 3202 that includes a pressure regulation valve 3211. The pressure regulation valve 3211 can regulate a pressure within a positioning member 3218, such as an inflation balloon 3219. For example, the pressure regulation valve 3211 can ensure that a pressure within the inflation balloon 3219 does not exceed a preset maximum value. Such an arrangement may be configured to ensure that excess pressure that might injure or otherwise negatively impact the esophagus is not applied to the esophagus. As indicated in FIG. 34, the sheath assembly 3202 can be a component in another embodiment of a blockage clearing system 3200, such as the blockage clearing system 3000 described above.

The pressure regulation valve 3211 is depicted in fluid communication with a pressurization port 3260, which may also be referred to as an inflation port 3260. The pressure regulation valve 3211 is also depicted in fluid communication with an inflation lumen 3266. The pressure regulation valve 3211 is operationally positioned between the inflation port 3260 and the portion of the inflation lumen 3266 that is defined by a sheath 3216. Stated otherwise, the pressure regulation valve 3211 is in line with inflation port 3260 and is in line with the portion of the inflation lumen 3266 defined by the sheath 3216. In particular, in the illustrated embodiment, the pressure regulation valve 3211 is in line with each of the inflation port 3260 and the inflation lumen 3266, and further, is positioned between the inflation port 3260 and the inflation lumen 3266. The pressure regulation valve 3211 is coupled with a hub 3214. In particular, the pressure regulation valve 3211 is coupled to the hub 3214 via an extender 3267.

Figure 35C:
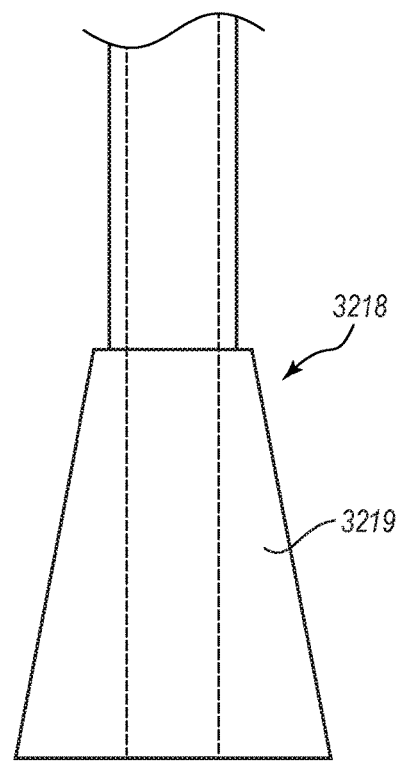
FIG. 35C is a further elevation view of the distal end of the sheath assembly of FIG. 34 that depicts the positioning element in a further state of operation in which the positioning element has been maintained in the deployed state at a substantially constant pressure via the pressure regulation valve of FIG. 34, despite attempts to further pressurize the positioning element.

FIG. 35A depicts the positioning element 3218 in an undeployed state. FIG. 35B depicts the positioning element 3218 in a deployed state. FIG. 35C depicts the positioning element 3218 in a further state of operation in which the positioning element has been maintained in the deployed state at a substantially constant pressure via the pressure regulation valve 3211, despite attempts to further pressurize the positioning element via the pressurization port 3260.

Figure 36:
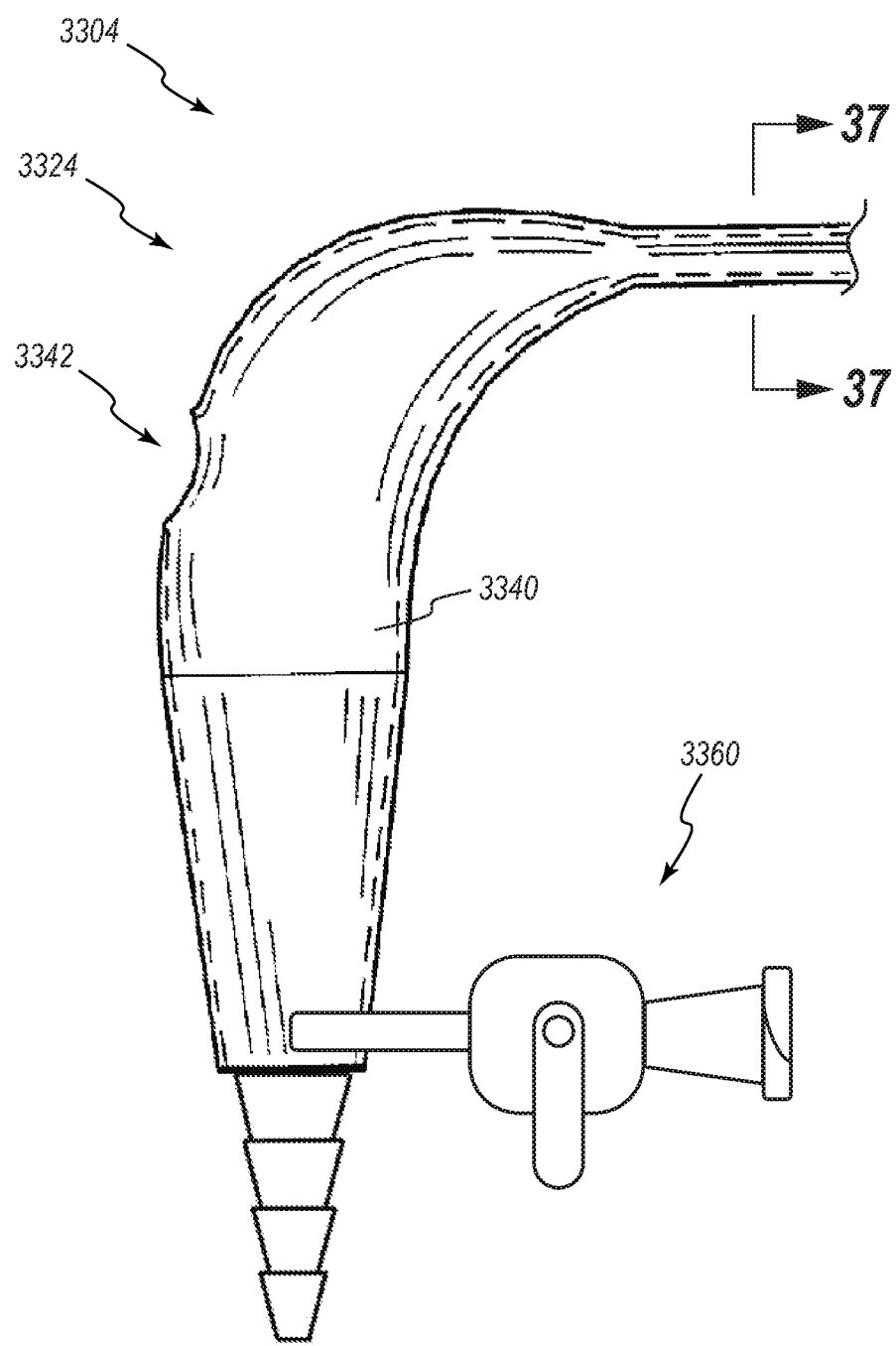
FIG. 36 is an elevation view of a proximal end of another embodiment of a catheter assembly that, in some instances, may be used with a system such as that depicted in FIG. 25, or in other instances, may be used without a sheath.

FIG. 36 is an elevation view of a proximal end of another embodiment of a catheter assembly 3304 that, in some instances, may be used with a system such as the system 3000 discussed above; in other or further instances, may be used with an endoscope; or in still other instances, may be used without a sheath or endoscope. The catheter assembly 3304 can include a hub 3324 similar to the hub 3024 discussed above. For example, the catheter assembly 3304 includes a handle 3340 having a different gripping arrangement (more akin to a gun or drill) and a similar suction port 3342. The hub 3324 can further include an actuator or inflation port 3360, such as the inflation port 3060 discussed above with respect to the sheath assembly 3002.

Figure 37:
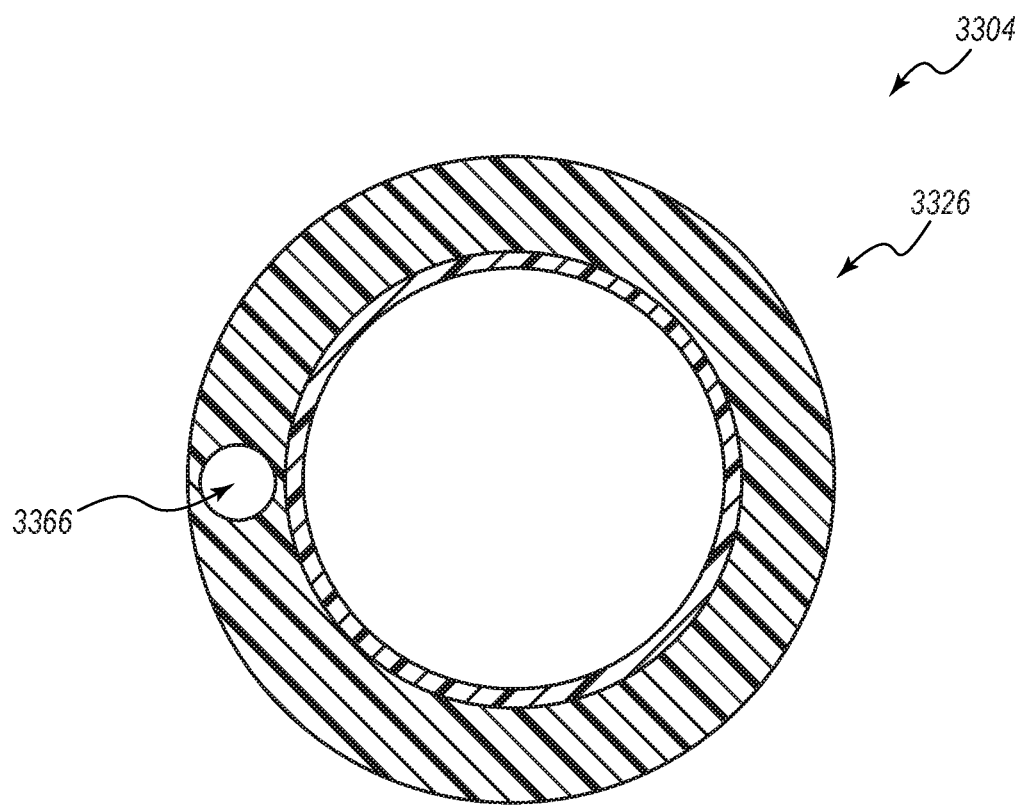
FIG. 37 is a cross-sectional view of a catheter portion of the catheter assembly of FIG. 36 taken along the view line 37-37 in FIG. 36.

FIG. 37 is a cross-sectional view of a catheter 3326 of the catheter assembly 3304. The catheter 3326 can resemble the catheter 3026 described above in many respects, but may further include an inflation channel or inflation lumen 3366, such as the like-numbered lumen 3066 discussed above with respect to the sheath 3016.

FIG. 38A is an elevation view of a distal end of the catheter assembly 3304 in which a positioning element 3318 is depicted in an undeployed state. The positioning element 3318 can function in the same manner as other positioning elements described above, and may be in fluid communication with the inflation lumen 3366. The positioning element 3318 can distance a distal tip 3323 of the catheter 3326 from the esophagus wall when deployed. For example, the positioning element 3318 may be symmetrical and/or may center the distal tip 3323 from the esophagus. In the illustrated embodiment, the distal tip 3323 is positioned at a distance distally from the distal end of the positioning element 3318.

FIG. 38B is another elevation view of the distal end of the catheter assembly 3304 in which the positioning element 3318 is depicted in a deployed state, such as described with respect to various other embodiments above.

Figure 39A:
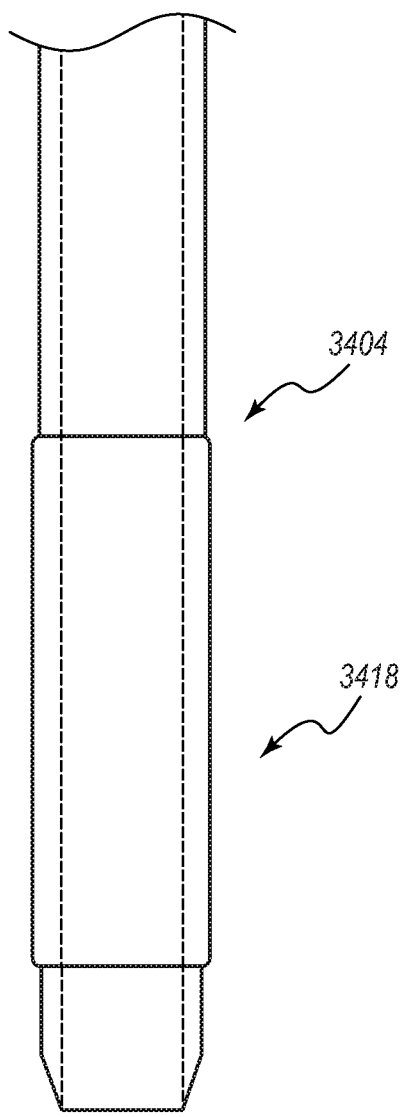
FIG. 39A is an elevation view of a distal end of another embodiment of a catheter assembly that includes a differently shaped positioning element that is depicted in an undeployed state.
Figure 39B:
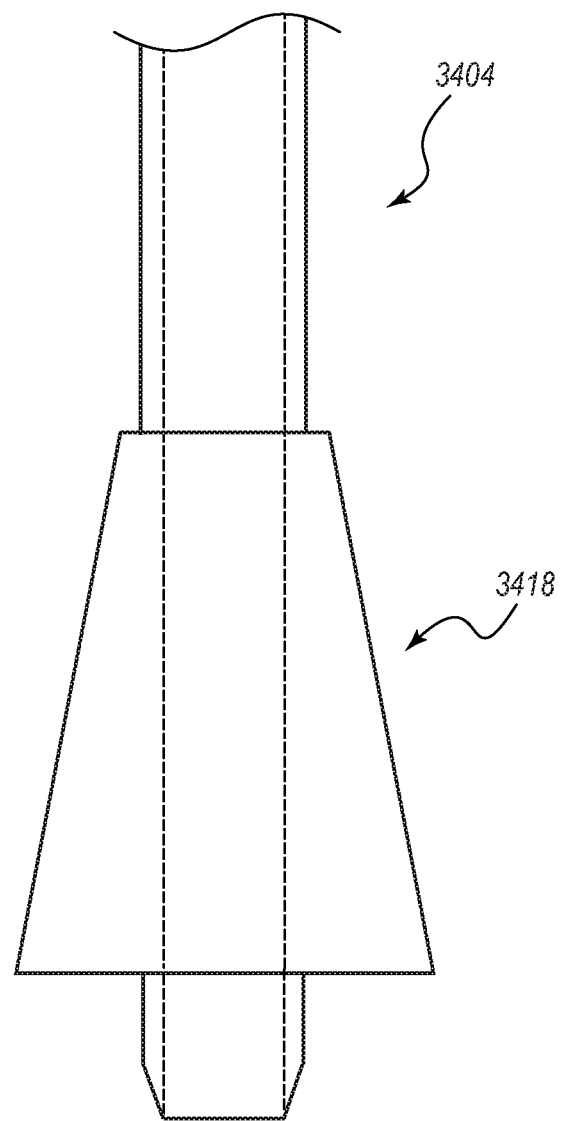
FIG. 39B is another elevation view of the distal end of the catheter assembly of FIG. 39A that depicts the positioning element in a deployed state.

FIG. 39A is an elevation view of a distal end of another embodiment of a catheter assembly 3404 that includes a differently shaped positioning element 3418 that is depicted in an undeployed state. FIG. 39B is another elevation view of the distal end of the catheter assembly 3404 that depicts the positioning element 3418 in a deployed state. In some embodiments, the catheter assembly 3404 is used to clear an impacted food bolus in manners such as described above, but without a sheath. In other embodiments, the catheter assembly 3404 is used with a sheath, such as the sheath 3016, in manners such as described above. For example, both the sheath 3016 and the catheter assembly 3404 can include inflatable positioning members that inhibit contact between the esophagus and the catheter. In still other or further embodiments, the catheter assembly 3404 can instead be inserted into the esophagus of a patient through the working channel of an endoscope. The positioning element 3418 can be advanced past a distal end of the endoscope and deployed into contact with the esophagus to prevent inadvertent contact of the distal tip of the catheter to the esophageal wall.

Figure 40A:
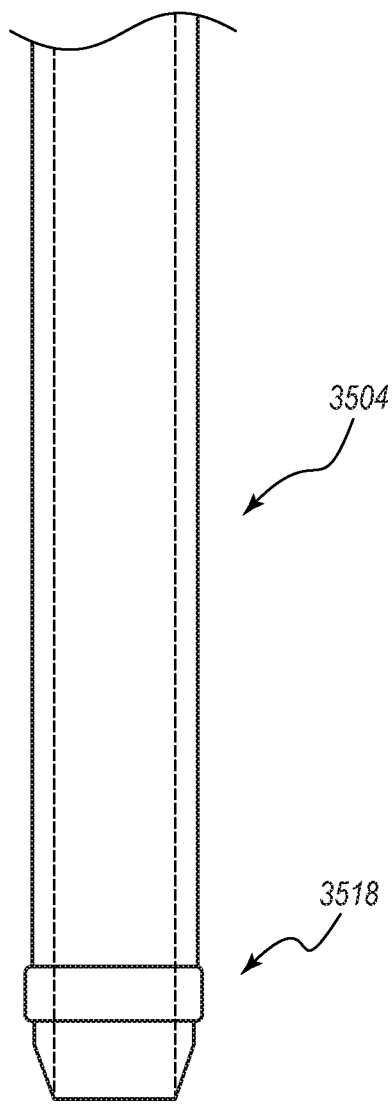
FIG. 40A is an elevation view of a distal end of another embodiment of a catheter assembly that includes a differently shaped and differently oriented positioning element that is depicted in an undeployed state.
Figure 40B:
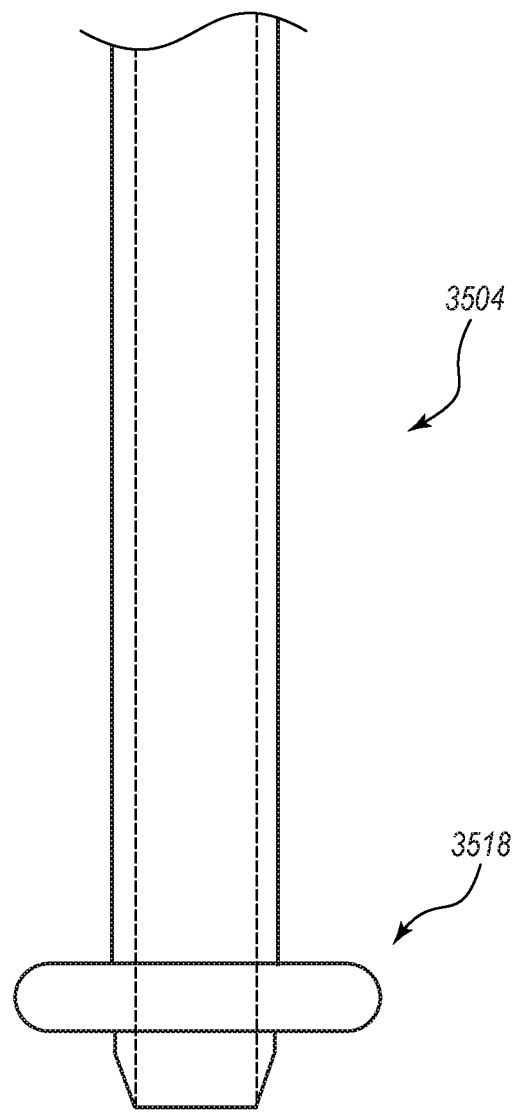
FIG. 40B is another elevation view of the distal end of the catheter assembly of FIG. 40A that depicts the positioning element in a deployed state.

FIG. 40A is an elevation view of a distal end of another embodiment of a catheter assembly 3504 that includes a differently shaped and differently oriented positioning element 3518 that is depicted in an undeployed state. FIG. 40B is another elevation view of the distal end of the catheter assembly 3504 that depicts the positioning element in a deployed state. When deployed, the positioning element 3518 is substantially donut-shaped. The positioning element 3518 is also closer to the distal end of the catheter assembly 3504. In some embodiments, the catheter assembly 3504 can be particularly well-suited for use with a sheath and/or an endoscope, such as, for example, those previously described. The positioning element 3518 may be advanced just beyond a distal tip of the sheath or endoscope before being deployed, in some instances.

Figure 41:
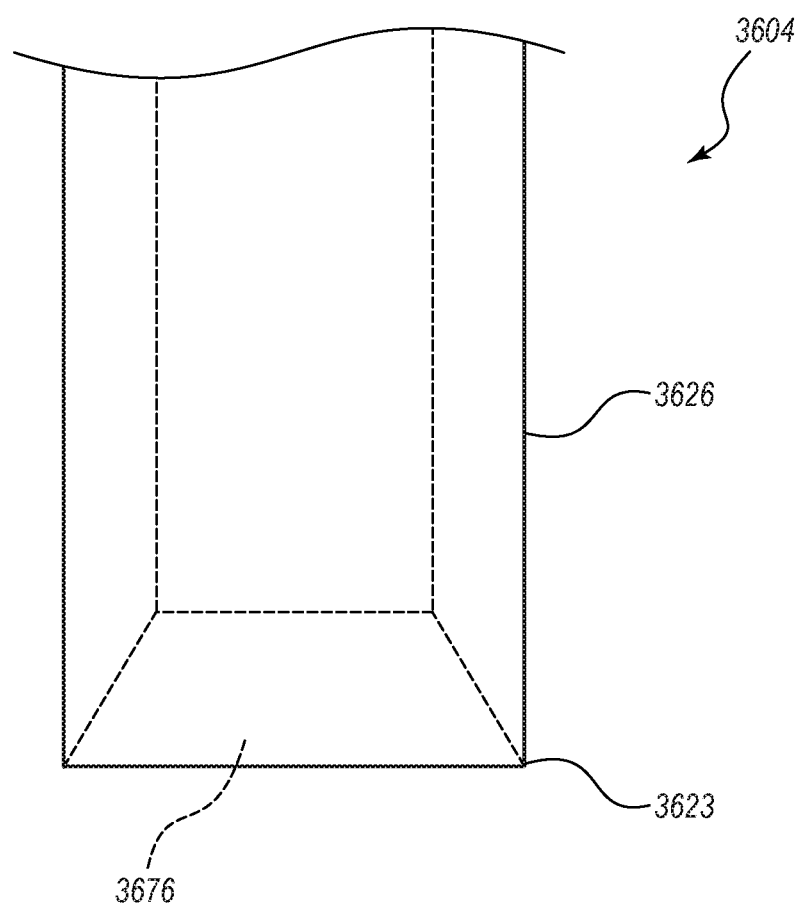
FIG. 41 is an elevation view of a distal end of another embodiment of a catheter assembly that depicts a distal tip of a catheter that includes an internal bevel.

FIG. 41 is an elevation view of a distal end of another embodiment of a catheter assembly 3604 that depicts a distal tip 3623 of a catheter 3626 that includes an internal bevel 3676. For example, the internal bevel 3676 may be formed as a conical chamfer.

Figure 42:
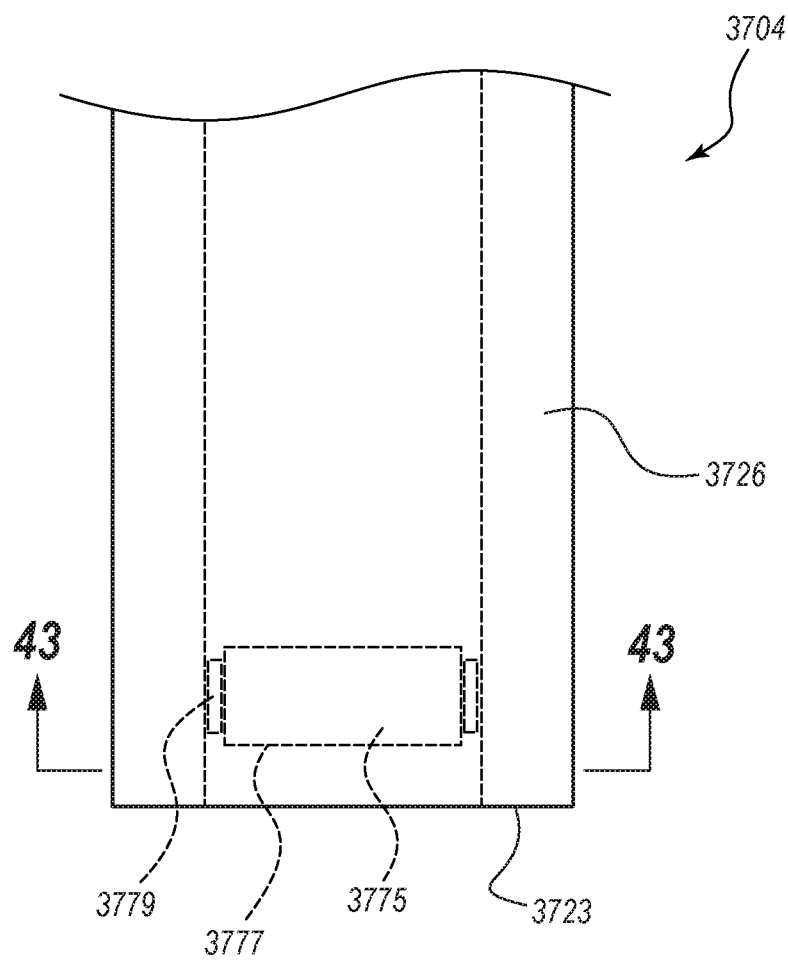
FIG. 42 is an elevation view of a distal end of another embodiment of a catheter assembly that depicts a distal tip of a catheter that is substantially flat and that includes a cutting element recessed from the distal tip within a lumen of the catheter.
Figure 43:
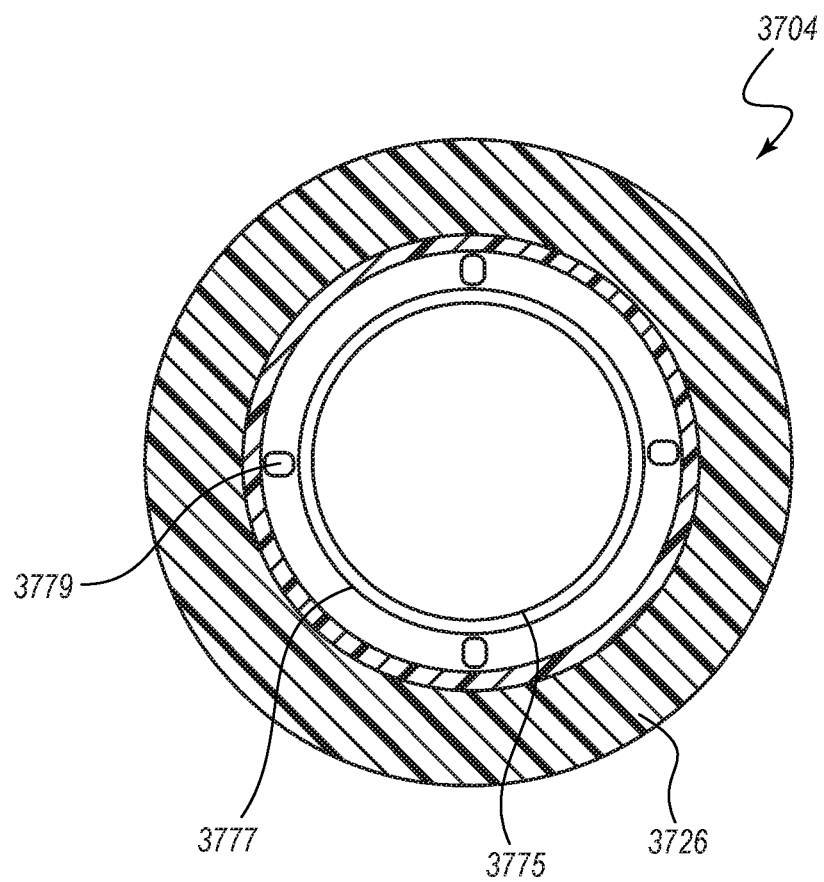
FIG. 43 is a cross-sectional view of the catheter assembly of FIG. 42 taken along the view line 43-43 in FIG. 42.

FIGS. 42 and 43 depict a distal end of another embodiment of a catheter assembly 3704 that includes a catheter 3726 that has a distal tip 3723 that is substantially flat. The catheter assembly 3704 includes a cutting element 3775, such as a blade, that is recessed from the distal tip 3723 within a lumen of the catheter 3726. The cutting element 3775 includes a cutting edge 3777, which is substantially circular in the illustrated embodiment. The cutting element 3775 is attached to the catheter 3726 via a plurality of brackets or supports 3779. A cutting area of the cutting edge 3777 can be smaller than an inner diameter of a lumen of the catheter 3726.

Figure 44:
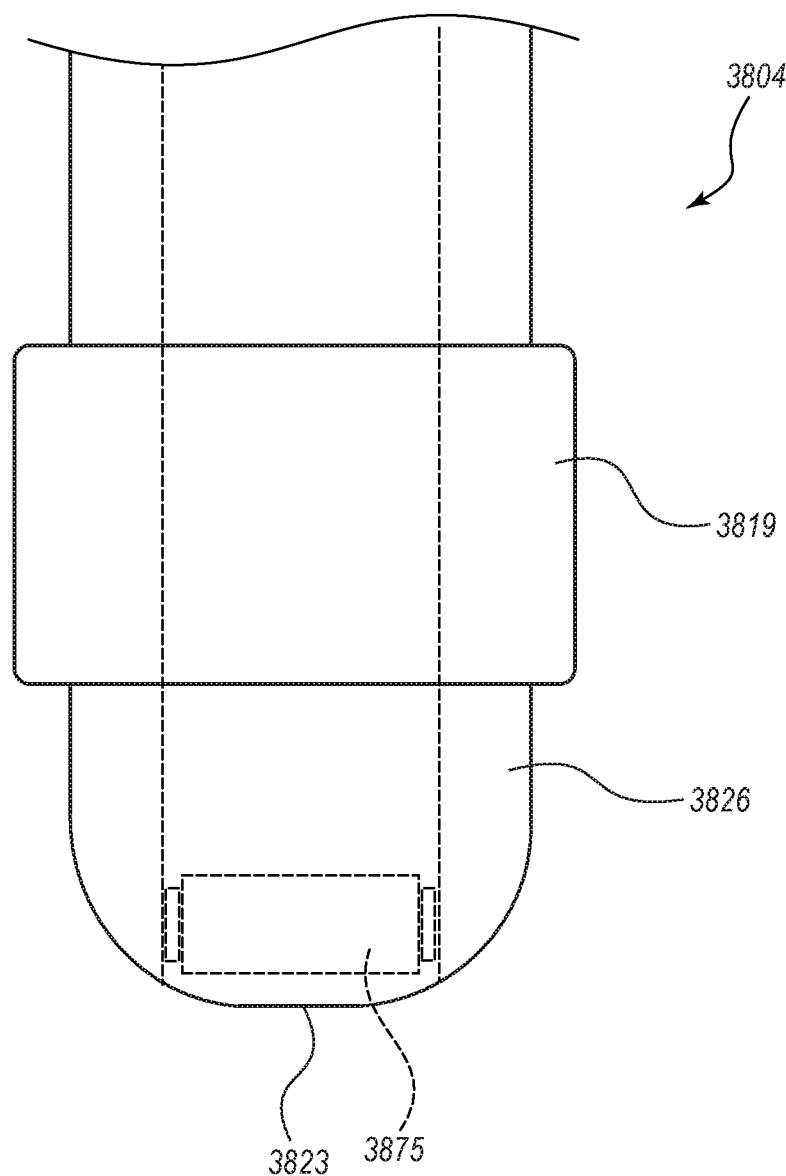
FIG. 44 is an elevation view of a distal end of another embodiment of a catheter assembly that depicts a distal tip of a catheter that is substantially rounded and that includes a cutting element recessed from the distal tip within a lumen of the catheter.

FIG. 44 is an elevation view of a distal end of another embodiment of a catheter assembly 3804 that depicts a distal tip 3823 of a catheter 3826 that is substantially rounded and that includes a cutting element 3875 that is recessed from the distal tip 3823 within a lumen of the catheter. The catheter assembly 3804 further includes a positioning element or centering balloon 3819, which can function similarly to other embodiments described herein. The rounded tip 3823 may be substantially atraumatic to the esophagus. The recessed cutting element 3875 may further aid in preventing inadvertent damage to the esophagus. The centering balloon 3819 may likewise prevent inadvertent damage to the esophagus when deployed. As with other embodiments described herein, the catheter assembly 3804 may be used with or without a sheath or endoscope, in various embodiments. Catheter assemblies such as the assembly 3804 may also be referred to as catheter systems.

Figure 45:
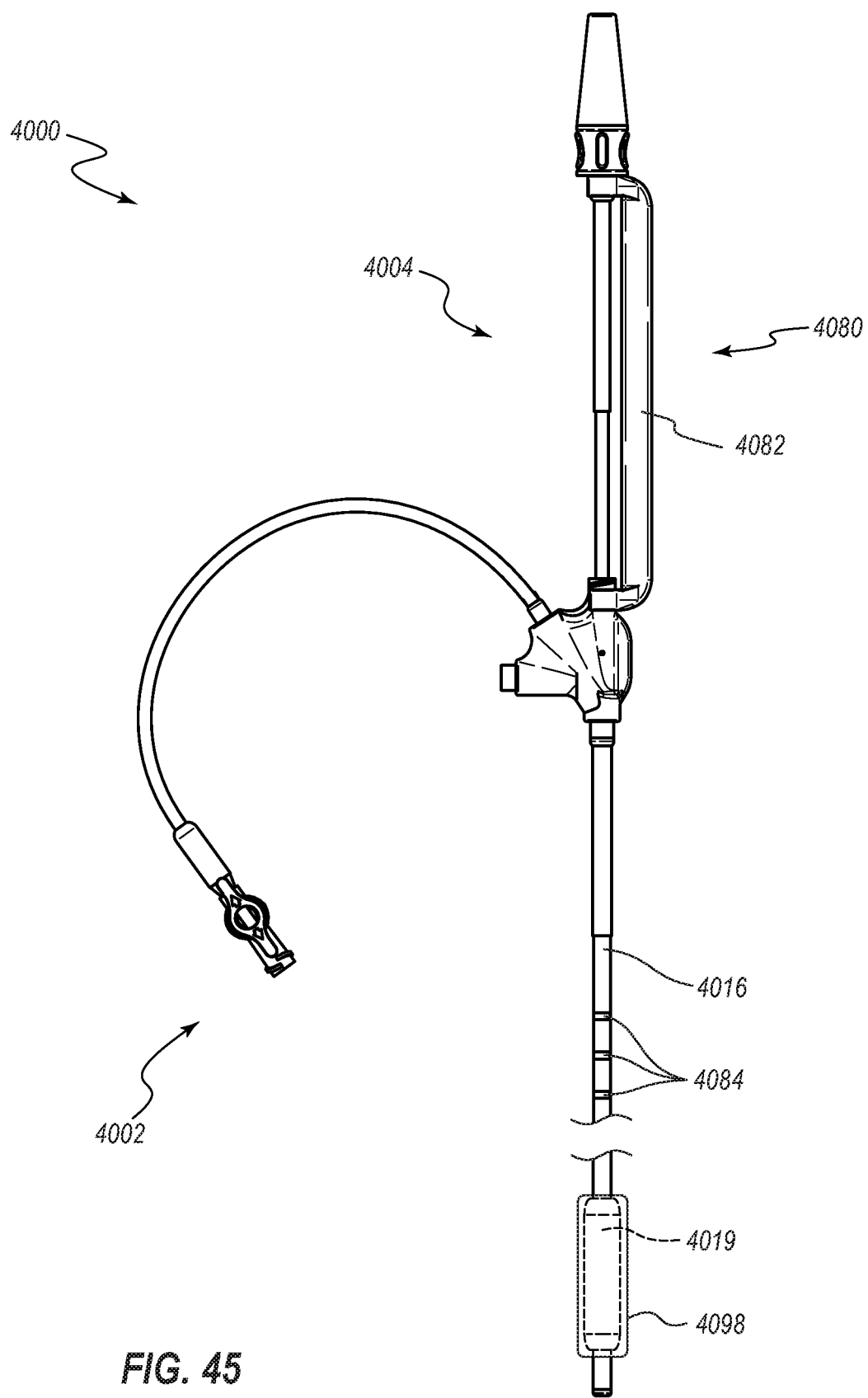
FIG. 45 is an elevation view of another embodiment of a blockage clearing system in an assembled, pre-use, undeployed, packaged, or insertion state.

FIG. 45 is an elevation view of another embodiment of a blockage clearing system 4000 that can resemble blockage clearing systems described above (e.g., the systems 3000, 3200) in certain respects. Accordingly, like features are designated with like reference numerals, with the leading digits incremented to "40." Relevant disclosure set forth above regarding similarly identified features thus may not be repeated hereafter. Moreover, specific features of the system 4000 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 4000 and components thereof. Any suitable combination of the features and variations of the same described with respect to the systems 3000, 3200 can be employed with the system 4000, and vice versa. More generally, any suitable combination of like-numbered components herein is contemplated. Thus, for example, any of the positioning element arrangements 3018, 3118, 3218, 3318, 3418, 3518, 3819 disclosed above, and the positioning element arrangements described hereafter, may be used in place of any of the other positioning elements, mutatis mutandis. This pattern of disclosure applies equally to further embodiments depicted in subsequent figures and described hereafter, wherein the leading digits may be further incremented.

The system 4000 is shown in a pre-use, undeployed, packaged, or insertion state. In particular, the system 4000 is shown in a state in which it may be packaged, or stated otherwise, in a state in which it exists when removed from packaging by a user (e.g., medical practitioner) for insertion into a patient. The system 4000 can include a sheath assembly 4002 and a catheter assembly 4004, such as like-numbered features previously disclosed. The sheath assembly 4002 is discussed further below with respect to at least FIGS. 46-50, and the catheter assembly 4004 is discussed further below with respect to at least FIGS. 51-53.

The system 4000 further includes a retainer or spacer 4080 that can maintain a fixed relative orientation of the sheath assembly 4002 and the catheter assembly 4004. Stated otherwise, the spacer 4080 can maintain a fixed longitudinal relationship, such as a fixed longitudinal separation, between hubs of the sheath assembly 4002 and the catheter assembly 4004. Maintenance of such a fixed relationship between the hubs can likewise maintain a fixed longitudinal relationship between the distal tips of the sheath assembly 4002 and the catheter assembly 4004. For example, as further discussed below, the spacer 4080 can ensure that a distal tip of the catheter assembly 4004, which may comprise a sharpened cutting tip, is positioned at an interior of the sheath assembly 4004 (e.g., is proximally recessed relative to a distal tip of the sheath assembly 4004) when the spacer 4080 is in place. Such an arrangement may be useful to ensure that the cutting surface of the catheter does not inadvertently come into contact with the anatomy of a patient as the system 4000 is being introduced into the patient (e.g., into the esophagus of the patient). Accordingly, in some instances, the system 4000 may be provided in the assembled state shown with the spacer 4080 in place. For example, the system 4000 may be packaged with the spacer 4080 positioned in engagement with the sheath assembly 4002 and the catheter assembly 4004.

In the illustrated embodiment, the spacer 4080 is formed as a clip 4082 that is selectively attachable to and detachable from specific regions of the sheath assembly 4002 and the catheter assembly 4004. In other embodiments, the clip 4082 may only be selectively detachable from the sheath assembly 4002 and the catheter assembly 4004. For example, in some embodiments, portions of the clip 4082 may be permanently attached to the sheath assembly 4002 and the catheter assembly 4004, respectively, and a further portion of the clip 4082 may permanently detach from the portions that are attached to the sheath assembly 4002 and the catheter assembly 4004 to permit relative movement of the sheath assembly 4002 and the catheter assembly 4004. In some instances, the clip 4082 may be provided with the system 4000 in an initial or pre-deployment state (e.g., a packaged state), and may be used during an initial insertion of the system 4000 into the patient and into contact with a blockage, such as a food impaction. The detachable portion of the clip 4082 (e.g., the clip 4082 in its entirety or a detachable portion thereof) may then be removed to permit relative longitudinal movement of the sheath assembly 4002 and the catheter assembly 4004, as discussed further below.

Figure 46:
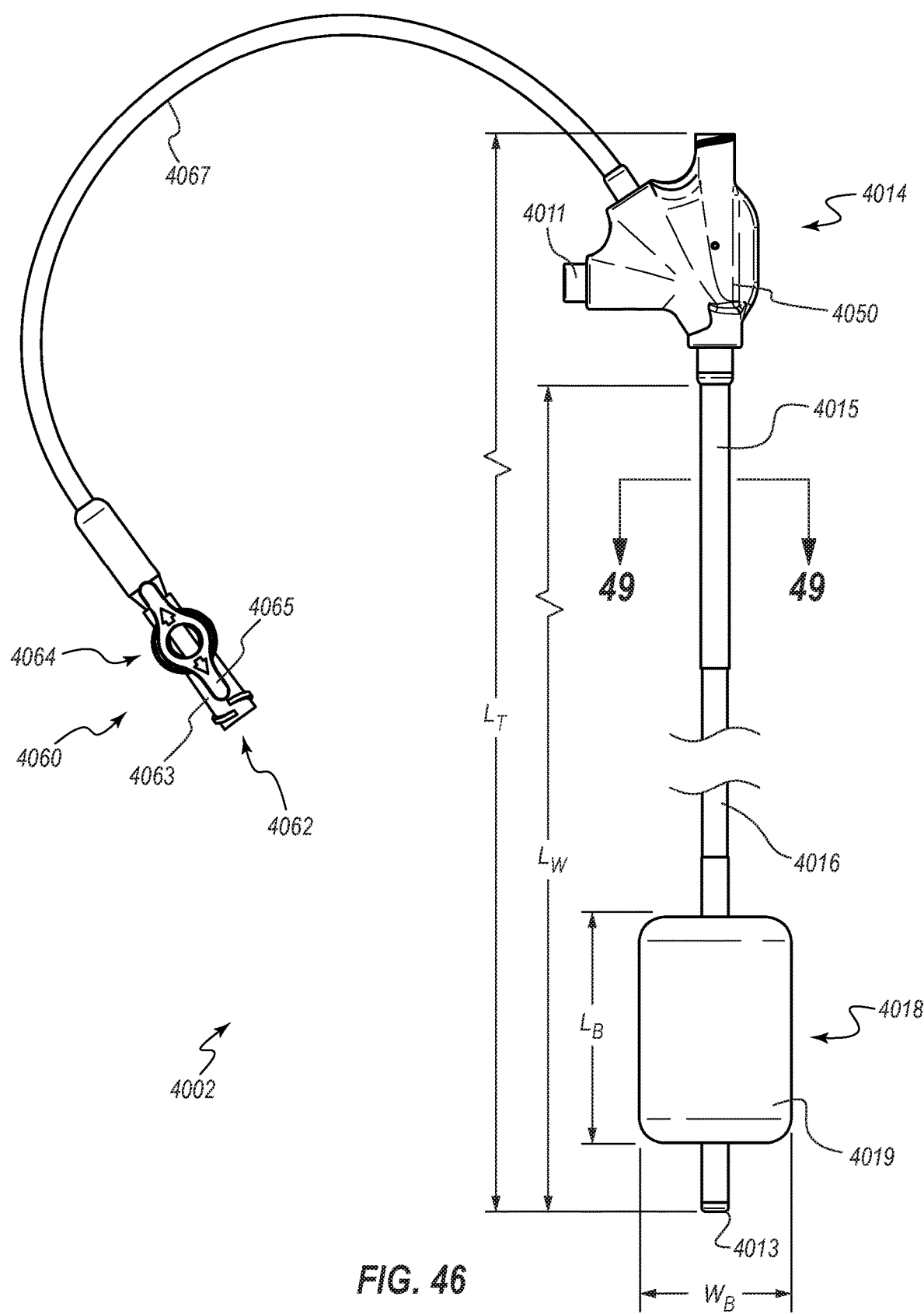
FIG. 46 is an elevation view of an embodiment of a sheath assembly of the blockage clearing system of FIG. 45, the sheath assembly being shown in a deployed state.

FIG. 46 is an elevation view of the sheath assembly 4002 in a deployed state. As with other sheath assemblies previously discussed (e.g., the sheath assemblies 3002, 3202), the sheath assembly 4002 can include an inflation port 4060, which can include a connector 4062, such as a luer fitting 4063. The inflation port 4060 can further include a stopcock 4064, which can be transitioned between open and closed states via a knob or lever 4065. The inflation port 4060 can be formed of any suitable materials. For example, in some embodiments, the inflation port 4060 comprises polycarbonate.

As with other embodiments described herein, the inflation port 4060 can be coupled with a sheath hub 4014 in any suitable manner. In the illustrated embodiment, the inflation port 4060 is coupled to an extender 4067, such as tubing of any suitable construct, and the extender 4067 is coupled to the hub 4014. The extender tubing can comprise any suitable material. For example, in some embodiments, the tubing comprises TYGON®, available from Saint-Gobain Performance Plastics. The extender 4067 can be attached to a connector portion of the stopcock 4064 in any suitable manner.

The hub 4014 can include a housing 4050, which is discussed further below with respect to FIGS. 47 and 48. In some embodiments, a pressure regulation valve 4011 is coupled with the housing 4050. In particular, in the illustrated embodiment, the pressure regulation valve 4011 is directly connected to the housing 4050. The hub 4014 can further be coupled with a sheath 4016 and a strain relief sleeve 4015. The pressure regulation valve 4011 may also be referred to as a pressure regulator.

As with other embodiments disclosed herein, the sheath 4016 can be coupled with a positioning element 4018, such as an inflatable balloon 4019. In some embodiments, the sheath 4016 can include a soft or atraumatic distal tip 4013.

As with the inflation port 3060 discussed above, the inflation port 4060 may also be referred to as an actuator. As further discussed below, the inflation port 4060 is configured to be actuated to achieve deployment of the positioning element 4018, and can be further actuated to achieve retraction of the positioning element 4018.

With reference again to FIG. 45, in some embodiments, the sheath 4016 can include one or more depth indicia or indicators 4084. The indicators 4084 can comprise any suitable marking or other signaling element to provide a visual cue to a user to indicate a depth to which the distal tip of the sheath assembly 4002 has been inserted into a patient. For example, the one or more indicators 4084 can be printed or may be formed as laser markings. In some embodiments, one of the indicators—for example, the distalmost indicator 4084—may indicate a minimum depth to which the distal tip of the sheath assembly 4002 should desirably be inserted prior to deployment of the positioning element 4018. For example, in some embodiments, the minimum depth indicator 4084 is positioned, e.g., 25 centimeters from the distal tip of the sheath 4016. A practitioner may use the minimum depth indicator 4084 to ensure that the distal tip of the sheath 4016 has been inserted to a sufficient depth past the incisors of the patient, which can ensure that the positioning element 4018 is not deployed within the pharynx of the patient. In various embodiments, the minimum depth indicator 4084 may be closer to or further from the distal tip of the sheath 4016 than 25 centimeters. In some instances, the minimum depth indicator 4084 is selected to ensure that the pharynx of any patient, regardless of patient size or anatomy variation, will be avoided when the positioning element 4018 is deployed.

Figure 47:
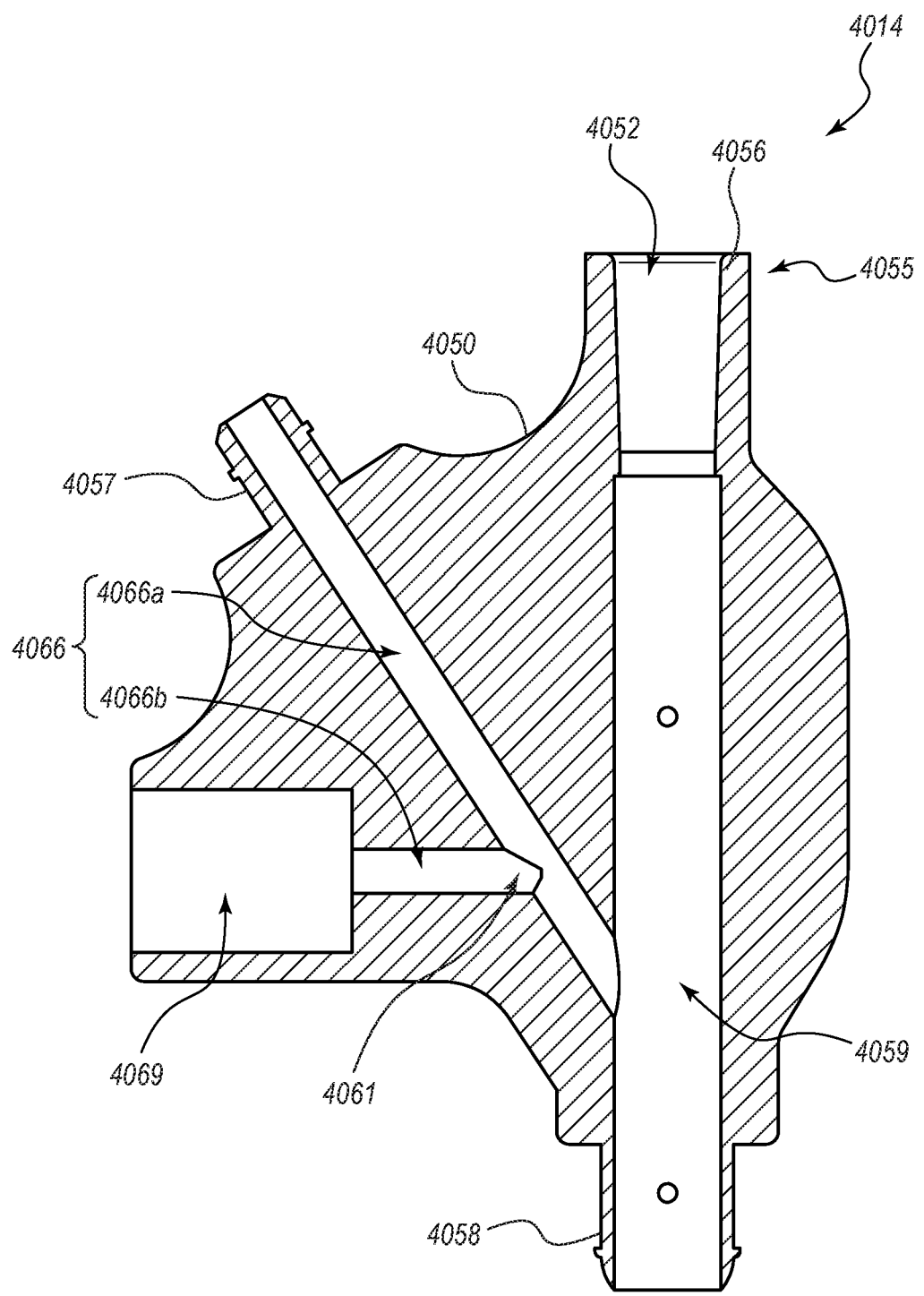
FIG. 47 is a cross-sectional view of a hub of the sheath assembly of FIG. 46.
Figure 48:
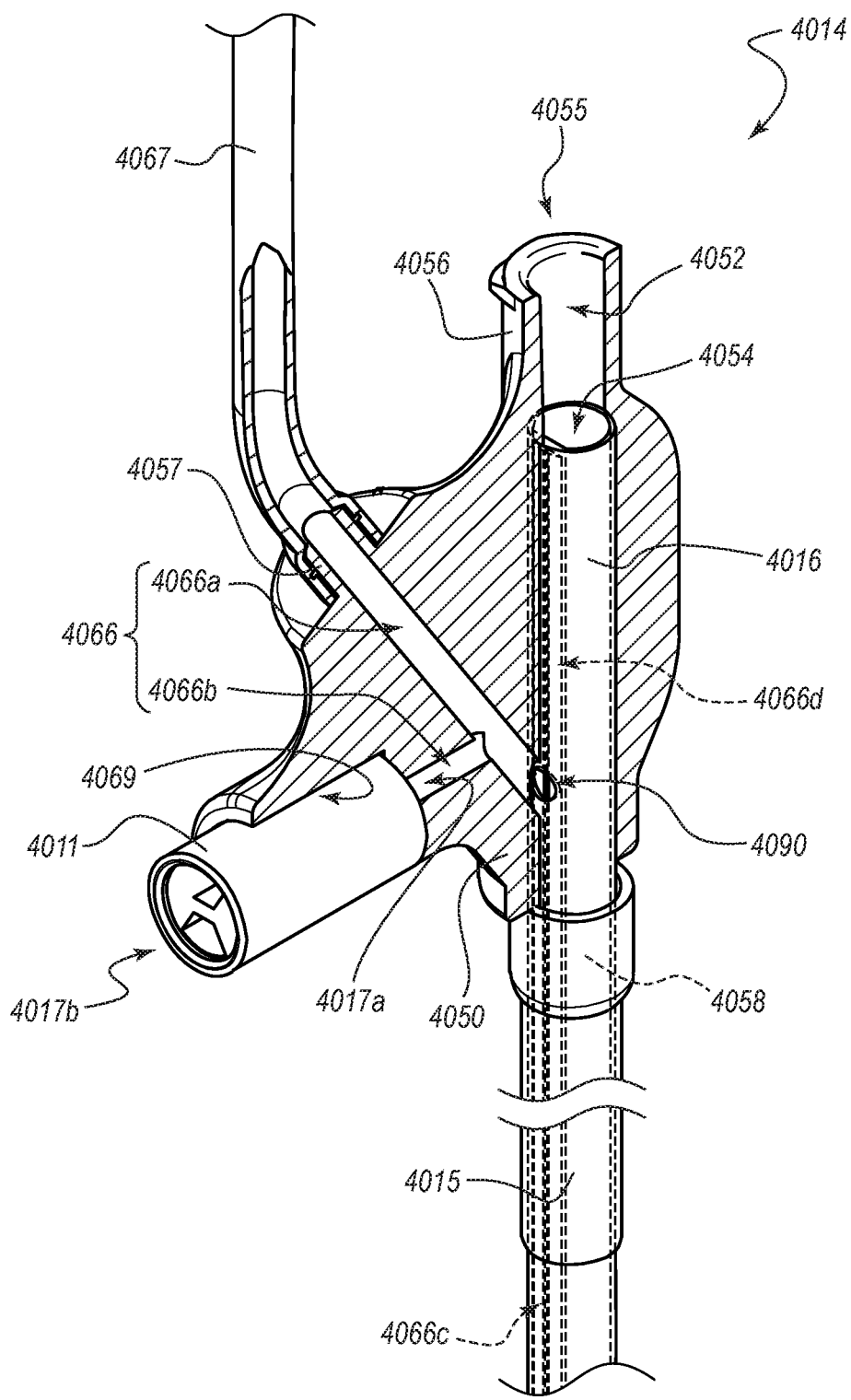
FIG. 48 is a partial cross-sectional view of a portion of the sheath assembly that includes the hub, when the assembly is in an assembled state.

With reference to FIGS. 47 and 48, the hub 4014 can include a housing 4050, which can be formed in any suitable manner. For example, the housing 4050 may be an injection-molded plastic component. In some embodiments, the housing 4050 comprises polycarbonate.

The housing 4050 can define a connector 4055 at a proximal end thereof. For example, in some embodiments, the connector 4055 comprises a luer fitting 4056. The connector 4055 can permit selective coupling with any suitable medical device to provide the medical device with access to an instrument delivery lumen 4054 defined by the sheath 4016 (see FIG. 49). For example, if a practitioner desires to flush the instrument delivery lumen 4054 of the sheath 4016, a flushing syringe could be coupled with the connector 4055 and fluid dispensed through the instrument delivery lumen 4054.

The connector 4055 portion of the housing 4050 can define an entry passage or guide 4052. In the illustrated embodiment, the guide 4052 is substantially funnel shaped, which can facilitate insertion of a distal end of a catheter portion of the catheter assembly 4004 into the instrument delivery lumen 4054 of the sheath 4016. In particular, in the illustrated embodiment, the guide 4052 defines a luer taper that decreases in diameter in the distal direction.

The housing 4050 can further define a connector 4057, such as a flanged or ribbed post, or the like, to which the extender 4067 can be attached in any suitable manner. Similarly, the housing 4050 can define a connector 4058, such a flanged or ribbed post, or the like, to which the strain relief sleeve 4015 can be attached in any suitable manner. For example, as shown in FIG. 48, in the illustrated embodiment, the extender 4067 is fitted over the connector 4057 and the strain relief sleeve 4015 is fitted over the connector 4058 to achieve said attachments.

The housing 4050 can define a sheath receptacle 4059 into which a proximal end of the sheath 4016 can be received. The sheath 4016 can be inserted into the sheath receptacle 4059 until the proximal end contacts a ledge at the proximal end of the receptacle. The proximal end of the sheath 4016 thus may be at or slightly below a distal end of the guide 4052 when the sheath 4016 has been secured to the housing 4050.

The housing 4050 can further define an inflation channel or lumen 4066a that extends through the connector 4057 and that terminates at and is in fluid communication with the sheath receptacle 4059. The housing 4050 can further define an inflation channel or lumen 4066b that extends from a valve receptacle 4069 to the lumen 4066a. In particular, the lumen 4066b intersects the lumen 4066 at a junction 4061. Stated otherwise, fluid communication between the lumens 4066a, 4066b is established at the junction 4061. The lumens 4066a, 4066b are in fluid communication with each other and define separate branches of a unitary fluid passageway defined by the housing 4050. Stated otherwise, the channels 4066a, 4066b may be considered to be, and may also be referred to as, separate branches of a unitary inflation passageway or inflation lumen 4066, of which a proximal end is defined by the housing 4050 and a distal end is defined by the sheath 4016. That is, as with other embodiments herein, and as previously noted, the sheath assembly 4002 can include multiple lumens for expanding the balloon 4019, including one or more lumens that extend through the sheath 4016. All of the lumens may be interconnected or in fluid communication with each other, and may collectively define the fluid passageway or inflation lumen 4066.

Figure 49:
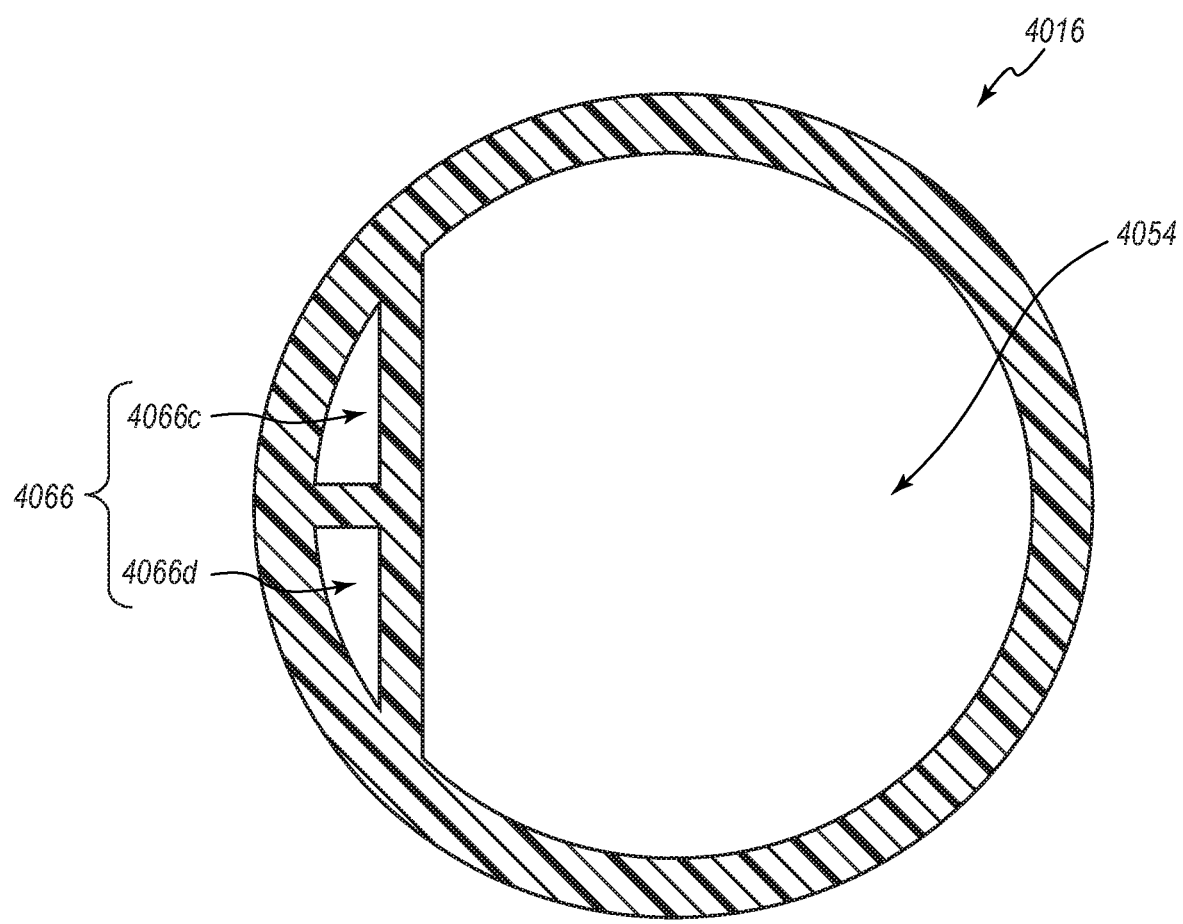
FIG. 49 is a cross-sectional view of a sheath of the sheath assembly of FIG. 46 taken along the view line 49-49 in FIG. 46 (not necessarily to scale)

With reference to FIG. 49, in the illustrated embodiment, the sheath 4016 defines two separate inflation lumens 4066c, 4066d that are each in fluid communication with the inflation lumen 4066a defined by the housing 4050 at or near their proximal ends, and further, are in fluid communication with an interior of the balloon 4019 at or near their distal ends. The inflation lumens 4066c, 4066d define the distal end of the inflation passageway or inflation lumen 4066 of the sheath assembly 4002. As previously noted, in some embodiments, it can be advantageous for the sheath 4016 to define two or more inflation lumens, such as, for example, for purposes of redundancy in the event that one of the lumens 4066c, 4066d is inadvertently blocked (e.g., due to kinking of the sheath 4016). Thus, even if one lumen 4066c, 4066d becomes obstructed, the other can permit inflation or deflation of the balloon 4019.

Again, as previously mentioned, the inflation lumen 4066 can be a unitary lumen or fluid pathway or passageway that includes a plurality of interconnected lumens or branches 4066a, 4066b, 4066c, 4066d. In the illustrated embodiment, the inflation lumens 4066a, 4066b are connected and in fluid communication with each other at the junction 4061. Further, the inflation lumens 4066c, 4066d are in fluid communication with the distal end of the inflation lumen 4066a at their proximal ends, and are in fluid communication with an interior of the balloon 4019 at their distal ends. In this manner, a pressure within the balloon 4019 and within any of the inflation lumens 4066a, 4066b, 4066c, 4066d can be substantially the same at any given time. Stated otherwise, the inflation lumens 4066a, 4066b, 4066c, 4066d and the balloon 4019 can be pressurized substantially in unison, or may increase in pressure substantially concurrently and/or substantially at the same rate during deployment of the balloon 4019.

For example, in some instances, an air-filled syringe can be coupled with the connector 4062. The stopcock 4064 can be oriented in an open state (e.g., the lever 4065 can be rotated to the open state). To deploy the balloon 4019, a plunger of the syringe can be depressed. This can cause air to flow from the syringe, through the stopcock 4064, through the extender 4067, into the inflation lumen 4066a, and from the inflation lumen 4066a into the inflation lumen 4066b, and further, into the inflation lumens 4066c, 4066d of the sheath 4016 and from thence into the balloon 4019. Once air has passed into all of these cavities, pressurization in each of the branches of the inflation lumen 4066 and within the balloon 4019 can proceed substantially in unison as more air is urged from the syringe and, after full deployment of the balloon 4019 (which, in some embodiments, may be non-compliant or semi-compliant) is compressed within a fixed-volume inflation fluid receptacle defined by the inflation lumen 4066 and the expanded balloon 4019.

With reference again to FIGS. 47 and 48, the pressure regulation valve 4011 is attached to the housing 4050 within the valve receptacle 4069. In some instances, the pressure regulation valve 4011 may be secured in place via an adhesive. The pressure regulation valve 4011 can be of any suitable variety. For example, the pressure regulation valve 4011 can comprise a check valve that is configured to permit passage therethrough of a fluid (e.g., air) at or above a cracking pressure. Any suitable commercially available or other variety of check valve is contemplated. For example, in some embodiments, a commercially available cartridge check valve or pressure relief valve is used. The check valve 4011 is positioned such that an entry port thereof 4017a is in fluid communication with the inflation channel 4066b, and hence with the inflation channel 4066a. More generally, the entry port 4017a of the check valve 4011 is in fluid communication with the inflation passageway or inflation lumen 4066 of the sheath assembly 4002. Further, in the illustrated embodiment, the pressure regulation valve 4011 is oriented such that an exit port 4017b thereof is in fluid communication with an environment external to the housing 4014. The pressure regulation valve 4011 thus can leak inflation fluid (e.g., air) to the environment when a threshold pressure—i.e., the cracking pressure—is reached or exceeded within the inflation lumen 4066 and within the balloon 4019.

Accordingly, the pressure regulation valve can regulate a pressure within the balloon 4019. For example, the pressure regulation valve 4011 can ensure that a pressure within the inflation balloon 4019 does not exceed a preset maximum value, which corresponds with the cracking pressure of the valve. Such an arrangement may be configured to ensure that excess pressure that might injure or otherwise negatively impact the esophagus is not applied to the esophagus.

The pressure regulation valve 4011 is depicted as being in fluid communication with the pressurization or inflation port 4060. In particular, with reference to FIGS. 46 and 48, the pressure regulation valve 4011 is in fluid communication with the inflation lumen 4066 (FIG. 48), the inflation lumen 4066 is in fluid communication with the tubing 4067 (FIG. 48), and the tubing 4067 is in fluid communication with the inflation port 4060 (FIG. 46). The pressure regulation valve 4011 is operationally positioned between the inflation port 4060 and the portion of the inflation lumen 4066 defined by the sheath 4016 (e.g., the inflation lumens 4066c, 4066d, as shown in FIG. 49). Stated otherwise, the pressure regulation valve 4011 is in line with the inflation port 4060 and is in line with the portion of the inflation lumen 4066 defined by the sheath 4016 (e.g., the inflation lumens 4066c, 4066d). In particular, in the illustrated embodiment, the pressure regulation valve 4011 is fluidly coupled to the inflation lumen 4066 at a position that is in line with or is between the inflation port 4060 and the portion of the lumen 4066 that is defined by the sheath 4016 (e.g., the inflation lumens 4066c, 4066d).

The pressure regulation valve 4011 is coupled with the hub 4014. In particular, in the illustrated embodiment, the pressure regulation valve 4011 is directly attached to the hub 4014.

Any suitable cracking pressure of the pressure regulation valve 4011 is contemplated. The cracking pressure may be relatively low to ensure that the balloon 4019 does not deform the esophagus, does not significantly deform the esophagus, or does not deform the esophagus beyond an acceptable amount (e.g., an amount less than that at which injury might occur). In various embodiments, the cracking pressure, which may also be referred to as the threshold pressure, is no greater than 3 psi, 4 psi, or 5 psi. In one embodiment, the cracking pressure is about 4.5 psi (e.g., may be set at 4.56 psi). In other embodiments, higher cracking pressures may be used, such as cracking pressures no greater than 6, 7, or 8 psi.

One or more of the connections previously described with respect to the sheath assembly 4002 may be further secured with adhesive. For example, any suitable light curing adhesive is contemplated, including, without limitation, MD 204-CTH-F flexible catheter-bonding adhesive, available from Dymax. For example, adhesive may be used to bond the connections between the extender 4067 and each of the stopcock 4060 and the housing 4050, between the sheath 4016 and the housing 4050, between the valve 4011 and the housing 4050, etc.

With reference to FIGS. 46 and 48, the strain relief sleeve 4015 can be positioned over a proximal portion of the sheath 4016 and over the connector 4058 at the distal end of the housing 4050. In some embodiments, the strain relief sleeve 4015 may be heat shrunk in place. Any suitable material for the strain relief sleeve 4015 is contemplated. For example, in some embodiments, the strain relief sleeve 4015 can comprise a polyolefin.

The strain relief sleeve 4015 can reinforce a proximal end of the sheath 4016. For example, in some instances, the strain relief sleeve 4015 can contribute to a columnar strength of the sheath 4016 and can stiffen the sheath 4016. In some embodiments, this stiffening can facilitate insertion of the sheath 4016 into the esophagus of the patient, such as in instances where the sheath 4016 is relatively compliant. In other or further instances, the strain relief sleeve 4015 can inhibit or prevent kinking of the sheath 4016, such as kinking that might otherwise close one or more of the inflation lumens 4066a, 4066b. In some instances, the sheath 4016 is sufficiently long to cover and reinforce regions of the sheath 4016 that may be most prone to bending or kinking, such as a region at or near the connector 4058 and/or a region (which may be the same or a different region) at or near a portion of the sheath 4016 that undergoes maximum bending during insertion of the sheath 4016 into the esophagus, such as to conform to the anatomy between the mouth and the esophagus.

With reference to FIG. 49, the sheath 4016 can be formed in any suitable manner. For example, in some embodiments, the sheath 4016 comprises a tri-lumen extrusion. The sheath 4016 can comprise any suitable material, as previously discussed. In the illustrated embodiment, the sheath 4016 comprises a thermoplastic elastomer, such as PEBAX®. For example, in some embodiments, the sheath 4016 comprises PEBAX® 5533 SA 01 MED. In other or further embodiments, the sheath 4016 can comprise nylon 12 or PEBAX® 7233.

Figure 50:
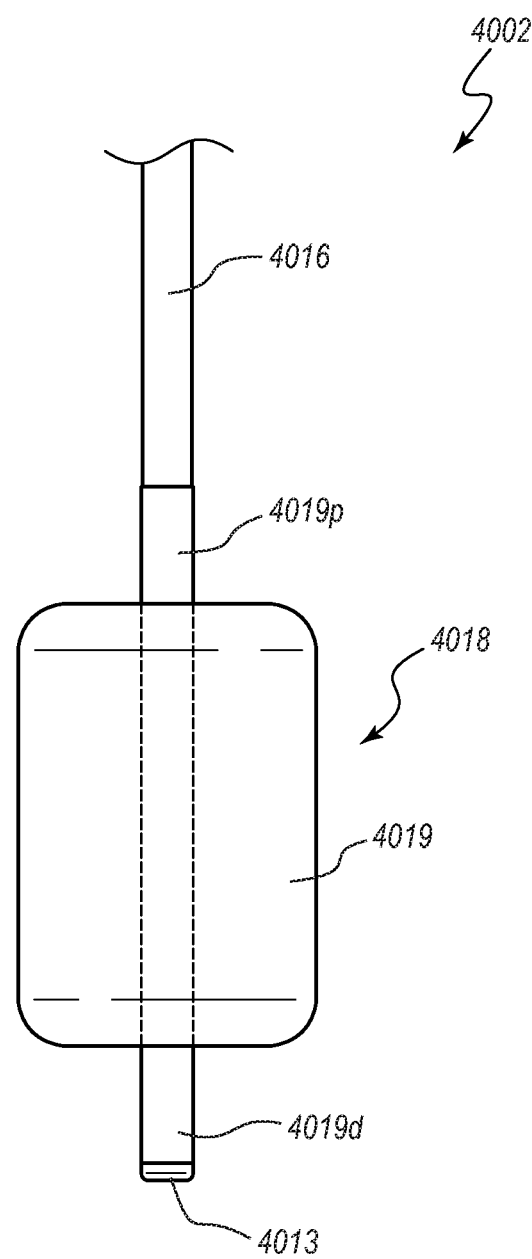
FIG. 50 is an enlarged elevation view of a distal end of the sheath assembly of FIG. 46, which includes a positioning element that is depicted in a deployed state.

With reference to FIG. 50, the atraumatic tip 4013 can be formed in any suitable manner. The tip 4013 can be formed of a material that is softer than the remainder of the sheath 4016. For example, in some embodiments, the sheath 4016 comprises a thermoplastic elastomer, such as PEBAX®, which could be a softer version than is used for the remainder of the shaft, such as, for example, PEBAX® 3533 SA 01 MED. Any suitable manufacturing techniques for forming the tip 4013 are contemplated, such as, for example, reflowing and tipping.

With reference again to FIGS. 47 and 48, the proximal end of the sheath 4016 can be positioned within the receptacle 4059 such that both lumens 4066c, 4066d are oriented toward the inflation lumen 4066a defined by the housing 4050. One or more openings 4090 can be formed through the sidewall of the sheath 4016 into the lumens 4066c, 4066d in a region that aligns with the inflation lumen 4066a of the housing to fluidly couple the lumen 4066a with the lumens 4066c, 4066d. The one or more openings 4090 can be formed in any suitable manner. For example, in some instances, a fixture that includes one or more blades can retain the unfinished sheath 4016 therein and slice through a portion of the sidewall of the sheath 4016 to provide access to each lumen 4066c, 4066d individually (e.g., by forming two longitudinal slices) or to provide access to both of the lumens 4066c, 4066d collectively, such as via a single cut through the sidewall that provides fluid communication into each of the lumens 4066c, 4066d.

As previously discussed, in some embodiments, the sheath 4016 is formed as a thin-walled triple-lumen extrusion having a cross-section such as that depicted in FIG. 49. In some embodiments, the lumens 4066c, 4066d are closed at their proximal and distal ends in any suitable manner, thus permitting the lumens 4066c, 4066d to hold a fluid (e.g., air) therein and withstand pressure increases, such as previously discussed. The proximal and distal ends of the lumens 4066c, 4066d can be closed or sealed, e.g., so as to be fluid-tight and pressure-resistant, in any suitable manner. For example, in some embodiments, the sidewall of the extrusion in the region of the proximal and distal ends of the lumens 4066c, 4066d is heated or reflowed and reshaped to close off the proximal and distal ends of the lumens 4066c, 4066d.

With reference to FIG. 50, one or more openings (not shown) can be formed through the sidewall of the sheath 4016 into the lumens 4066c, 4066d in a region that is internal to an inflatable portion of the balloon 4019. The one or more openings can be formed in manners such as discussed above with respect to the one or more openings 4090 (FIG. 48). Accordingly, the interior of the balloon 4019 can be in fluid communication with the lumens 4066c, 4066d of the sheath 4016, with the lumens 4066a, 4066b of the housing, with the pressure regulation valve 4011, and with the inflation port 4060. The stopcock 4064 of the inflation port can selectively be opened and closed to selectively establish and terminate, respectively, fluid communication between the connector 4063 and the balloon 4019.

Accordingly, when the stopcock 4064 is open, a fluid delivery device (e.g., an air-filled syringe) coupled with the connector 4063 can urge fluid into the balloon 4019 to deploy the balloon 4019. The fluid can fully deploy the balloon 4019. Whether concurrently upon reaching the fully deployed state of the balloon 4019, or whether at some point thereafter due to continued addition of fluid into the balloon 4019, a pressure within the balloon 4019 can reach the threshold value. At this point, if attempts to pressurize the balloon 4019 above the threshold value, the pressure regulation valve 4011 will permit fluid to escape to the environment to maintain the balloon 4019 at the threshold value of pressure. Accordingly, the valve 4011 can maintain the balloon 4019 in the deployed state at a substantially constant pressure, despite attempts to further pressurize the balloon 4019 via the inflation or pressurization port 4060. The stopcock 4064 can be closed to maintain the fluid within the sheath assembly 4002 and maintain the balloon 4019 in the deployed state.

The term "fluid" can refer herein to one or more gases, one or more liquids, or a combination thereof. For example, an inflation fluid used with the balloon 4019 can comprise one or more of air, nitrogen, water, saline solution, etc. In some embodiments, the fluid is air.

In the illustrated embodiment, the balloon 4019 includes a proximal sleeve or extension 4019p and a distal sleeve or extension 4019d. The extensions 4019p, 4019d can be attached to the sheath 4016 in any suitable manner. For example, in some embodiments, the extensions 4019p, 4019d are bonded or otherwise secured to the sheath 4016 to form fluid tight seals at the proximal and distal ends of the balloon 4019.

As previously discussed, in various embodiments, the balloon 4019 is semi-compliant or non-compliant. For example, the balloon 4019 may expand to a predetermined size via application of a first amount of pressure therein, and thereafter may either expand only minimally or not expand at all upon further addition of pressure therein. Stated otherwise, the balloon 4019 may define a preformed shape, such as the shape depicted in FIG. 50, to which it is inflated when deployed.

For example, with reference to FIG. 45, during manufacture, after the balloon 4019 has been secured to the sheath 4016, the balloon 4019 may be deflated (e.g., via application of a vacuum at the inflation port 4060) or otherwise transitioned to a compressed, deflated, retracted, undeployed, wrapped, folded, or packaged state, as shown. A protective sleeve 4098 or other suitable cover may be placed over the balloon 4019 for packaging. When the sheath assembly 4002 is ready for use, the protective sleeve 4098 can be removed and the balloon 4019 can be advanced to the desired position within the esophagus. The balloon 4019 may maintain its low-profile configuration throughout insertion, such as may result from having been contained within the protective sleeve 4098 for an extended period.

The balloon 4019 can then be inflated into contact with the esophagus, in manners such as previously discussed. Throughout the inflation, the balloon 4019 may undergo little or no stretching. Rather, the balloon 4019 may be flexible so as to be compacted or compressed into its pre-use state, and then can be inflated to its preformed shape without, or substantially without, stretching the material of which the balloon 4019 is formed. Any suitable material is contemplated for the balloon 4019. For example, in some embodiments, the balloon 4019 comprises a thermoplastic polyurethane elastomer, such as PELLETHANE®, which is available from Lubrizol. In particular, in some embodiments, the balloon 4019 comprises PELLETHANE® having a Shore A hardness 90. Other materials are also contemplated. In some embodiments, the balloon 4019 may be more compliant and may be configured to stretch into a desired shape when a predetermined pressure is applied therein.

With reference again to FIG. 46, the balloon 4019 can define any suitable shape and configuration. As with other embodiments disclosed herein, the illustrated balloon 4019 is substantially cylindrical with curved edges. The balloon 4019 defines a length $L_B$ and a width $W_B$, which may also be referred to as the diameter of the balloon 4019. In the illustrated embodiment, the length $L_B$ is greater than the width $W_B$. In various embodiments, the length $L_B$ is within a range of from about 1 to about 5 centimeters, from about 2 to about 4 centimeters, or from about 2.5 to about 3.5 centimeters; is no less than about 2, 2.5, 3, 3.5, 4, 4.5 or 5 centimeters; is no greater than about 2, 2.5, 3, 3.5, 4, 4.5, or 5 centimeters; or is about 2, 2.5, 3, 3.5, 4, 4.5, or 5 centimeters. In other or further embodiments, the width $W_B$ is within a range of from about 1.5 to about 3.5 centimeters or from about 2 to about 3 centimeters; is no less than about 1.5, 2, 2.5, 3, or 3.5 centimeters; is no greater than 1.5, 2, 2.5, 3, or 3.5 centimeters; or is about 1.5, 2, 2.5, 3, or 3.5 centimeters. For example, in the illustrated embodiment, the length $L_B$ is 3 centimeters and the width $W_B$ is 2.5 centimeters.

The sheath assembly 4002 can define a total length $L_T$ between its proximal and distal tips, and can further define a working length $L_W$, which may represent a portion of the sheath assembly 4002 that can generally be manipulated for insertion into a patient. The working length $L_W$ may, in some embodiments, desirably be sufficiently long to permit the distal, atraumatic tip 4013 to be inserted sufficiently deep into the esophagus of any of a variety of patients, including those having the largest anatomies, to be able to access a food impaction situated at or near the bottom of the esophagus. In various embodiments, the working length $L_W$ is no less than about 50, 55, 60, 65, or 70 centimeters; is no greater than about 50, 55, 60, 65, or 70 centimeters; or is about 50, 55, 60, 65, or 70 centimeters. In the illustrated embodiment, the total length $L_T$ is 64.5 centimeters and the working length $L_W$ is 60 centimeters.

As previously discussed, a variety of sizes are contemplated for the sheath 4016. In the illustrated embodiment, the sheath 4016 is 12 French. Similarly, a variety of sizes are contemplated for the instrument delivery lumen 4054 of the sheath 4016. In the illustrated embodiment, the minimum inner diameter of the delivery lumen 4054 (e.g., along the horizontal dimension in FIG. 49) is 0.133 inches.

Figure 51:
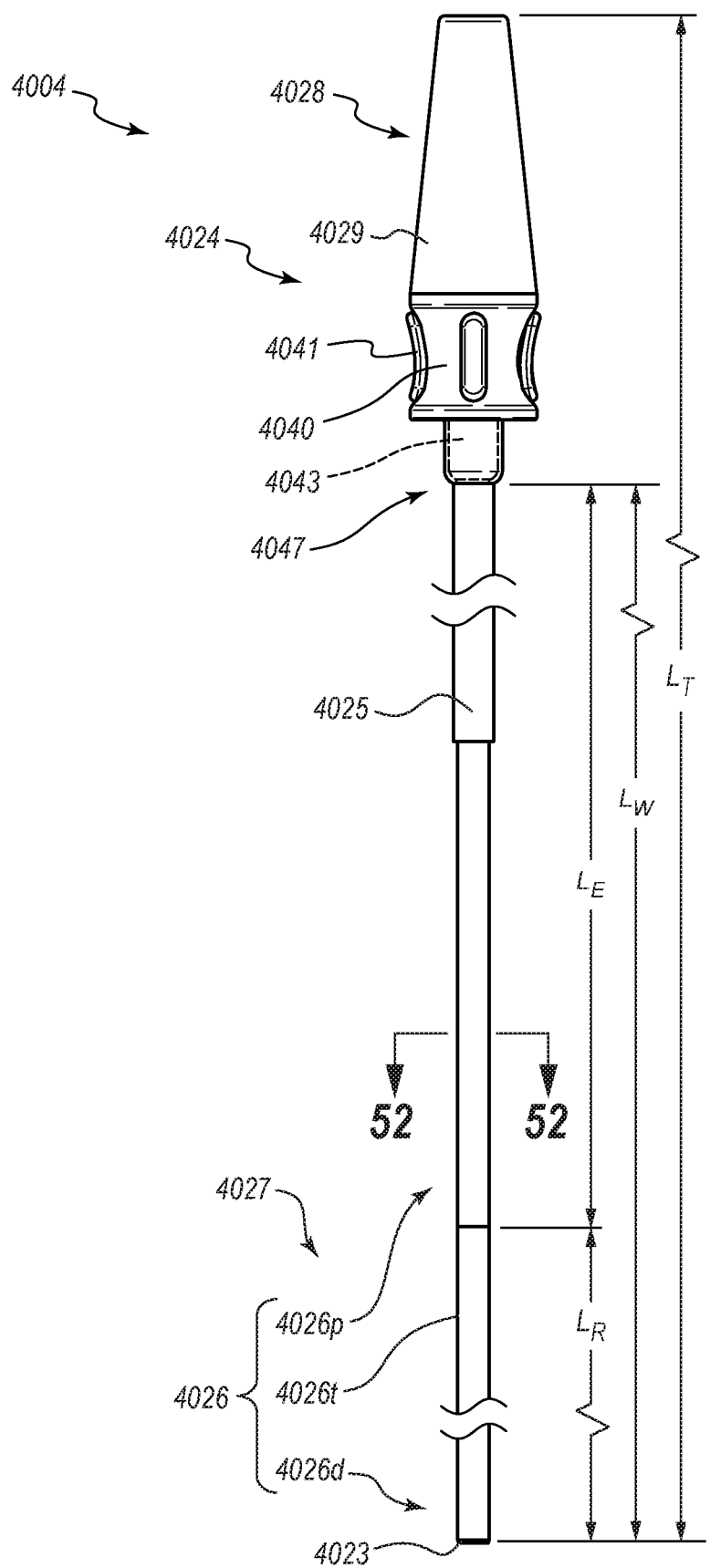
FIG. 51 is an elevation view of an embodiment of a catheter assembly that is compatible with the blockage clearing system of FIG. 45 and/or, in other or further embodiments, is compatible for use with an endoscope.

FIG. 51 depicts a catheter assembly 4004 that can be well suited for use with the sheath assembly 4002. Other embodiments of catheter assemblies disclosed herein are also possible. In the illustrated embodiment, the catheter assembly 4004 includes a catheter hub 4024 that is fixedly secured to a proximal end of a catheter 4026, and is further connected to a proximal end of a strain relief sleeve 4025.

The catheter hub 4024 includes a suction connector 4028 at a proximal end thereof. The suction connector 4028 can be a tapered suction fitting 4029 of any suitable variety, including those presently in use and suitable for connection to a variety of different sizes and constructions of vacuum line tubing. For example, the connector 4028 can be configured for slip fit connection to the vacuum system of a hospital via any suitable tubing. The hub 4024 can further include a handle 4040, which may include grips 4041 for increased traction. The hub 4024 may define a distally projecting connector 4043, similar to the connector 4058 of the sheath hub 4014 (see FIG. 47), through which the catheter 4026 is inserted for connection to an interior of the hub 4014 and over which the strain relief sleeve 4025 is secured.

The various components of the catheter assembly 4004 can be formed of any suitable materials. In the illustrated embodiment, the hub 4024 comprises polycarbonate and the strain relief sleeve 4025 comprises a heat shrink polyolefin.

Figure 52:
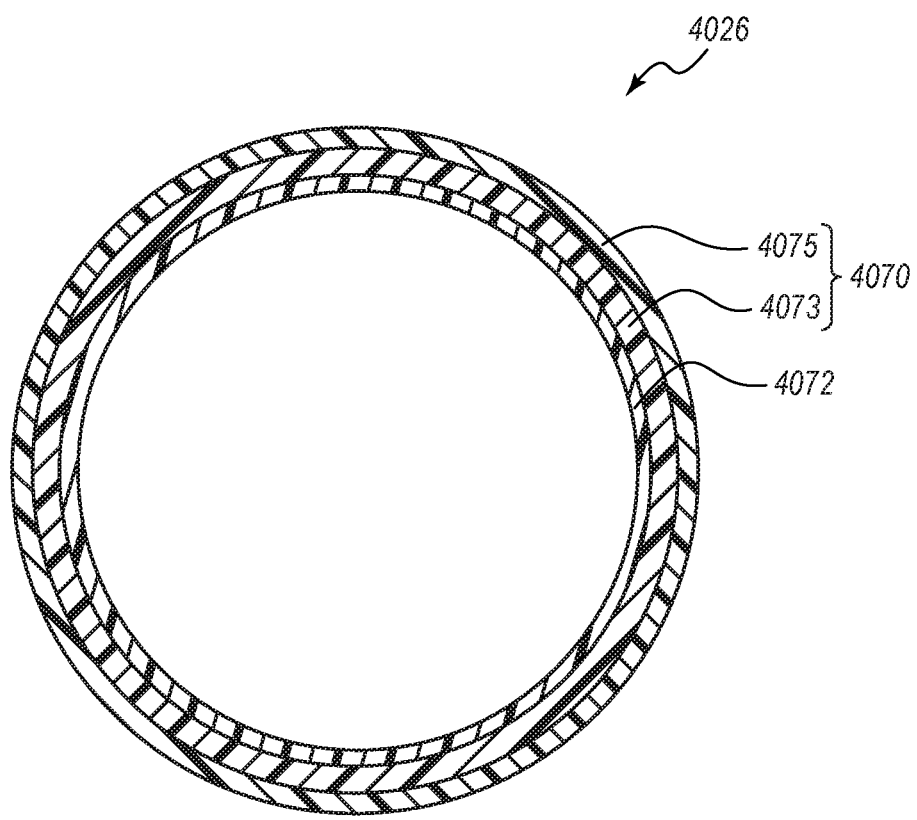
FIG. 52 is a cross-sectional view of a catheter of the catheter assembly of FIG. 51 taken along the view line 52-52 in FIG. 51 (not necessarily to scale)

With reference to FIG. 52, the catheter 4026 can include a lubricious inner layer 4072 of any suitable variety. In the illustrated embodiment, the layer 4072 comprises a PTFE liner. The catheter 4026 can further include a body 4070 that includes a braided material and a polymeric material. In particular, the body 4070 includes a braided layer 4073 and an outer layer 4075 of polymeric material, which can extend into the braided layer 4073. In the illustrated embodiment, the braided layer 4073 comprises a layer of braided 304 stainless steel, and the outer layer 4075 comprises nylon 12. The illustrated embodiment also includes a distal tip 4023, which may include one or more different and/or additional materials from other portions of the catheter. For example, in the illustrated embodiment, the tip may be formed of or include polyethylene terephthalate (PET). Any other suitable composition of the catheter 4026 is contemplated.

Standard methods may be used to manufacture the catheter 4026. For example, the catheter 4026 may be formed via a "stick build" in which the PTFE liner 4072 is placed over a mandrel, the stainless steel is braided over the PTFE liner 4072 to form the braided layer 4073, a single-lumen extrusion of nylon 12 is slid over the braid, and then the materials are heated and reflowed.

With reference again to FIG. 51, the catheter 4026 can include a depth indicator 4027, which can provide information regarding a position of the distal tip 4023 of the catheter 4026 within the sheath assembly 4002. In the illustrated embodiment, the depth indicator 4027 comprises a transition line 4026t between a proximal portion 4026p and a distal portion 4026d of the catheter 4026. In some embodiments, the proximal and distal portions 4026p, 4026d of the catheter are different colors to provide a readily observable visual cue. For example, in one embodiment, the proximal portion 4026p is white and the distal portion 4026d is gray. Any other suitable indicium for the depth indicator 4027 is contemplated. For example, in other or further embodiments, the critical depth can be identified with a printed or laser marking. In the illustrated embodiment, the catheter 4026 can be formed in manners such as previously disclosed, but utilizing two different single-lumen extrusions of nylon 12 each having different colorants. The extrusions can be situated end-to-end over the braided layer 4073 prior to reflowing.

The distal portion 4026d of the catheter 4026 may define a retraction length $L_R$ that is slightly shorter than the total length $L_T$ of the sheath assembly 4002 (see FIG. 46). In this manner, a practitioner may have a visual cue that the distal tip 4023 of the catheter 4026 is safely withdrawn within an interior of the sheath 4016 when, for example, a proximal end of the gray distal portion 4026d of the catheter 4026 is visible outside of the proximal end of the sheath assembly 4002. It can be desirable for the distal tip 4023 to be within the sheath 4016 prior to insertion or repositioning of the system 4000 into or within the patient to ensure that the atraumatic tip 4013 of the sheath 4016 is the leading tip of the system 4000, rather than the sharper coring tip 4023 of the catheter 4026. In various embodiments, the retraction length $L_R$ is shorter than the total length $L_T$ of the sheath assembly 4002 by no less than about 0.4, 0.5, 0.6, 0.7, 0.8 centimeters. For example, in the illustrated embodiment, the retraction length $L_R$ is shorter than the total length $L_T$ of the sheath assembly 4002 by about 0.6 centimeters. In some instances, such an arrangement can ensure that the distal tip 4023 of the catheter 4026 is safely stowed in the sheath 4016 (e.g., is proximally recessed relative to the distal tip of the sheath 4016), while permitting the catheter 4026 to support (e.g., inhibit the kinking or other undesired deformation of) nearly an entire length of the sheath 4016.

Similarly, the proximal portion 4026p of the catheter 4026 and the strain relief sleeve 4025 can define an exposed length $L_E$ of which an entirety should be visible beyond the proximal end of the sheath assembly 4002 to ensure that the distal tip 4023 of the catheter 4026 is safely retracted within the sheath 4016. The exposed length $L_E$ at the proximal end of the catheter 4026 can be slightly longer than an exposable length of the distal end of the catheter 4026 that is permitted to extend past the distal tip 4013 of the sheath 4016 during coring and suctioning. In particular, in some embodiments, the exposed length $L_E$ at the proximal end of the catheter 4026 is longer than the exposable length at the distal end of the catheter 4026 by the same distance to which the distal tip 4023 of the catheter 4026 is retracted from the distal tip 4013 of the sheath 4016 when the interface of the proximal and distal portions 4026p, 4026d of the catheter 4026 is flush with the proximal tip of the sheath assembly 4002.

As discussed elsewhere herein, in some instances, it can be desirable for the exposable length at the distal end of the catheter 4026 to be relatively short to ensure that the distal tip 4013 of the catheter does not inadvertently come into contact with the esophagus. For example, in various embodiments, the exposable length may be no greater than 0.75, 1.0, 1.25, 1.5, or 2.0 inches. In some embodiments, such as illustrated, the exposed length $L_E$ can include at least a portion of a length of the strain relief sleeve 4025. In other embodiments, a proximal end of the exposed length $L_E$ terminates substantially at a proximal end of a portion of the catheter 4026 that is not covered by the strain relief sleeve 4025.

As with other embodiments disclosed herein, the catheter assembly 4004 can include a stopping region 4047, which can interact with the sheath hub 4014 to delimit an amount of distal movement of the catheter 4026 beyond the distal tip 4013 of the sheath 4016. In the illustrated embodiment, the stopping region 4047 is the diametrically or laterally expanded region defined by the connector 4043 portion of the catheter hub 4024 and the expanded portion of the strain relief sleeve 4025 that is connected thereto. The stopping region 4047 can interfere with a proximal end of the connector 4055 or may enter into and interfere with a proximal portion of the guide 4052 within the connector 4055, each of which is defined by the housing 4050 (see FIG. 47), as the catheter assembly 4004 is advanced distally through the sheath assembly 4002.

The catheter assembly can define a total length $L_T$ and a working length $L_W$. In the illustrated embodiment, which is merely one illustrative example, the total length $L_T$ is 77.5±1 centimeters and the working length $L_W$ is 72.8±1 centimeters. The exposed length $L_E$ is 8.9±0.05 centimeters. Other dimensions are possible and are contemplated by the present disclosure.

Figure 53:
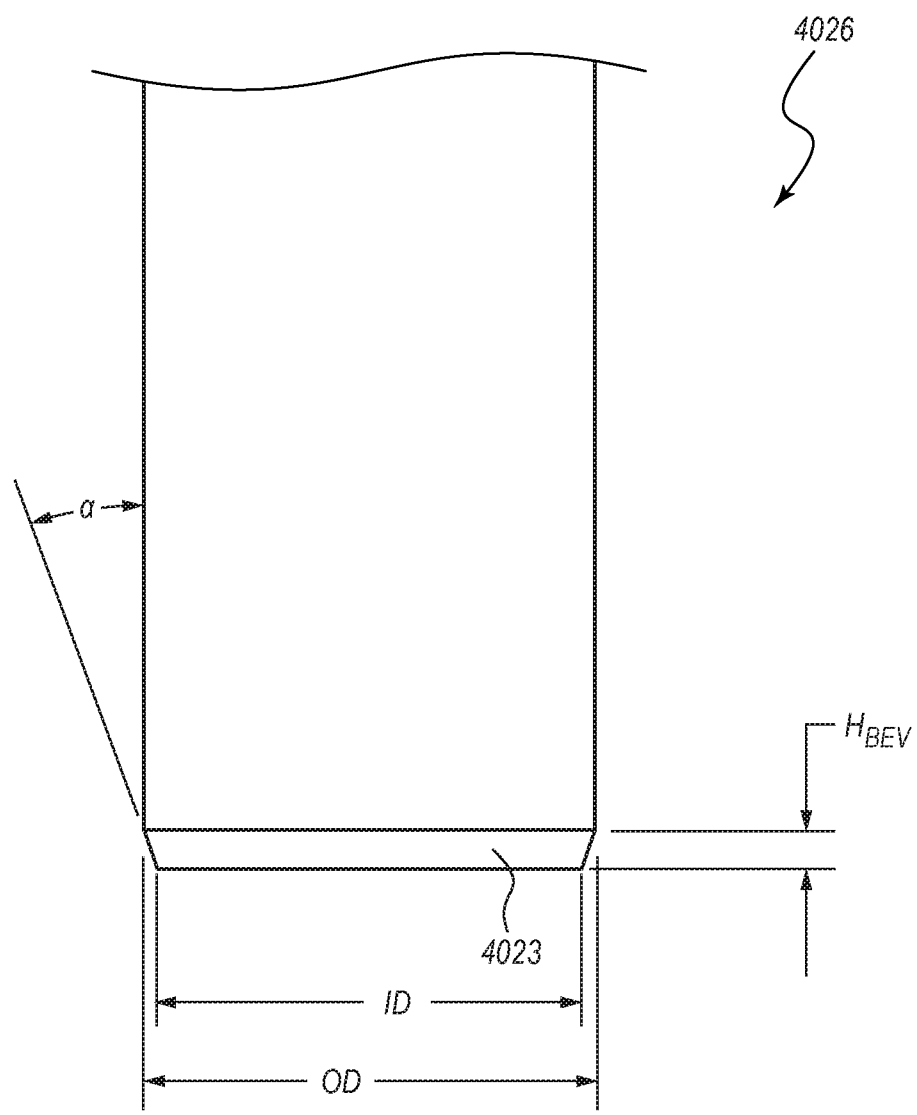
FIG. 53 is an enlarged elevation view of a distal end of the catheter.

With reference to FIG. 53, an outer diameter OD of the illustrated catheter 4026 is 0.124±0.005 inches and an inner diameter ID of the catheter 4026 is 0.105±0.005 inches. The outer diameter OD may also be referred to as a maximum diameter of the catheter 4026. A height $H_{BEV}$ of the bevel at the distal tip 4023 is 0.025±0.005 inches. An angle α defined by the bevel, relative to an axial or longitudinal dimension of the catheter 4026, is 20.0±0.05 degrees. Other dimensions are possible and are contemplated by the present disclosure. For example, the angle α can be greater than or less than that of the illustrated embodiment. In various embodiments, the angle α is no greater than 15, 20, 25, 30, or 35 degrees. The other dimensions may similarly be altered in other embodiments.

Figure 54:
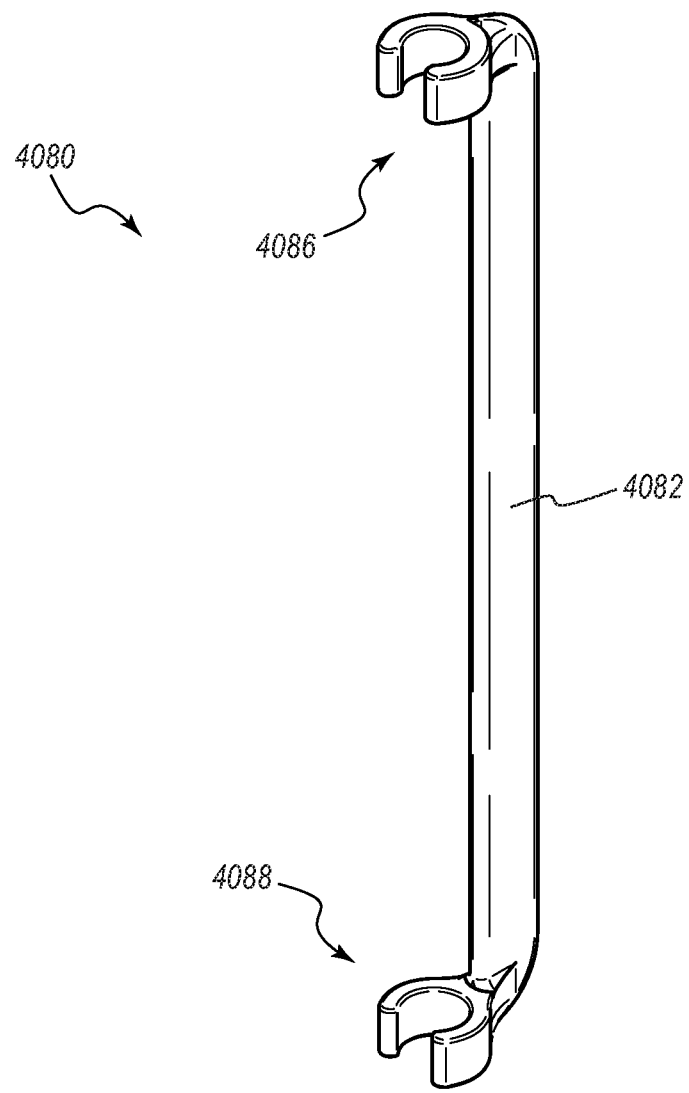
FIG. 54 is a perspective view of an embodiment of a spacer compatible with the system of FIG. 45.

FIG. 54 depicts the spacer 4080 in greater detail. As previously discussed, the spacer 4080 is configured to maintain a predetermined relative position of the sheath assembly 4002 and the catheter assembly 4004 during insertion and/or manipulation of the system 4000 in the patient, such as during introduction of the system 4000 into the esophagus and into contact with an impacted food bolus. In particular, the spacer 4080 can be configured to maintain a relative orientation in which the distal tip 4023 of the catheter 4013 is retracted within the instrument delivery lumen 4054 of the sheath 4016, or stated otherwise, is retracted relative to the distal tip 4013 of the sheath 4016.

The illustrated spacer 4080 is an elongated clip 4082 that includes a proximal fastener 4086 and a distal fastener 4088. The proximal fastener 4086 is configured to selectively attach to and detach from the connector 4043 portion of the catheter hub 4024 (see FIGS. 45 and 51). The distal fastener 4088 is configured to selectively attach to and detach from the connector 4055 portion of the sheath hub 4014 (see FIGS. 45 and 47). The fasteners 4086, 4088 can be of any suitable variety. In the illustrated embodiment, the fasteners 4086, 4088 are spring clips with resiliently flexible arms.

In some embodiments, the spacer 4080 is attached to the system 4000 during manufacture and packaging of the system 4000. Accordingly, when a user removes the system 4000 from the packaging, the spacer 4080 may already be in place. In other embodiments, the spacer 4080 may come separately within the packaging, and instructions for use can indicate that the user can attach the spacer 4080 to the assemblies 4002, 4004 prior to insertion of the system 4000 into the esophagus of the patient.

In some embodiments, such as the illustrated embodiment, the spacer 4080 can be configured to be selectively detached from the assemblies 4002, 4004 and selectively reattached to the assemblies 4002, 4004. For example, in some instances, a user may deploy the positioning element 4018 into contact with the esophageal wall and core through a portion of the blockage using the catheter assembly 4004, such as by moving the catheter assembly 4004 longitudinally back and forth relative to the sheath assembly 4002, which sheath assembly 4002 remains in a substantially fixed orientation relative to the esophagus and the blockage (e.g., food impaction) during the initial phase of coring.

In some instances, after the initial coring, the user may wish to advance the sheath assembly 4002 to a more distal position within the esophagus, such as to be able to core deeper into the blockage. Accordingly, a user may wish to contract the positioning element 4018 (e.g., deflate the balloon 4019) or otherwise transition the positioning element 4018 to a lower profile and then move the system within the esophagus. In some instances, in order to protect the esophagus from inadvertent contact with the esophageal wall, it may be desirable for a user to reattach the spacer 4080 to the specified attachment regions of the assemblies 4002, 4004 to reestablish the fixed longitudinal relationship between the assemblies the ensures the distal tip of the catheter 4026 is retracted within the lumen of the sheath 4016. Thus, in some instances, instructions for use may recommend or require that a user reattach the spacer 4080 prior to any movement within the esophagus when the positioning element 4018 is in the contracted state.

As a further example, the spacer 4080 can be reattached prior to removal of the system 4000 from the esophagus. In other instances, a user may not use the spacer 4080 during retraction. In certain of such instances, the user may fully retract the catheter assembly 4004 from the sheath assembly 4002 (e.g., pull proximally out of the sheath assembly 4002), may then subsequently contract the positioning element 4018 to a low profile, and then may remove the sheath assembly 4002 from the esophagus.

The system 4000 may be used in any of the manners disclosed herein, as suitable. For example, the various methods and/or portions (e.g., a subset of steps) thereof discussed with respect to, e.g., the systems 200, 3000, 3200 can be performed with the system 4000.

Figure 55:
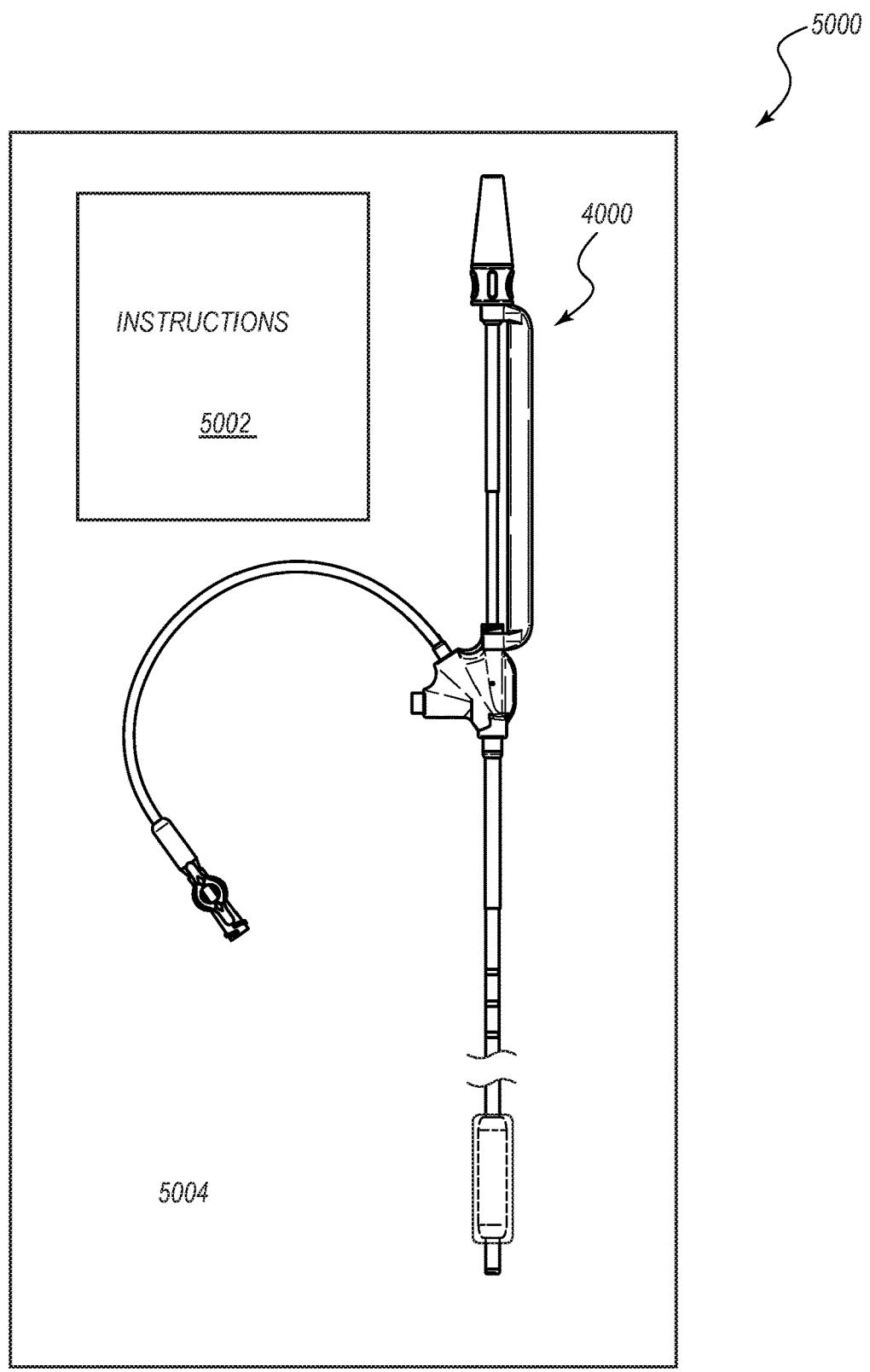
FIG. 55 is an elevation view of an embodiment of a kit that includes the system of FIG. 45.

With reference to FIG. 55, any of the systems or components thereof described herein may be provided in a kit 5000. In some embodiments, the kit 5000 is particularly well suited for use in an emergency room setting. The kit 5000 may be used in blind procedures, such as those in which no direct or indirect visualization of the blockage is performed during the procedure. Accordingly, in some instances, the kit 5000 may be used by practitioners who are not specialized endoscopists, etc.

In the illustrated embodiment, the kit 5000 includes an embodiment of the system 4000. The kit 5000 can further include instructions 5002 for using the embodiment of the system 4000. For example, the instructions for use 5002 may provide directions with respect to any of the methods or processes disclosed herein. By way of further example, the instructions for use 5002 may recite any method and/or other portion of the present disclosure.

The kit 5000 can further include packaging 5004. The system 4000 can be contained within the packaging 5004, and the instructions 5002 can be contained within, printed on, or otherwise made accessible via the packaging 5004.

In various embodiments, the kit 5000—and, in particular, the system 4000 and the instructions for use 5002 thereof—can be approved of or authorized by a regulating body of a particular jurisdiction. For example, the kit 5000, and the instructions 5002 for use thereof, may be approved of or authorized by the Food and Drug Administration of the United States of America and/or may comply with the regulations of other jurisdictions, such as by qualifying for CE marking in the European Union.

The instructions 5002 can provide directions with respect to any of the methods or processes disclosed herein. That is, the instructions 5002 can provide directions for using the system 4000, or components thereof, in accordance with any of the methods or processes disclosed herein. One illustrative example of a set of instructions 5002 for use with one embodiment of the system 4000 is provided below. Other instructions may include more, fewer, and/or different directions than those provided in the illustrative example, and other embodiments of the system 4000 may include more, fewer, and/or different features than those discussed in the instructions.

Example 1

An embodiment of the system 4000 is designed to core and aspirate food impactions. It is comprised of the sheath assembly 4002 and the catheter assembly 4004. The sheath assembly 4002 is a 12 Fr OD with a 0.133" ID, 62 cm in usable length, has a soft, atraumatic tip. It is designed to connect to a standard 10 cc-20 cc syringe for inflation of the balloon 4019. The sheath assembly 4002 uses the low-pressure balloon 4019 to stabilize and center the aspiration catheter 4026 in the esophagus.

The catheter assembly 4004 is used through the working channel 4054 (FIG. 49) of the sheath assembly 4002. The catheter assembly 4004 has a molded tapered handle that is a slip fit connection to the vacuum system in the emergency room of a hospital. It has a beveled distal tip to aid in coring through food impactions. The catheter assembly 4004 extends approximately 2.00" outside the tip of the sheath assembly 4002 during full insertion. In this example, the proximal portion 4026*p* of the catheter 4026 is colored white, and the distal portion 4026*d* is colored gray (see FIG. 51).

The system 4000 can be packaged with instructions for use 5002, which instructions may recite some or all of the following directions. The instructions detail illustrative examples of using the system 4000.

The system 4000 is indicated for removal of food blockage and impaction in the esophagus. The system 4000 may desirably be used by a health care professional with adequate training in the use of the device. The catheter assembly 4004 moves freely through the sheath assembly 4002. Do not remove system 4000 assembly clip 4082 until the sheath assembly 4002 is in final position within the esophagus, which may also be referred to as an anchored position in which the balloon 4019 is fully deployed. Do not use if the system 4000 cannot be advanced to at least 25 cm past the incisors as indicated by the relevant markings.

When repositioning or withdrawing the system 4000, always withdraw the catheter assembly 4004 until the white proximal portion 4026*p* of the catheter 4026 is visible outside the sheath. This will ensure the atraumatic tip of the sheath assembly 4002 is always the leading edge during positioning.

Open the package and carefully remove balloon protector sleeve 4098 from the sheath assembly 4002. Verify that the distal tip of the aspiration catheter is contained within the sheath and does not extend beyond the tip of the sheath.

Introduce the system 4000, into the mouth and then advance beyond the cricopharyngeus into the esophagus.

Advance the system 4000 at least 25 cm from the incisors. Verify the depth by the marking on the external surface of the sheath. Insertion of the system 4000 to a depth of less than 25 cm from the incisors could lead to inadvertent balloon inflation within the pharynx.

Advance the system 4000 to the level of the food impaction as indicated by resistance to further passage of the system 4000.

Withdraw the system 4000 approximately 1-2 cm (e.g., a short distance) from the point of contact of the food impaction. This will allow proper positioning, (i.e., centering) and inflation of the balloon.

Inflate the balloon to its full diameter by attaching a standard 10 cc or 20 cc syringe to the luer lock inflation port and injecting 20 cc's of air into the balloon. Once balloon has been inflated close the stopcock 4064 to seal air within the system. Gently pull on the balloon sheath to confirm the balloon is fully inflated and secured within the esophagus.

Remove the assembly clip 4082 from the system 4000. This will allow free movement of the catheter assembly 4004 relative to the anchored sheath assembly 4002.

Attach standard suction tubing of a suction system to the catheter assembly 4004 handle by pressing tubing firmly onto the handle. Attach the suction system to the wall suction of the hospital in any suitable manner. For example, press fit tubing of the suction system over a wall-mounted nozzle in a hospital room that is connected to the hospital suction source.

Turn on the wall suction. Adjust wall suction to its highest power setting.

The aspiration catheter, attached to suction, will then be employed to core pieces of the food impaction and suction the pieces as cored. The aspiration catheter will be advanced into the food to core pieces of food and then be withdrawn to allow suction. This process will be repetitively performed (coring and suctioning) as needed to clear the impaction. Repeat this action until food impaction is clear. The food impaction may naturally pass into the stomach once a sufficient portion thereof has been cored away.

If necessary or desired, the sheath balloon can be deflated by opening the stopcock and pulling a vacuum on the inflation syringe and re-inflated in order to advance, withdraw or reposition the sheath to optimize clearance of the impaction.

The aspiration catheter should be safely withdrawn into the sheath, and the balloon can be partially or completely deflated to allow free motion of the sheath, to allow advancement of the sheath into any remaining impaction to push any remaining food distally into the stomach. Advancement of the sheath should not be attempted until the aspiration catheter is contained within the confines of the sheath (e.g., the gray distal portion 4026*d* of the aspiration catheter 4026 is visible outside of sheath assembly 4002).

After the food impaction is cleared, withdraw the catheter assembly 4004 until the gray distal portion 4026*d* is visible outside the sheath assembly 4002, open the stopcock and completely deflate the balloon by pulling a vacuum on the inflation syringe.

Withdraw the system 4000 from the esophagus.

With reference again to FIGS. 51 and 53, in some embodiments, the catheter assembly 4004 is particularly well suited for use with any of a variety of standard or otherwise commercially available endoscopes. In some embodiments, the catheter assembly 4004 may be better suited for use with such endoscopes than with certain embodiments of dedicated sheaths. For example, the catheter assemblies can be deployed through a standard working channel of an endoscope. In certain of such instances, the food bolus and progress of the procedure can be visually monitored via the endoscope by a professional during certain uses of the catheter assemblies.

In some instances, the catheter assembly 4004 for use with an endoscope may vary from certain embodiments configured for use with a sheath assembly 4002. For example, in some instances, the catheter assembly 4004 may be devoid of a depth indicator 4027. By way of further example, rather than having differently colored proximal and distal portions 4026p, 4026d, the shaft of the catheter 4026 may be a uniform color along a full length thereof.

In some embodiments, various dimensions of the catheter assembly 4004 can be optimized for use with endoscopes. In some illustrative examples, the total length $L_T$ of the catheter assembly 4004 may be relatively longer, whereas the outer diameter OD and the inner diameter ID are smaller. For example, in one illustrative example, the total length $L_T$ is 128.7±1 centimeters, the outer diameter OD is 0.107±0.005 inches and the inner diameter ID is 0.096±0.005 inches. The remaining dimensions (e.g., the bevel angle and bevel height) may be as previously identified. Other values of the various dimensions are possible and are contemplated by the present disclosure.

Figure 56:
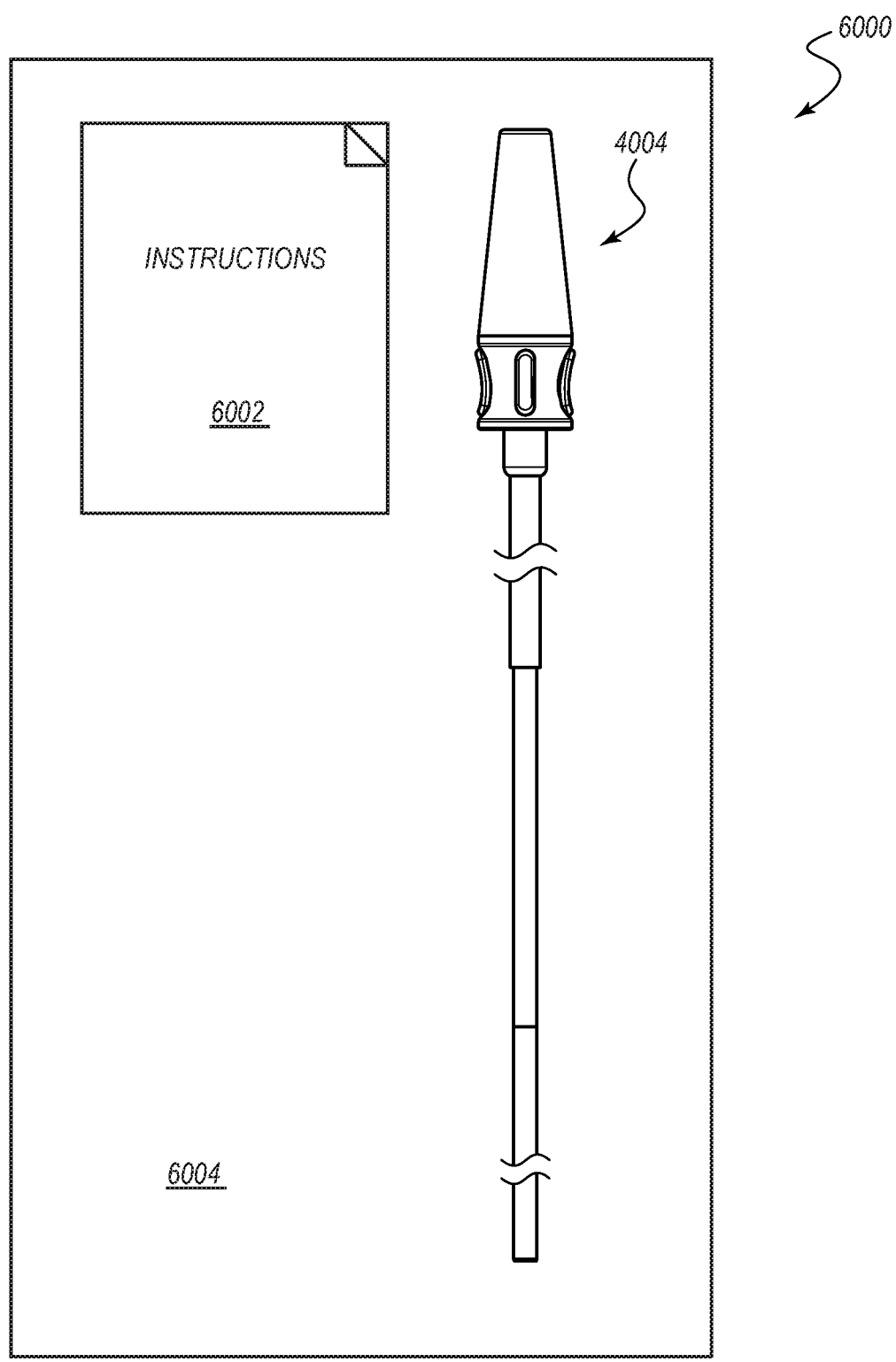
FIG. 56 is an elevation view of another embodiment of a kit that includes an embodiment of the catheter assembly of FIG. 51.

With reference to FIG. 56, any of the catheter assemblies disclosed herein may be provided in a kit 6000. In certain embodiments, the kit 6000 is particularly well suited for use with a standard or otherwise commercially available endoscope. For example, the kit 6000 may be used by an endoscopist or other similarly trained practitioner. In the illustrated embodiment, the kit 6000 includes an embodiment of the catheter assembly 4004. The kit 6000 can further include instructions 6002 for using the embodiment of the catheter assembly 4004. In particular, the instructions 6002 can provide directions to carry out any procedure, procedural step, or other action disclosed herein. By way of further example, the instructions for use 6002 may recite any method and/or other portion of the present disclosure The kit 6000 can further include packaging 6004. The catheter assembly 4004 can be contained within the packaging 6004, and the instructions 6002 can be contained within, printed on, or otherwise made accessible via the packaging 6004.

In various embodiments, the kit 6000—and, in particular, the catheter assembly 4004 and the instructions for use 6002 thereof—can be approved of or authorized by a regulating body of a particular jurisdiction. For example, the kit 6000, and the instructions for use 6002 thereof, may be approved of or authorized by the Food and Drug Administration of the United States of America and/or may comply with the regulations of other jurisdictions, such as by qualifying for CE marking in the European Union.

The instructions 6002 can provide directions with respect to any of the methods or processes disclosed herein. That is, the instructions 6002 can provide directions for using the catheter assembly 4004 in accordance with any of the methods or processes disclosed above. One illustrative example of a set of instructions 6002 for use with one embodiment of the catheter assembly 4004 is provided below. Other instructions may include more, fewer, and/or different directions than those provided in the illustrative example, and other embodiments of the catheter assembly 4004 may include more, fewer, and/or different features than those discussed in the instructions.

Example 2

The catheter assembly 4004 is designed to be used in the esophagus to remove food blockages. It is an 8 Fr OD with a 0.090 inch max ID, 124 cm useable length, single-lumen, braided biocompatible catheter with a sharp distal tip for cutting through the food impaction. The catheter assembly 4004 has a molded, tapered handle that is a slip fit connection to the vacuum system in the hospital.

The catheter assembly 4004 is designed to be used through the working channel (>2.7 mm ID) of a standard endoscope. It is designed to connect to extend outside the distal end of an endoscope by approximately 1 inch when fully inserted.

The catheter assembly 4004 can be packaged with instructions for use 6002, which instructions may recite some or all of the following directions. The instructions detail illustrative examples of using the catheter assembly 4004.

The catheter assembly 4004 is indicated for removal of food blockage/impaction in the esophagus.

The catheter assembly 4004 should be used by a health care professional with adequate training in the use of the device.

Do not use if the device is kinked or damaged in any way.

Do not use if the catheter assembly 4004 does not move freely through the working channel of a standard endoscope with a working channel ID of 2.7 mm or greater.

Following standard practices, introduce a standard endoscope (e.g., through the mount of the patient) to the level of the food impaction.

Insert the catheter assembly 4004 through the working channel of the endoscope until the aspiration catheter is visible through the distal end of the endoscope.

Once positioned in the endoscope, attach standard suction tubing to the catheter handle by pressing tubing firmly onto the handle. Attach the suction system to the wall suction of the hospital in any suitable manner. For example, press fit tubing of the suction system over a wall-mounted nozzle in a hospital room that is connected to the hospital suction source.

Deliver a plurality of (e.g., 4 to 5) drops of water through the irrigation lumen of the endoscope. This will help saturate the food impaction making it easier to aspirate.

The aspiration catheter, attached to suction, will then be employed to core pieces of the food impaction and suction the pieces as cored. The aspiration catheter will be advanced into the food to core pieces of food and then be withdrawn to allow suction. This process will be repetitively performed (coring and suctioning) as needed to clear the impaction. Repeat this step until food impaction is clear (e.g., until food impaction is naturally passed out of the esophagus and into the stomach by the patient).

When the impaction has been cleared, detach the vacuum from catheter handle and remove the catheter assembly 4004 from the endoscope.

FIGS. 57A and 57B depict another embodiment of a sheath assembly 7002 in an undeployed state and in a deployed state, respectively. The sheath assembly 7002 can be used with embodiments of catheter assemblies disclosed herein in manners such as are also disclosed herein.

The sheath assembly 7002 can function similarly to other sheath assemblies disclosed herein. In general, the sheath assembly 7002 includes a positioning element 7018 and an actuator 7060 via which the positioning element 7018 can be deployed and retracted.

As with other embodiments disclosed herein, the sheath assembly 7002 includes hub 7014 that is coupled with a sheath 7016 in any suitable manner. The sheath 7016 defines an instrument deployment lumen 7054 within which a catheter can be positioned, and through which the catheter can be advanced and/or retracted. The sheath 7016 can further define an actuation channel or lumen 7066, which can resemble the inflation channels or lumens 3066, 3266, 4066 described above. All such lumens can allow movement therethrough of an actuation element (such as fluid or, as discussed further hereafter for the present case, an actuation wire or rod) to effect actuation or retraction of a positioning element.

In the illustrated embodiment, the positioning element 7018 comprises an expandable member 7019 of any suitable variety. The expandable member 7019 can, for example, comprise a braided or other configuration of wires or other materials that can be selectively expanded to a larger profile configuration or retracted to a lower profile configuration. For example, the expandable member 7019 can resemble or be formed as a selectively expandable and retractable stent, such as, for example, a braided stent.

With reference to FIGS. 58A and 58B, in other instances, rather than defining a braided sleeve, an expandable member, or positioning element, can define a series of longitudinally extending wires or other elongated elements that are predisposed to flare outwardly when compressed and can assume a low-profile configuration when placed under tension. In still other embodiments, an expandable member, or positioning element, can define a plurality of resilient arms (e.g., FIGS. 59A and 59B) configured to press outwardly into contact with the esophagus. Any other suitable system for expanding into contact with the esophagus and retracting away from contact with the esophagus is contemplated.

In various embodiments, the expandable member 7019 is resiliently flexible and/or comprises a shape-memory material. In various embodiments, the expandable member 7019 may be biased toward a retracted orientation (FIG. 57A), such that the bias must be overcome to deploy the expandable member 7019. The expandable member 7019 may readily return to the retracted orientation under influence of the bias, when so permitted. In other embodiments, the expandable member 7019 may be biased toward the deployed orientation (FIG. 57B), such that actuation of the expandable member 7019 includes permitting the bias to naturally deploy the expandable member 7019. The expandable member 7019 may be returned to the retracted orientation by overcoming the bias. In other embodiments, the expandable member 7019 is not subject to internal or other biases when positioned in either of the retracted or deployed orientations.

A distal end of the expandable member 7019 can be fixed relative to the sheath 7016. A proximal end of the expandable member 7019 can be movable relative to the sheath 7016. For example, the proximal end of the expandable member 7019 can be permitted to translate longitudinally relative to the sheath 7016.

The proximal end of the expandable member 7019 can be coupled with a mechanical linkage 7091 of any suitable variety, such as a wire or rod 7093. The mechanical linkage 7091 can further be coupled with an actuation interface 7095 of any suitable variety, such as a button, lever, switch, slider, etc. The actuation interface 7095 can move the mechanical linkage 7091 so as to effect actuation and retraction of the expandable member 7019. Accordingly, the actuator 7060 can be communicatively coupled with the positioning element 7018. In particular, the actuation interface 7095 is configured to directly, mechanically communicate with the expandable member 7019 via the mechanical linkage 7091.

For example, in the illustrated embodiment, the actuation interface 7095 comprises a switch that is translatable relative to the housing 7014. By urging the switch distally from the proximal position shown in FIG. 57A to the distal position shown in FIG. 57B, the mechanical linkage 7091 is likewise urged distally, which likewise urges the proximal end of the expandable member 7019 distally. Due to the fixed relationship of the distal end of the expandable member 7019 relative to the sheath 7016, the expandable member 7019 can deploy outwardly to the configuration depicted in FIG. 57B. Similarly, urging the switch proximally from the distal position shown in FIG. 57A to the proximal position shown in FIG. 57B can return the expandable member to the retracted orientation shown in FIG. 57A.

FIGS. 58A and 58B depict another embodiment of a sheath assembly 8002 in an undeployed state and in a deployed state, respectively. The sheath assembly 8002 can closely resemble the sheath assembly 7002 just described, but may include a different expandable member 8019 that includes a plurality of longitudinally extending wires or elongated elements 8095. The expandable member 8019 can perform substantially as previously described with respect to the expandable member 7019.

Figures 59A, 59B:
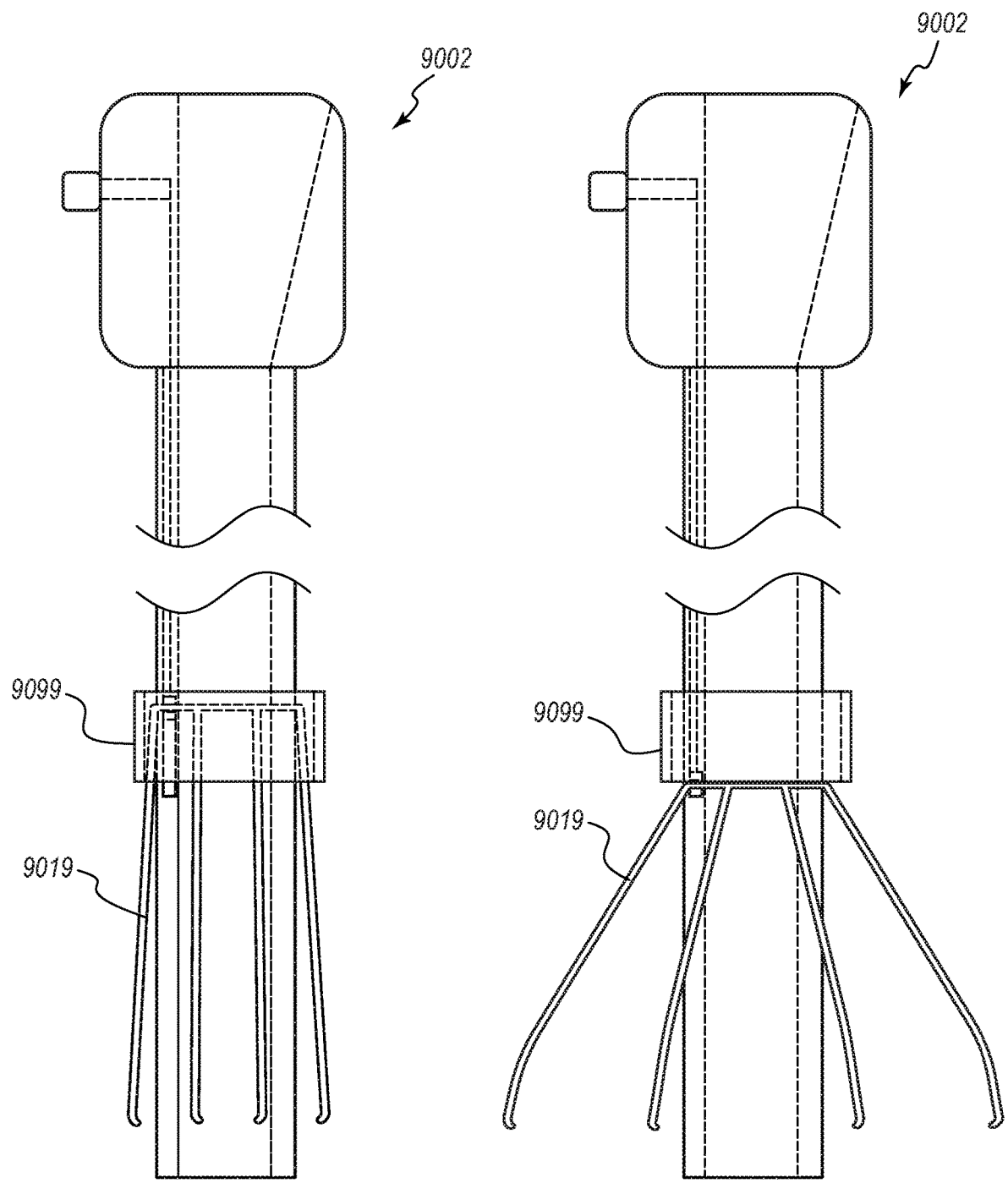
FIG. 59A is an elevation view of another embodiment of a sheath assembly, which can be used with embodiments of systems previously disclosed, the sheath assembly being shown in an undeployed state.
FIG. 59B is another elevation view of the sheath assembly of FIG. 59A shown in a deployed state.

FIGS. 59A and 59B depict another embodiment of a sheath assembly 9002 in an undeployed state and in a deployed state, respectively. The sheath assembly 9002 can closely resemble the sheath assemblies 7002, 8002 just described, but may include a different expandable member 9019 that includes a plurality of resiliently expandable arms 9097. In the illustrated embodiment, the arms 9097 are configured to rotate outward into contact with the esophageal wall when deployed. In particular, in the illustrated embodiment, the arms 9097 are deployed when proximal portions thereof are advanced distally so as to no longer be restrained in a low-profile orientation by a retainer element 9099.

Although various embodiments are described herein, the embodiments are only examples and should not be construed as limiting. The examples described above generally refer to food impactions in the esophagus. However, many other similar impactions can be addressed using the systems and methods described herein. For example, embodiments of the systems may be used with any suitable anatomical tube (e.g., the esophagus, a bronchus, a vessel).

For example, a person can choke while eating, and food can get aspirated and lodge in the trachea, or can also lodge in the lung, specifically any portion of the bronchial tree. Mucus can also become trapped anywhere in the bronchial tree, causing mucus plugging. When this occurs, one or more of the embodiments described herein can be used to core and suction said food or mucus, such as by placing the device, for example, through the working channel of a flexible or rigid bronchoscope as opposed to an endoscope.

One or more of the embodiments described herein can also be used to core, suction and remove trapped blood or blood clots anywhere in the GI tract, specifically the esophagus, stomach, small intestine or large intestine.

One or more of the embodiments described herein can also be used to core, suction and remove trapped food, blood or blood clots, or mucus or mucus plugs, anywhere in the pulmonary organ system, i.e., the trachea or lung i.e. anywhere in the bronchial tree.

One or more of the embodiments described herein can be used to core and remove blood or blood clots, or atheroma or atheromatous plaque anywhere in the vasculature system, i.e. great arteries or veins, or peripheral vasculature i.e. the peripheral arteries or veins. To core harder materials such as calcified plaque, a stainless steel tip can be attached to the end of the suction catheter.

One or more of the embodiments described herein can also be used to core and remove blood or blood clots, or atheroma or atheromatous plaque anywhere in the heart or coronary arteries. To core harder materials such as calcified plaque, a stainless steel tip can be attached to the end of the suction catheter.

In another example, one or more of the embodiments described herein can be used to core and suction kidney stones from the urinary system, specifically the ureters, bladder and kidneys. To core harder materials such as calcified, struvite, oxalate or uric acid kidney stones a stainless steel tip can be attached to the end of the suction catheter.

In yet another example, one or more of the embodiments described herein can be used to core and remove gallstones or tumors lodged in the biliary tree (common bile duct or peripheral ducts). Harder materials can be cored by attaching a stainless steel tip to the end of the suction catheter.

Although the foregoing detailed description contains many specifics for the purpose of illustration, a person of ordinary skill in the art will appreciate that many variations and alterations to the following details can be made and are considered to be included herein. Accordingly, the foregoing embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

As used in this specification and the appended claims, the singular forms "a," "an" and "the" include plural referents unless the context clearly dictates otherwise. Thus, for example, reference to "a layer" includes a plurality of such layers.

In this disclosure, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the component structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in any suitable manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "substantially" refers to the complete or nearly-complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Moreover, for references to approximations (which are made throughout this specification), such as by use of the terms "about" or "approximately," or other terms, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially perpendicular" is recited with respect to a feature, it is understood that in further embodiments, the feature can have a precisely perpendicular orientation.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

References throughout this specification to "an example," if any, mean that a particular feature, structure, or characteristic described in connection with the example is included in at least one embodiment. Thus, appearances of the phrases "in an example" in various places throughout this specification are not necessarily all referring to the same embodiment.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of claims [x] through the claim that immediately precedes this one" where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:

1. A method comprising:
    inserting a tubular member into an esophagus of a patient in which a blockage is present, the tubular member defining a channel;
    advancing a catheter tube through the channel of the tubular member into contact with the blockage;
    coring the blockage via a distal tip of the catheter tube to dislodge a piece from the blockage; and
    suctioning the dislodged piece through the catheter tube.

2. The method of claim 1 further comprising:
    coring the blockage additional times via the distal tip of the catheter tube to dislodge additional pieces from the blockage; and
    suctioning the additional dislodged pieces through the catheter tube until the blockage naturally passes through the esophagus and into the stomach of the patient.

3. The method of claim 1, wherein a catheter assembly comprises the catheter tube and further comprises a proximal end, the method further comprising coupling the proximal end of the catheter assembly with a vacuum line.

4. The method of claim 3, further comprising coupling the vacuum line with a hospital vacuum source.

5. The method of claim 1, wherein said coring the blockage via the distal tip of the catheter tube takes place while the tubular member remains in place within the esophagus.

6. The method of claim 1, wherein the tubular member comprises an endoscope.

7. The method of claim 1, wherein the tubular member comprises a sheath that is coupled with a positioning element.

8. The method of claim 7, wherein the positioning element is in an undeployed stated during said inserting the tubular member into the esophagus, and wherein the method further comprises expanding the positioning element into contact with the esophagus.

9. The method of claim 8, wherein the positioning element comprises a balloon, and wherein said expanding the positioning element comprises inflating the balloon with a fluid.

* * * * *